United States Patent
Steinmetzer et al.

(10) Patent No.: US 8,207,378 B2
(45) Date of Patent: Jun. 26, 2012

(54) TRYPSIN-LIKE SERINE PROTEASE INHIBITORS, AND THEIR PREPARATION AND USE

(75) Inventors: Torsten Steinmetzer, Jena (DE); Andrea Schweinitz, Jena (DE); Joerg Stuerzebecher, Erfurt (DE); Peter Steinmetzer, Jena (DE); Anett Soeffing, Weimar (DE); Andreas Van De Locht, Munich (DE); Silke Nicklisch, Leipzig (DE); Claudia Reichelt, Leipzig (DE); Friedrich-Alexander Ludwig, Leipzig (DD); Alexander Schulze, Grosstreben (DE); Mohammed Daghisch, Leipzig (DE); Jochen Heinicke, Leipzig (DE)

(73) Assignee: The Medicines Company (Leipzig) GmbH, Leipzig (DE)

( * ) Notice: Subject to any disclaimer, the term of this patent is extended or adjusted under 35 U.S.C. 154(b) by 385 days.

(21) Appl. No.: 12/429,766

(22) Filed: Apr. 24, 2009

(65) Prior Publication Data

US 2010/0022781 A1 Jan. 28, 2010

Related U.S. Application Data

(63) Continuation-in-part of application No. PCT/EP2007/009220, filed on Oct. 24, 2007.

(30) Foreign Application Priority Data

Oct. 24, 2006 (DE) .................. 10 2006 050 672

(51) Int. Cl.
*C07C 303/00* (2006.01)
(52) U.S. Cl. .......................... 564/92; 564/86
(58) Field of Classification Search .............. 564/92, 564/86
See application file for complete search history.

(56) References Cited

U.S. PATENT DOCUMENTS

| | | | |
|---|---|---|---|
| 5,518,735 A | 5/1996 | Stürzebecher et al. |
| 5,602,253 A | 2/1997 | Antonsson et al. |
| 5,705,487 A | 1/1998 | Schacht et al. |
| 5,707,966 A | 1/1998 | Schacht et al. |
| 5,710,130 A | 1/1998 | Schacht et al. |
| 5,726,159 A | 3/1998 | Schacht et al. |
| 5,786,328 A | 7/1998 | Dennis et al. |
| 5,863,929 A | 1/1999 | Klimkowski et al. |
| 5,914,319 A | 6/1999 | Schacht et al. |
| 6,030,972 A | 2/2000 | Böhm et al. |
| 6,472,393 B1 | 10/2002 | Aliagas-Martin et al. |
| 6,586,405 B2 | 7/2003 | Semple et al. |
| 6,624,169 B1 | 9/2003 | Wilhelm et al. |
| 6,680,320 B2 | 1/2004 | Wilhelm et al. |
| 6,831,196 B2 | 12/2004 | Stürzebecher et al. |
| 6,841,701 B2 | 1/2005 | Stürzebecher et al. |
| 6,841,702 B2 | 1/2005 | Magdolen et al. |
| 7,038,074 B2 | 5/2006 | Moroder et al. |
| 7,049,460 B1 | 5/2006 | Magdolen et al. |
| 7,208,521 B2 | 4/2007 | Magdolen et al. |
| 7,342,018 B2 | 3/2008 | Wilhelm et al. |
| 7,407,982 B2 | 8/2008 | Steinmetzer et al. |
| 7,538,216 B2 | 5/2009 | Sperl |
| 7,608,623 B2 | 10/2009 | Sperl et al. |
| 2004/0087511 A1 | 5/2004 | Shiraishi et al. |
| 2004/0266766 A1 | 12/2004 | Sperl |
| 2005/0119190 A1 | 6/2005 | Stürzebecher et al. |
| 2005/0176993 A1 | 8/2005 | Stürzebecher et al. |
| 2006/0068457 A1 | 3/2006 | Ziegler et al. |
| 2006/0148901 A1 | 7/2006 | Stürzebecher et al. |
| 2007/0055065 A1 | 3/2007 | Stürzebecher et al. |
| 2007/0066539 A1 | 3/2007 | Stürzebecher et al. |
| 2008/0261998 A1 | 10/2008 | Sperl et al. |
| 2009/0117185 A1 | 5/2009 | Steinmetzer et al. |
| 2010/0022781 A1 | 1/2010 | Steinmetzer et al. |

FOREIGN PATENT DOCUMENTS

| | | |
|---|---|---|
| CA | 2 412 181 | 12/2002 |
| CH | 689 611 | 7/1999 |
| DE | 42 43 858 | 6/1994 |
| DE | 100 29 015 | 12/2001 |
| DE | 100 290 014 | 12/2001 |
| DE | 102 12 555 | 9/2003 |
| DE | 102 10 590 | 10/2003 |
| DE | 103 01 300 | 7/2004 |
| EP | 0 183 271 | 6/1986 |
| EP | 0 669 317 | 8/1995 |
| EP | 0 672 658 | 9/1995 |
| EP | 1 364 960 | 11/2003 |
| WO | WO 92/08709 | 5/1992 |
| WO | WO 94/18185 | 8/1994 |
| WO | WO 94/29336 | 12/1994 |
| WO | WO 95/17885 | 7/1995 |
| WO | WO 95/29189 | 11/1995 |
| WO | WO 96/25426 | 8/1996 |
| WO | WO 97/23499 | 7/1997 |

(Continued)

OTHER PUBLICATIONS

Schweinitz et al.STN Accession No. 2006:672035 Document No. 145:347782,Abstract of Medicinal Chemistry,vol. 2, No. 4, Jul. 2006 , pp. 349-361(13).*

(Continued)

*Primary Examiner* — Nizal Chandrakumar
(74) *Attorney, Agent, or Firm* — Clark & Elbing LLP

(57) ABSTRACT

The invention relates to inhibitors of trypsin-like serine proteases of the general formula (I) which, as well as plasmin, also inhibit plasma kallikrien, and to their preparation and use as medicaments, preferably for treatment of blood loss, especially in the case of hyperfibrinolytic states, in organ transplants or heart surgery interventions, in particular with a cardiopulmonary bypass, or as a constituent of a fibrin adhesive.

33 Claims, 19 Drawing Sheets

FOREIGN PATENT DOCUMENTS

| WO | WO 99/05096 | | 2/1999 |
|---|---|---|---|
| WO | WO 00/04954 | | 2/2000 |
| WO | WO 00/05245 | | 2/2000 |
| WO | WO 00/14110 | | 3/2000 |
| WO | WO 00/17158 | | 3/2000 |
| WO | WO 00/58346 | | 10/2000 |
| WO | WO 00/64470 | | 11/2000 |
| WO | WO 01/81314 | | 11/2001 |
| WO | WO 01/96286 | | 12/2001 |
| WO | WO 01/96366 | | 12/2001 |
| WO | WO 01/97794 | | 12/2001 |
| WO | WO 02/06280 | | 1/2002 |
| WO | WO 02/14349 | | 2/2002 |
| WO | WO 02/20475 | | 3/2002 |
| WO | WO 02/50056 | | 6/2002 |
| WO | WO 03/070229 | | 8/2003 |
| WO | WO 2004062657 | * | 6/2004 |
| WO | WO 2004/062657 | | 7/2004 |
| WO | WO 2005026198 | * | 3/2005 |

OTHER PUBLICATIONS

Akers, "Excipient-Drug Interactions in Parenteral Formulations," *J. Pharm. Sci.* 91:2283-2300 (2002).

Asghar et al., "Human Plasma Kallikreins and Their Inhibition by Amidino Compounds," *Biochim. Biophys. Acta* 438:250-264 (1976).

Asimakopoulos et al., "Cardiopulmonary Support and Physiology: An Anti-Inflammatory Property of Aprotinin Detected as the Level of Leukocyte Extravasation," *J. Thorac. Cardiovasc. Surg.* 120:361-369 (2000).

Avidan et al., "Comparison of Structured Use of Routine Laboratory Tests or Near-Patient Assessment with Clinical Judgement in the Management of Bleeding After Cardiac Surgery," *Br. J. Anaesth.* 92:178-186, (2004).

Baker et al., "Inhibition of Cancer Cell Urokinase Plasminogen Activator by its Specific Inhibitor PAI-2 and Subsequent Effects on Extracellular matrix Degradation," *Cancer Research* 50: 4676-4684 (1990).

Banke et al., "Increase of Anti-Metastatic Efficacy by Selectivity-But Not Affinity-Optimization of Synthetic Serine Protease Inhibitors," *Biol. Chem.* 384:1515-1525 (2003).

Bhoola et al., "Bioregulation of Kinins: Kallikreins, Kininogens, and Kininases," *Pharmacol. Rev.* 44:1-80 (1992).

Bookser et al., "Syntheses of Quadruply Two-and Three-Atom, Aza-Bridged, Cofacial Bis (5,10,15,20-Tetraphenylporphyrins)," *J. Am. Chem. Soc.* 113:4208-4218 (1991).

Brown et al.,"Meta-Analysis Comparing the Effectiveness and Adverse Outcomes of Antifibrinolytic Agents in Cardiac Surgery," *Circulation* 115:2801-2813 (2007).

Cajot et al., "Plasminogen-Activator Inhibitors Type 1 is a Potent Natural Inhibitor of Extracellular Matrix Degradation by Fibrosarcoma and Colon Carcinoma Cells," *Proc. Natl. Acad. Sci USA* 87:6939-6943 (1990).

Cammerer et al., "The Predictive Value of Modified Computerized Thromboelastography and Platelet Function Analysis for Postoperative Blood Loss in Routine Cardiac Surgery," *Anesth. Analg.* 96:51-57 (2003).

Choi-Sledeski et al., "Discovery of an Orally Efficacious Inhibitor of Coagulation Factor Xa Which Incorporates a Neutral $P_1$ Ligand," *J. Med. Chem.* 46:681-684 (2003).

Clement, "Reduction of N-Hydroxylated Compounds: Amidoximes (N-Hydroxyamidines) as Pro-Drugs of Amidines," *Drug Metabolism Reviews*, 34:565-579 (2002).

Collen et al., "In Vivo Studies of a Synthetic Inhibitor of Thrombin," *J. Lab. Clin. Med.* 99:76-83 (1982).

Coussens et al., "Matrix Metalloproteinase Inhibitors and Cancer: Trials and Tribulations," *Science* 295:2387-2392 (2002).

Dexter et al., "*N,N*-Dimethylformamide-Induced Alteration of Cell Culture Characteristics and Loss of Tumorigenicity in Cultured Human Colon Carcinoma Cells," *Cancer Res.* 39:1020-1025 (1979).

Dietrich et al., "High-Dose Aprotinin in Cardiac Surgery: Is High-Dose High Enough? An Analysis of 8281 Cardiac Surgical Patients Treated with Aprotinin," *Anesth. Analg.* 103:1074-1081 (2006).

Dietrich et al., "Aprotinin and Anaphylaxis: Analysis of 12,403 Exposures to Aprotinin in Cardiac Surgery," *Ann. Thorac. Surg.* 84:1144-1150 (2007).

Dietrich et al., "Effects of Aprotinin Dosage on Renal Function: An Analysis of 8,548 Cardiac Surgical Patients Treated with Different Dosages of Aprotinin," *Anesthesiology* 108:189-198 (2008).

Dietrich et al., "CU-2010-A Novel Small Molecule Protease Inhibitor with Antifibrinolytic and Anticoagulant Properties," *Anesthesiology*, 110:123-130 (2009).

Dixon, "The Determination of Enzyme Inhibitor Constants," *Biochem. J.* 55:170-171 (1953).

Duggan et al., "Urokinase Plasminogen Activator and Urokinase Plasminogen Activator Receptor in Breast Cancer," *Int. J. Cancer* 61:597-600 (1995).

Edmunds et al., "Thrombin During Cardiopulmonary Bypass," *Ann. Thorac. Surg.* 82:2315-2322 (2006).

Enyedy et al., "Structure-Based Approach for the Discovery of Bis-benzamidines as Novel Inhibitors of Matriptase," *J. Med. Chem.* 44:1349-1355 (2001).

Eriksson et al., "The Direct Thrombin Inhibitor Melagatran Followed by Oral Ximelagatran Compared with Enoxaparin for the Prevention of Venous Thromboembolism after Total Hip or Knee Replacement: the EXPRESS study," *Journal of Thrombosis and Haemostasis*, 1:2490-2496 (2003).

Fareed et al. "Inhibition of Serine Proteases by Low Molecular Weight Peptides and Their Derivatives," *Ann. N. Y. Acad. Sci.* 370:765-784 (1981).

Fergusson et al., "A Comparison of Aprotinin and Lysine Analogues in High-Risk Cardiac Surgery," *N. Engl. J. Med.* 358:2319-2331 (2008).

Ferraris et al., "Perioperative Blood Transfusion and Blood Conservation in Caridac Surgery: The Society of Thoracic Surgeons and the Society of Cardiovascular Anesthesiologists Clinical Practice Guideline," *Ann. Thorac. Surg.* 83:S27-S86 (2007).

Francis et al., "Comparison of Ximelagatran with Warfarin for the Prevention of Venous Thromboembolism after Total Knee Replacement," *N. Engl. J. Med.* 349:1703-1712 (2003).

Frérot et al., "PyBOP® and PyBroP: Two reagents for the Difficult Coupling of the α,α-Dialkyl Amino Acid, Aib," *Tetrahedron*, 47:259-270 (1991).

Friedrich et al., "Catalytic Domain Structures of MT-SP1/Matriptase, a Matrix-degrading Transmembrane Serine Proteinase," *J. Biol. Chem.* 277:2160-2168 (2002).

Fritz et al., "Biochemistry and Applications of Aprotinin, the Kallikrein Inhibitor from Bovine Organs," *Arzneim. Forsch./Drug. Res.* 33:479-494 (1983).

Gabriel et al., "Design of Benzamidine-Type Inhibitors of Factor Xa," *J. Med. Chem.* 41:4240-4250 (1998).

Garrett et al., "Synthesis of Potent and Selective Inhibitors of Human Plasma Kallikrein," *Bioorg. Med. Chem. Lett.* 9:301-306 (1999).

Garrett et al., "Peptide Aldehyde Inhibitors of the Kallikreins: An Investigation of Subsite Interactions with Tripeptides Containing Structural Variations at the Amino Terminus," *J. Pept. Res.* 52:60-71 (1998).

Gerotziafas et al., "In Vitro Inhibition of Thrombin Generation, After Tissue Factor Pathway Activation, by the Oral, Direct Factor Xa Inhibitor Rivaroxaban," *J. Thromb. Haemost.* 5:886-888 (2007).

Griffin, "Role of Surface in Surface-Dependent Activation of Hageman Factor (Blood Coagulation Factor XII)," *Proc. Natl. Acad. Sci. USA* 75:1998-2002 (1978).

Gustafsson et al., "Effects of Melagatran, a New Low-Molecular-Weight Thrombin Inhibitor, on Thrombin and Fibrinolytic Enzymes," *Thromb. Haemost.* 79:110-118 (1998).

Gustafsson et al., "Effects of Inogatran, a New Low-Molecular-Weight Thrombin Inhibitor, in Rat Models of Venous and Arterial Thrombosis, Thrombolysis and Bleeding Time," *Blood Coagulation and Fibrinolysis* 7:69-79 (1996).

Gustafsson et al., "The Direct Thrombin Inhibitor Melagatran and Its Oral Prodrug H 376/95: Intestinal Absorption Properties, Biochemical and Pharmacodynamic Effects," *Thromb. Res.* 101:171-181 (2001).

Gustafsson et al., "A New Oral Anticoagulant: The 50-Year Challenge," *Nature Reviews Drug Discovery* 3:649-659 (2004).

Hara et al., "DX-9065a, a New Synthetic, Potent Anticoagulant and Selective Inhibitor for Factor Xa," *Thromb. Haemost.* 71:314-319 (1994).

Henry et al., "Anti-Fibrinolytic Use for Minimising Perioperative Allogeneic Blood Transfusion (Review)," *Cochrane Database Syst. Rev.* CD001886 Wiley Publishers (2007).

Herbert et al., "DX 9065A, a Novel, Synthetic, Selective and Orally Active Inhibitor of Factor Xa: In Vitro and In Vivo Studies," *J. Pharmacol. Exp. Ther.* 276:1030-1038 (1996).

Hill et al., "Aprotinin but Not Tranexamic Acid Inhibits Cytokine-Induced Inducible Nitric Oxide Synthase Expression," *Anesth. Analg.* 84:1198-202 (1997).

Ho et al., "Exploratory Solid-Phase Synthesis of Factor Xa Inhibitors: Discovery and Application of $P_3$-Heterocyclic Amides as Novel Types of Non-Basic Arginine Surrogates," *Bioorg. Med. Chem. Lett.* 9:3459-3464 (1999).

Hooper et al., "Type II Transmembrane Serine Proteases," *J. Biol. Chem.* 276:857-860 (2001).

Ihara et al., "Prometastatic Effect of N-Acetylglucosaminyltransferase V Is Due to Modification and Stabilization of Active Matriptase by Adding β1-6 GlcNAc Branching," *J. Biol. Chem.* 277:16960-16967 (2002).

Isobe, "Inhibitory Effect of Gabexate (FOY) on Contact System," *Blood & Vessel* 12:135-138 (1981).

Judkins et al., "A Versatile Synthesis of Amidines from Nitriles Via Amidoximes," *Synthetic Communications* 26: 4351-4367 (1996).

Kang et al., "Tissue Microarray Analysis of Hepatocyte Growth Factor/Met Pathway Components Reveals a Role for Met, Matriptase, and Hepatocyte Growth Factor Activator Inhibitor 1 in the Progression of Node-negative Breast Cancer," *Cancer Res.* 63:1101-1105 (2003).

Kaplan, "Initiation of the Intrinsic Coagulation and Fibrinolytic Pathways of Man: The Role of Surfaces, Hageman Factor, Prekallikrein, High Molecular Weight Kininogen, and Factor XI," *Prog. Hemost. Thromb.* 4:127-175 (1978).

Karkouti et al., "A Propensity Score Case-Control Comparison of Aprotinin and Tranexamic Acid in High-Transfusion-Risk Cardiac Surgery," *Transfusion* 46:327-338 (2006).

Katz et al., "Engineering Inhibitors Highly Selective for the S1 Sites of Ser190 Trypsin-Like Serine Protease Drug Targets," *Chem. Biol.* 8:1107-1121 (2001).

Kettner et al., "Inactivation of Trypsin-Like Enzymes with Peptides of Arginine Chloromethyl Ketone," *Methods in Enzymology* 80:826-843 (1981).

Kettner et al., "The Selective Inhibition of Thrombin by Peptides of Boroarginine," *J. Biol. Chem.* 265, 18289-18297 (1990).

Kettner et al., "The Selective Affinity Labeling of Factor $X_a$ by Peptides of Arginine Chloromethyl Ketone," *Thromb. Res.* 22:645-652 (1981).

Kim et al., "Preparation of Argatroban Analog Thrombin Inhibitors with Reduced Basic Guanidine Moiety, and Studies of Their Cell Permeability and Antithrombotic Activities," *Med. Chem. Res.* 377-383 (1996).

Kirk, "4-Lithio-1-Tritylimidazole as a Synthetic Intermediate. Synthesis of Imidazole-4-Carboxaldehyde," *J. Heterocyclic Chem.* 22:57-59 (1985).

Kleinschnitz et al., "Targeting Coagulation Factor XII Provides Protection from Pathological Thrombosis in Cerebral Ischemia Without Interfering With Hemostasis," *J. Exp. Med.* 203:513-518 (2006).

Kruger et al., "Host TIMP-1 Overexpression Confers Resistance to Experimental Brain Metastasis of a Fibrosarcoma Cell Line," *Oncogene* 16:2419-2423 (1998).

Kruger et al., "The Bacterial *LacZ* Gene: An Important Tool for Metastasis Research and Evaluation of New Cancer Therapies," *Cancer and Metastasis Reviews* 17:285-294 (1999).

Künzel et al., "4-Amidinobenzylamine-Based Inhibitors of Urokinase," *Bioorg. Med. Chem. Lett.* 12:645-648 (2002).

Laffey et al., "The Systemic Inflammatory Response to Cardiac Surgery," *Anesthesiology* 97:215-252 (2002).

Landis et al., "The Antithrombotic and Antiinflammatory Mechanisms of Action of Aprotinin," *Ann. Thorac. Surg.* 72:2169-2175 (2001).

Lawson et al., "Studies on the Inhibition of Human Thrombin: Effects of Plasma and Plasma Constituents," *Folia Haematol. Int. Mag. Klin. Morphol. Blutforsch.* 109, 52-60 (1982).

Leadley, "Coagulation Factor Xa Inhibition: Biological Background and Rationale," *Curr. Topics in Med. Chem.* 1:151-159 (2001).

Lee et al., "Noncovalent Tripeptidic Thrombin Inhibitors Incorporating Amidrazone, Amine and Amidine Functions at P1," *Bioorg. Med. Chem. Lett.* 12:1017-1022 (2002).

Lee et al., "Noncovalent Thrombin Inhibitors Incorporating an Imidazolylethynyl P1," *Bioorganic & Medicinal Chemistry Letters*, 10:2775-2778 (2000).

Lee et al., "Activation of Hepatocyte Growth Factor and Urokinase/Plasminogen Activator by Matriptase, an Epithelial Membrane Serine Protease," *J. Biol. Chem.* 275:36720-36725 (2000).

Levy et al., "Inflammatory Response to Cardiopulmonary Bypass," *Ann. Thorac. Surg.* 75:S715-S720 (2003).

Lin et al., "Characterization of a Novel, Membrane-bound, 80-kDa Matrix-degrading Protease from Human Breast Cancer Cells," *J. Biol. Chem.* 272:9147-9152 (1997).

Lin et al., "Molecular Cloning of cDNA for Matriptase, a Matrix-degrading Serine Protease with Trypsin-like Activity," *J. Biol. Chem.* 274:18231-18236 (1999).

Lin et al., "Purification and Characterization of a Complex Containing Matriptase and a Kunitz-type Serine Protease Inhibitor from Human Milk," *J. Biol. Chem.* 274:18237-18242 (1999).

Long et al., "Synthesis and Evaluation of the Sunflower Derived Trypsin Inhibitor as a Potent Inhibitor of the Type II Transmembrane Serine Protease, Matriptase," *Bioorg. Med. Chem. Lett.* 11:2515-2519 (2001).

Maduskuie el al., "Rational Design and Synthesis of Novel, Potent Bis-Phenylamidine Carboxylate Factor Xa Inhibitors," *J. Med. Chem.* 41:53-62 (1998).

Maignan et al., "The Use of 3D Structural Data in the Design of Specific Factor Xa Inhibitors," *Curr. Top. Med. Chem.* 1:161-174 (2001).

Mangano et al., "The Risk Associated with Aprotinin in Cardiac Surgery," *N. Engl. J. Med.* 354:353-365 (2006).

Mannucci et al., "Prevention and Treatment of Major Blood Loss," *N. Engl. J. Med.* 356:2301-2311 (2007).

Mignatti et al., "Biology and Biochemistry of Proteinases in Tumor Invasion," *Physiological Reviews* 73:161-193 (1993).

Mohan et al., "Solid-Phase Synthesis of N-Substituted Amidinophenoxy Pyridines as Factor XA Inhibitors," *Bioorg. Med. Chem. Lett.* 8:1877-1882 (1998).

Mojcik et al., "Aprotinin and the Systemic Inflammatory Response After Cardiopulmonary Bypass," *Ann. Thorac. Surg.* 71:745-754 (2001).

Morrissette et al., "Low Molecular Weight Thrombin Inhibitors With Excellent Potency, Metabolic Stability, and Oral Bioavailability," *Bioorg. Med. Chem. Lett.* 14:4161-4164 (2004).

Mouton et al., "Effect of Aprotinin on Renal Dysfunction in Patients Undergoing On-Pump and Off-Pump Cardiac Surgery: A Retrospective Observational Study," *Lancet* 371:475-482 (2008).

Muramatu et al., "Inhibitory Effects of ω-Amino Acid Esters on Trypsin, Plasmin, Plasma Kallikrein and Thrombin," *Biochim. Biophys. Acta* 242:203-208 (1971).

Muramatu et al., "Inhibitory Effects of ω-Guanidino Acid Esters on Trypsin, Plasmin, Plasma Kallikrein and Thrombin," *Biochim. Biophys. Acta* 268:221-224 (1972).

Muramatu et al., "Inhibitory Effects of Aryl *trans*-4 (Aminomethyl) Cyclohexanecarboxylate and Aryl *trans*-4-(Guanidinomethyl) Cyclohexanecarboxylate on Serine Proteases, and Their Antiallergic Effects," *Hoppe-Seyler's Z. Physiol. Chem.* 363:203-211 (1982).

Nar et al., "Structural Basis for Inhibition Promiscuity of Dual Specific Thrombin and Factor Xa Blood Coagulation Inhibitors," *Structure*, 9:29-37 (2001).

Nelson et al., "Stereoselective Synthesis of a Potent Thrombin Inhibitor by a Novel P2-P3 Lactone Ring Opening," *J. Org. Chem.* 69:3620-3627 (2004).

Oberst et al., "Expression of the Serine Protease Matriptase and Its Inhibitor HAI-1 in Epithelial Ovarian Cancer: Correlation with Clinical Outcome and Tumor Clinicopathological Parameters," *Clin. Cancer Res.* 8:1101-1107 (2002).

Ohno et al., "FOY: [Ethyl P-(6-Guanidinohexanoyloxy) Benzoate] Methanesulfonate as a Serine Proteinase Inhibitor. I. Inhibition of Thrombin and Factor Xa in Vitro," *Thromb. Res.* 19:579-588 (1980).

Okada et al., "Development of Potent and Selective Plamin and Plasma Kallikrein Inhibitors and Studies on the Structure-Activity Relationship," *Chem. Pharm. Bull.* 48:1964-1972 (2000).

Okada et al., "Development of Plasmin and Plasma Kallikrein Selective Inhibitors and their Effect on M1 (Melanoma) and HT29 Cell Lines," *Bioorg. Med. Chem. Lett.* 10:2217-2221 (2000).

Okada et al., "Development of Plasma Kallikrein Selective Inhibitors," *Biopolymers* 51:41-50 (1999).

Okamoto et al., "Recent Studies of the Synthetic Selective Inhibitors; With Special Reference to Non-Plasmin Fibrinolytic Enzyme, Plasmin and Plasma-Kallikrein," *Thromb. Res., Suppl. VIII*, 131-141 (1988).

Ossowski et al., "Antibodies to Plasminogen Activator Inhibit Human Tumor Metastasis," *Cell* 35:611-619 (1983).

Ostrem et al., "Discovery of a Novel, Potent, and Specific Family of Factor Xa Inhibitors via Combinatorial Chemistry," *Biochemistry* 37:1053-1059 (1998).

Patani et al., "Bioisosterism: A Rational Approach in Drug Design." *Chem. Rev.* 96:3147-3176 (1996), pp. 3147-3148 and 3170.

Pauls et al., "The Design of Competitive, Small-Molecule Inhibitors of Coagulation Factor Xa," *Front. in Med. Chem.*, 1:129-152 (2004).

Pedersen et al., "Prognostic Impact of Urokinase, Urokinase Receptor, and Type 1 Plasminogen Activator Inhibitor in Squamous and Large Cell Lung Cancer Tissue" *Cancer Res.* 54:4671-4675 (1994).

Perzborn et al., "In Vitro and In Vivo Studies of the Novel Antithrombotic Agent BAY 59-7939—an Oral, direct Factor Xa Inhibitor," *J. Thromb. & Haemost.* 3:514-521 (2005).

Phillips et al., "Discovery of N-[2-[5-[Amino(imino)methyl]-2-hydroxyphenoxy]-3,5-difluoro-6-[3-(4,5-dihydro-1-methyl-1H-imidazol-2-yl)phenoxy]pyridin-4-yl]-N-methylglycine (ZK-807834): A Potent, Selective, and Orally Active Inhibitor of the Blood Coagulation Enzyme Factor Xa," *J. Med. Chem.* 41:3557-3562 (1998).

Quan et al., "Bisbenzamidine Isoxazoline Derivatives as Factor Xa Inhibitors," *Bioorg. Med. Chem. Lett.* 7:2813-2818 (1997).

Quan et al., "Discovery of 1-(3'-Aminobenzisoxazol-5'-yl)-3-trifluormethyl-N-[2-fluoro-4-[(2'-dimethylaminomethyl)imidazol-1-yl]phenyl]-1H-pyrazole-5-carboxyamide Hydrochloride (Razaxaban), a Highly Potent, Selective, and Orally Bioavailable Factor Xa Inhibitor," *J. Med. Chem.* 48:1729-1744 (2005).

Quan et al., "The Race to Orally Active Factor Xa Inhibitor: Recent Advances," *Curr. Opin. In Drug Discov. Devel.* 7:460-469 (2004).

Ratnoff, "Studies on the Inhibition of Ellagic Acid-Activated Hageman Factor (factor XII) and Hageman Factor Fragments," *Blood* 57:55-58 (1981).

Renatus et al., "Structural and Functional Analyses of Benzamidine-based Inhibitors in Complex with Trypsin: Implications for the Inhibition of Factor Xa, tPA, and Urokinase." *J. Med. Chem.* 41:5445-5456 (1998).

Reuning et al., "Multifunctional Potential of the Plasminogen Activation System in Tumor Invasion and Metastasis (Review)," *Int. J. Oncol.* 13:893-906 (1998).

Rittle et al., "Unexpected Enhancement of Thrombin Inhibitor Potency with o-Aminoalkylbenzylamides in the P1 Position," *Bioorg. Med. Chem. Lett.* 13:3477-3482 (2003).

Robinson et al., "Chapter 9. Anticoagulants: Inhibitors of the Factor VIIa/Tissue Factor Pathway," *Ann. Rep. Med. Chem.* 37:85-94 (2002).

Rubini et al., "Synthesis of Isosteric Methylene-oxy Pseudopeptide Analogues as Novel Amide Bond Surrogate Units." *Tetrahedron* 43(21):6039-6045 (1986).

Ruppert et al., "Selective Inhibition of Large-to-Small Surfactant Aggregate Conversion by Serine Protease Inhibitors of the bis-Benzamidine Type," *Am. J. Respir. Cell Mol. Biol.* 28:95-102 (2003).

Sanders and Seto, "4-Heterocyclohexanone-Based Inhibitors of the Serine Protease Plasmin," *J. Med. Chem.* 42:2969-2976 (1999).

Sato et al., "Antithrombotic Effects of YM-60828, a Newly Synthesized Factor Xa Inhibitor, in Rat Thrombosis Models and Its Effects on Bleeding Time," *Br. J. Pharmacol.* 123:92-96 (1998).

Sato et al., "YM-60828, a Novel Factor Xa Inhibitor: Separation of Its Antithrombotic Effects from Its Prolongation of Bleeding Time," *Eur. J. Pharmacol.* 339:141-146 (1997).

Satoh et al., "Medicinal Chemical Studies on Synthetic Protease Inhibitors, Trans-4-Guanidinomethylcyclohexanecarboxylic Acid Aryl Esters," *Chem. Pharm. Bull.* 33:647-654 (1985).

Schechter et al., "On the Size of the Active Site in Proteases. I. Papain," *Biochem. Biophys. Res. Commun.* 27:157-162 (1967).

Schmaier, "The Plasma Kallikrein-Kinin System Counterbalances the Renin-Angiotensin System," *J. Clin. Invest.* 109:1007-1009 (2002).

Schmitt et al., "Clinical Impact of the Plasminogen Activation System in Tumor Invasion and Metastasis: Prognostic Relevance and Target for Therapy," *Thrombosis and Haemostasis* 78:285-296 (1997).

Schweinitz et al., "Design of Novel and Selective Inhibitors of Urokinase-Type Plasminogen Activator with Improved Pharmacokinetic Properties for Use as Antimetastatic Agents," *J. Biol. Chem*, 279:33613-33622 (2004).

Sedrakyan et al., "Effect of Aprotinin on Clinical Outcomes in Coronary Artery Bypass Graft Surgery: A Systematic Review and Meta-Analysis of Randomized Clinical Trials," *J. Thorac. Cardiovasc. Surg.* 128:442-448 (2004).

Shi et al., "Identification and Characterization of a Novel Matrix-degrading Protease from Hormone-dependent Human Breast Cancer Cells," *Cancer Res.* 53:1409-1415 (1993).

Silverberg et al., "Enzymatic Activities of Activated and Zymogen Forms of Human Hageman Factor (Factor XII)," *Blood* 60:64-70 (1982).

Sodha et al., "Aprotinin in Cardiac Surgery," *Expert Rev. Cardiovasc. Ther.* 4:151-160 (2006).

Soll et al., "Amidinohydrazones as Guanidine Bioisosteres: Application to a New Class of Potent, Selective and Orally Bioavailable, Non-Amide-Based Small-Molecule Thrombin Inhibitors," *Bioorg. Med. Chem. Lett.* 10:1-4 (2000).

Sperl et al., "(4-Aminomethyl) Phenylguanidine Derivates as Nonpeptidic Highly Selective Inhibitors of Human Urokinase," *Proc. Natl. Acad. Sci. USA* 97:5113-5118 (2000).

Sperl et al., "Urethanyl-3-Amidinophenylalanine Derivatives as Inhibitors of Factor Xa. X-Ray Crystal Structure of a Trypsin/Inhibitor Complex and Modeling Studies," *Biol. Chem.* 381:321-329 (2000).

Sperzel et al., "Evaluation of Aprotinin and Tranexamic Acid in Different In Vitro and In Vivo Models of Fibrinolysis, Coagulation and Thrombus Formation," *J. Thromb. Haemost.* 5:2113-2118 (2007).

Stauffer et al., "9-Hydroxyazafluorenes and Their Use in Thrombin Inhibitors," *J. Med. Chem.* 48: 2282-2293 (2005).

Stephens et al., "The Urokinase Plasminogen Activator System as a Target for Prognostic Studies in Breast Cancer," *Breast Cancer Res. Treat.*, 52:99-111 (1998).

Stürzebecher et al., "3-Amidinophenylalanine-Based Inhibitors of Urokinase," *Bioorg. Med. Chem. Lett* 9:3147-3152 (1999).

Stürzebecher et al., "Cyclic Amides of Nα-Arylsulfonylaminoacylated 4-Amidinophenylalanine—Tight Binding Inhibitors of Thrombin," *Thrombosis Res.* 29:635-642 (1983).

Stürzebecher et al., "Inhibition of Human Mast Cell Tryptase by Benzamidine Derivatives," *Biol. Chem. Hoppe Seyler* 373:1025-1030 (1992).

Stürzebecher et al., "Novel Plasma Kallikrein Inhibitors of the Benzamidine Type," *Brazilian J. Med. Biol. Res.* 27:1929-1934 (1994).

Stürzebecher et al., "Structure-Activity Relationships of Inhibitors Derived from 3-Amidinophenylalanine," *J. Enzyme Inhibition* 9:87-99 (1995).

Stürzebecher et al., "Synthesis and Structure-Activity Relationships of Potent Thrombin Inhibitors: Piperazides of 3-Amidinophenylalanine," *J. Med. Chem.* 40:3091-3099 (1997).

Stürzebecher et al., "Synthetic Inhibitors of Bovine Factor Xa and Thrombin Comparison of Their Anticoagulant Efficiency," *Thromb. Res.* 54:245-252 (1989).

Stürzebecher et al., "Chemische Beeinflussung der Wechselwirkungen Zwischen Plamakallikrein und Anderen Serinoproteinasen des Blutes," *Zentralbl. Pharm. Pharmakother. Lab. Diagn.* 122:240-241 (1983) (German Language Only).

Sucker et al., Phamazeutische Technologie, Bauer, Georg Thieme Verlag, Stuttgart, (1991) (German Language Only).

Tada et al., "Isolation of Plasma Kallikrein by High Efficiency Affinity Chromatography and Its Characterization," *Biol. Pharm. Bull.* 24:520-524 (2001).

Takeuchi et al., "Reverse Biochemistry: Use of Macromolecular Protease Inhibitors to Dissect Complex Biological Processes and Identify a Membrane-type Serine Protease in Epithelial Cancer and Normal Tissue," *Proc. Natl. Acad. Sci. USA* 96:11054-11061 (1999).

Takeuchi et al., "Cellular Localization of Membrane-type Serine Protease 1 and Identification of Protease-activated Receptor-2 and Single-chain Urokinase-type Plasminogen Activator as Substrates," *J. Biol. Chem.* 275:26333-26342 (2000).

Tamura et al., "Synthesis and Biological Activity of Peptidyl Aldehyde Urokinase Inhibitors." *Bioorganic & Medicinal Chemistry Letters*, 10:983-987 (2000).

Teno et al., "Development of Selective Inhibitors against Plasma Kallikrein," *Chem. Pharm. Bull.* 39:2930-2936 (1991).

Towle et al., "Inhibition of Urokinase by 4-Substituted Benzo[b]thiophene-2-Carboxamidines: An Important New Class of Selective Synthetic Urokinase Inhibitor," *Cancer Research* 53:2553-2559 (1993).

Tsuda et al., "Structure-Inhibitory Activity Relationship of Plasmin and Plasma Kallikrein Inhibitors," *Chem. Pharm. Bull.* 49:1457-1463 (2001).

Tucker et al., "Potent Noncovalent Thrombin Inhibitors That Utilize the Unique Amino Acid d-Dicyclohexylalanine in the P3 Position. Implications on Oral Bioavailability and Antithrombotic Efficacy," *J. Med. Chem.* 40:1565-1569 (1997).

Tucker et al., "Synthesis of a Series of Potent and Orally Bioavailable Thrombin Inhibitors That Utilize 3,3-Disubstituted Propionic Acid Derivatives in the $P_3$ Position," *J. Med. Chem.* 40:3687-3693 (1997).

Vassalli et al., "Amiloride Selectively Inhibits the Urokinase-Type Plasminogen Activator," *FEBS Lett.* 214:187-191 (1987).

von der Saal et al, "Derivatives of 4-Amino-Pyridine as Selective Thrombin Inhibitors," *Bioorganic & Medicinal Chemistry Letters* 7:1283-1288 (1997).

Wachtfogel et al., "Aprotinin Inhibits the Contact, Neutrophil, and Platelet Activation Systems During Simulated Extracorporeal Perfusion," *J. Thorac. Cardiovasc. Surg.* 106:1-10 (1993).

Wagner et al., "Synthese von N-[Amidinobenzyl]-und N-[Amidinophenyl]-Phthalimide und-1-0xoisoindoline," *Pharmazie* 32:76-79 (1977) (German Language Only).

Weitz, "New Anticoagulants for Treatment of Venous Thromboembolism," *Circulation*, 110 (9 Suppl. 1):1-19-26 (2004).

Weitz, "Activation of Blood Coagulation by Plaque Rupture: Mechanisms and Prevention," *Am. J. Cardiol.* 75:18B-22B (1995).

Westaby, "Aprotinin: Twenty-Five Years of Claim and Counterclaim," *J. Thorac. Cardiovasc. Surg.* 135:487-491 (2008).

Wikström et al., "Development and Validation of a Chiral Capillary Electrophoresis Method for Melagatran and Ximelagatran Drug Substances," *J. Sep. Sci.* 25:1167-1174 (2002).

Xue and Seto, "Selective Inhibitors of the Serine Protease Plasmin: Probing the S3 and S3' Subsites Using a Combinatorial Library," *J. Med. Chem.* 48:6908-6917 (2005).

Zeslawska et al., "Crystals of the Urokinase Type Plasminogen Activator Variant βc-uPA in Complex with Small Molecule Inhibitors Open the Way Towards Structure-based Drug Design," *J. Mol. Biol.* 301:465-475 (2000).

Zeslawska et al., "Crystals of Urokinase Type Plasminogen Activator Complexes Reveal the Binding Mode of Peptidomimetic Inhibitors," *J. Mol.Biol.* 328:109-118 (2003).

Zhang et al., "Assignment 1 of Human Putative Tumor Suppressor Genes ST13 (alias SNC6) and ST14 (alias SNC19) to Human Chromosome Bands 22q13 and 11q24→q25 by In Situ Hybridization," *Cytogenet. Cell Genet.* 83:56-57 (1998).

Zhu et al., "Recent Advances in Inhibitors of Factor Xa in the Prothrombinase Complex," *Curr. Opin. Cardiovasc. Pulmon. Renal Invest. Drugs* 1:63-87 (1999).

Zufferey et al., "Do Antifibrinolytics Reduce Allogeneic Blood Transfusion in Orthopedic Surgery?" *Anesthesiology* 105:1034-1046 (2006).

Extended European Search Report pertaining to European Patent Application No. 10013065.7-2123.

Office Action pertaining to U.S. Appl. 10/297,557 mailed Nov. 4, 2003.

Office Action pertaining to U.S. Appl. No. 10/311,364 mailed Nov. 19, 2003.

Office Action pertaining to U.S. Appl. No. 10/311,364 mailed Apr. 1, 2004.

Office Action pertaining to U.S. Appl. No. 10/506,579 mailed Dec. 16, 2009.

Office Action pertaining to U.S. Appl. No. 10/506,579 mailed Jan. 30, 2009.

Office Action pertaining to U.S. Appl. No. 10/506,579 mailed Jul. 17, 2008.

Office Action pertaining to U.S. Appl. No. 10/540,958, mailed Nov. 17, 2008.

Office Action pertaining to U.S. Appl. No. 10/540,958, mailed Jun. 11, 2009.

Office Action pertaining to U.S. Appl. No. 10/555,821, mailed Jan. 21, 2009.

Office Action pertaining to U.S. Appl. No. 10/571,026, mailed Dec. 13, 2007.

Office Action pertaining to U.S. Appl. No. 10/571,026, mailed Feb. 23, 2009.

Office Action pertaining to U.S. Appl. No. 10/571,026, mailed Oct. 30, 2009.

English Translation of the International Preliminary Report on Patentability for International Application No. PCT/EP2007/009220, dated May 5, 2009.

English Translation of the Written Opinion of the International Search Authority for International Application No. PCT/EP2007/009220, completed Feb. 13, 2008.

International Search Report for International Application No. PCT/EP2007/009220, dated Feb. 13, 2008.

\* cited by examiner

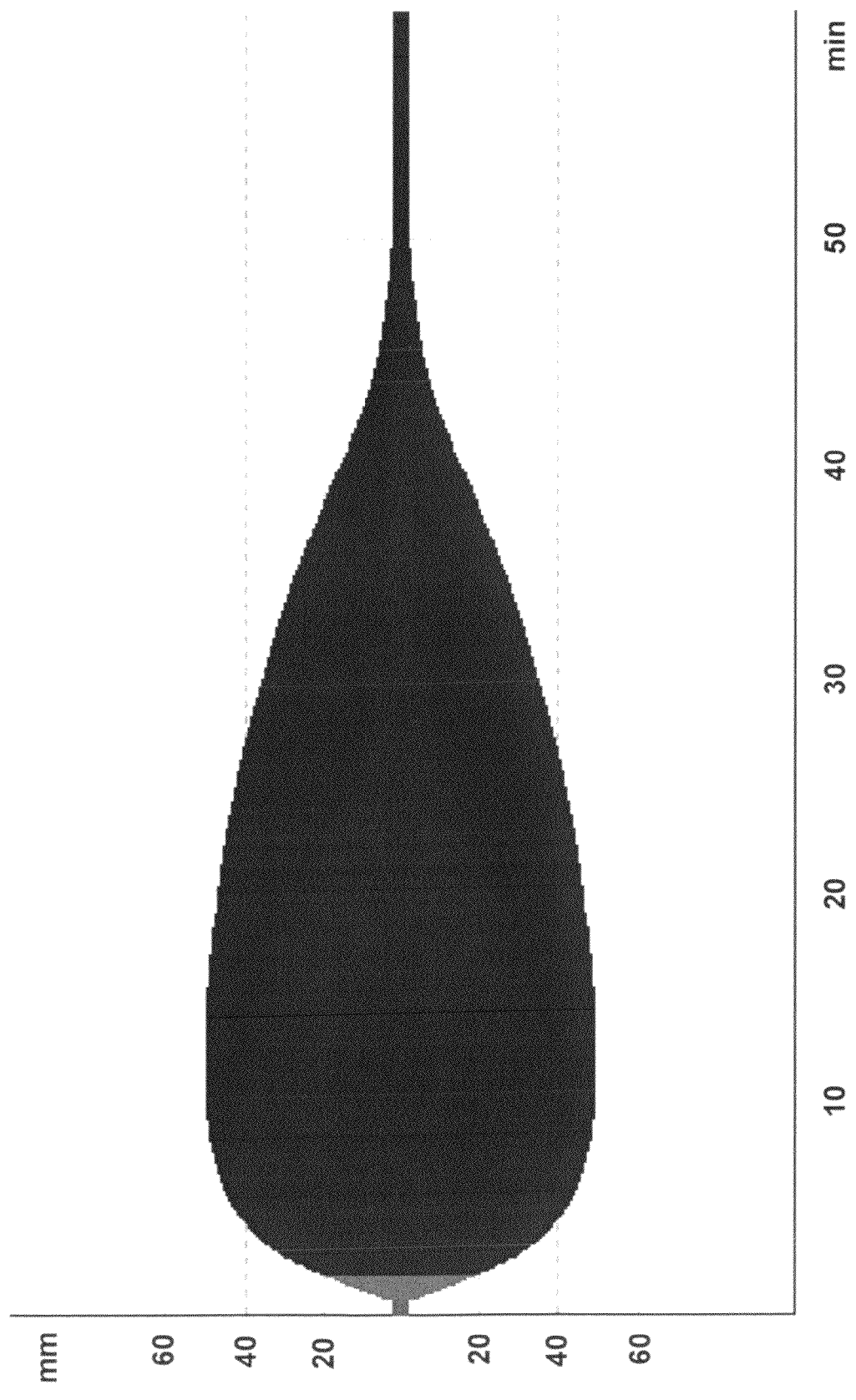

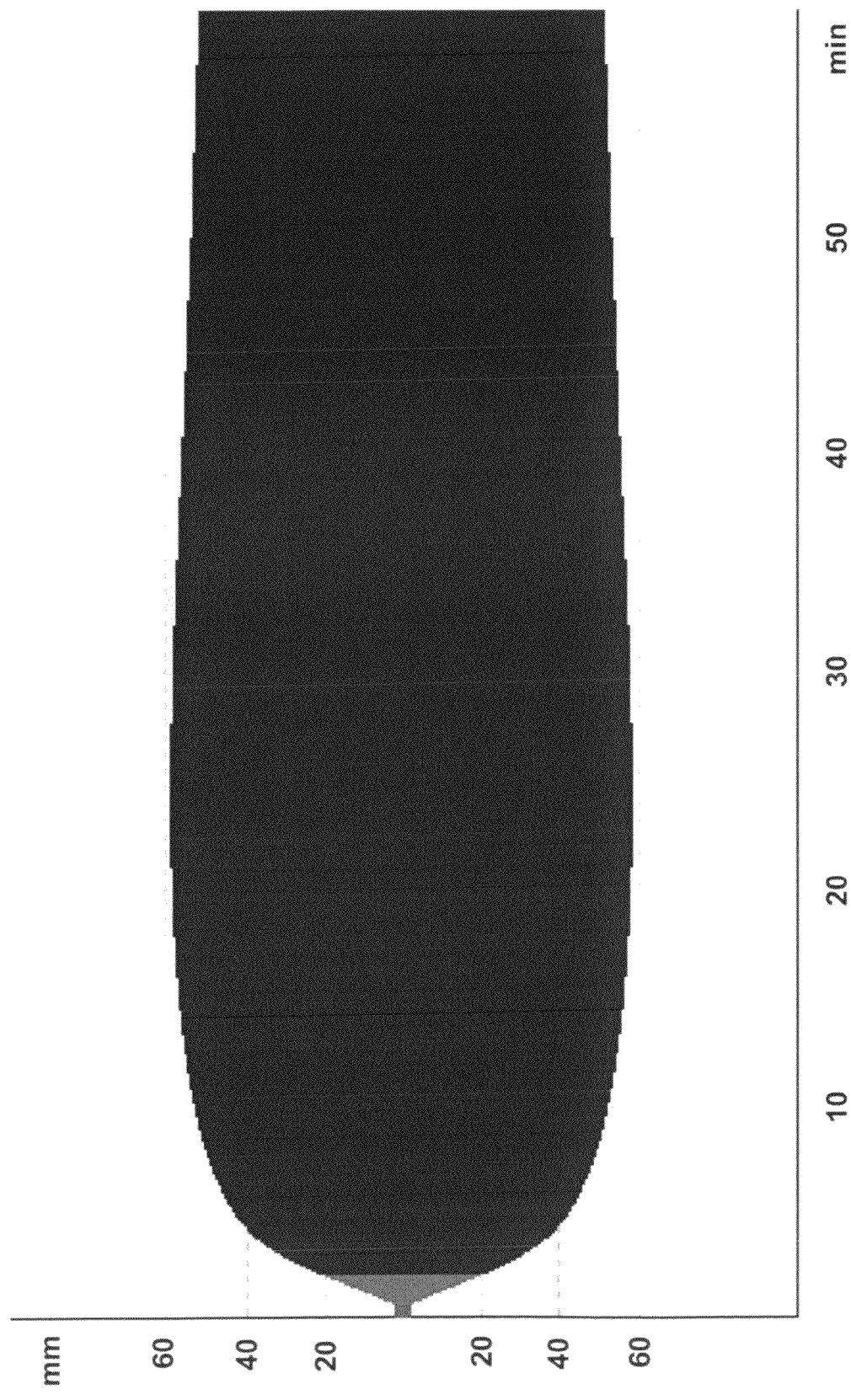

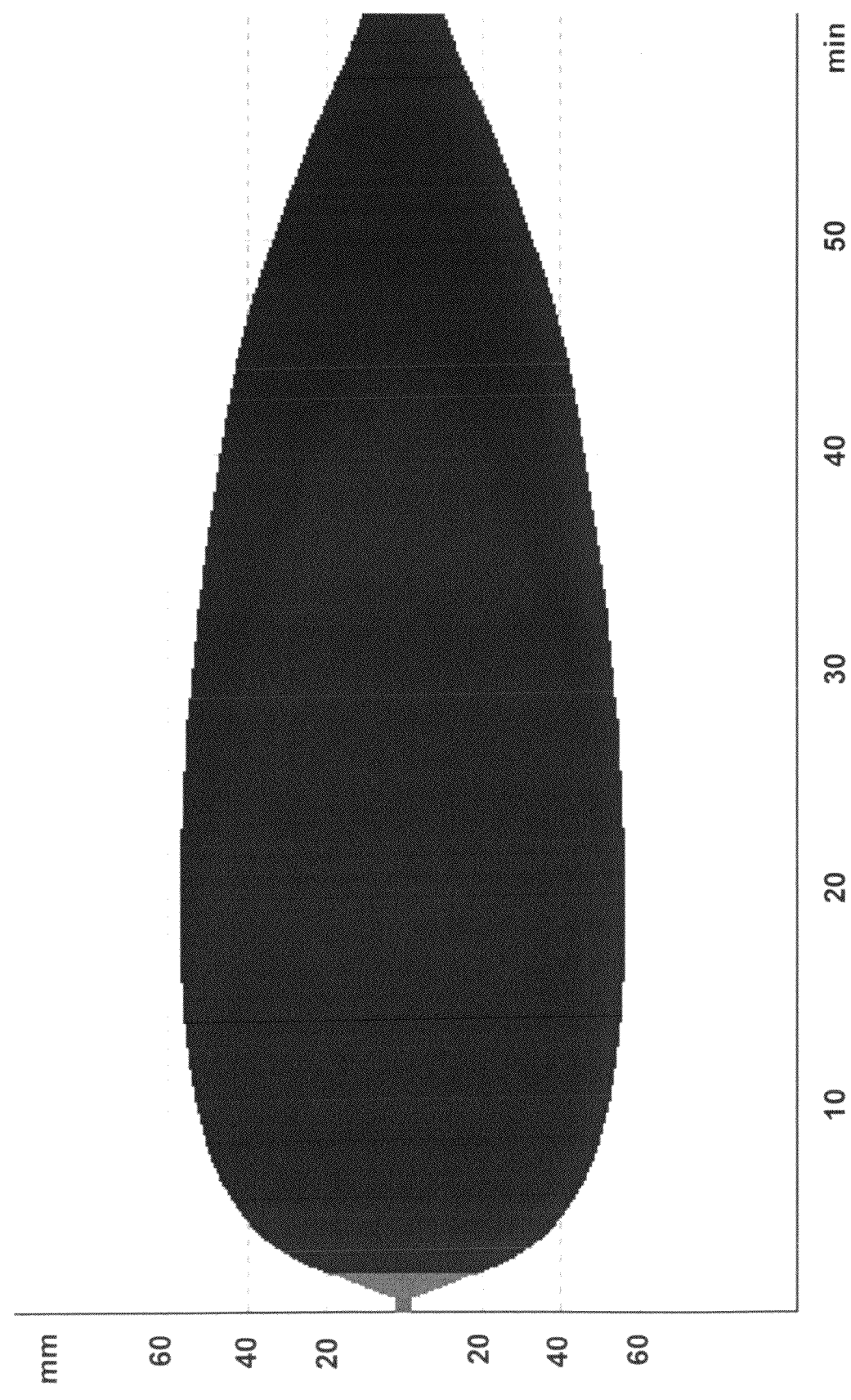

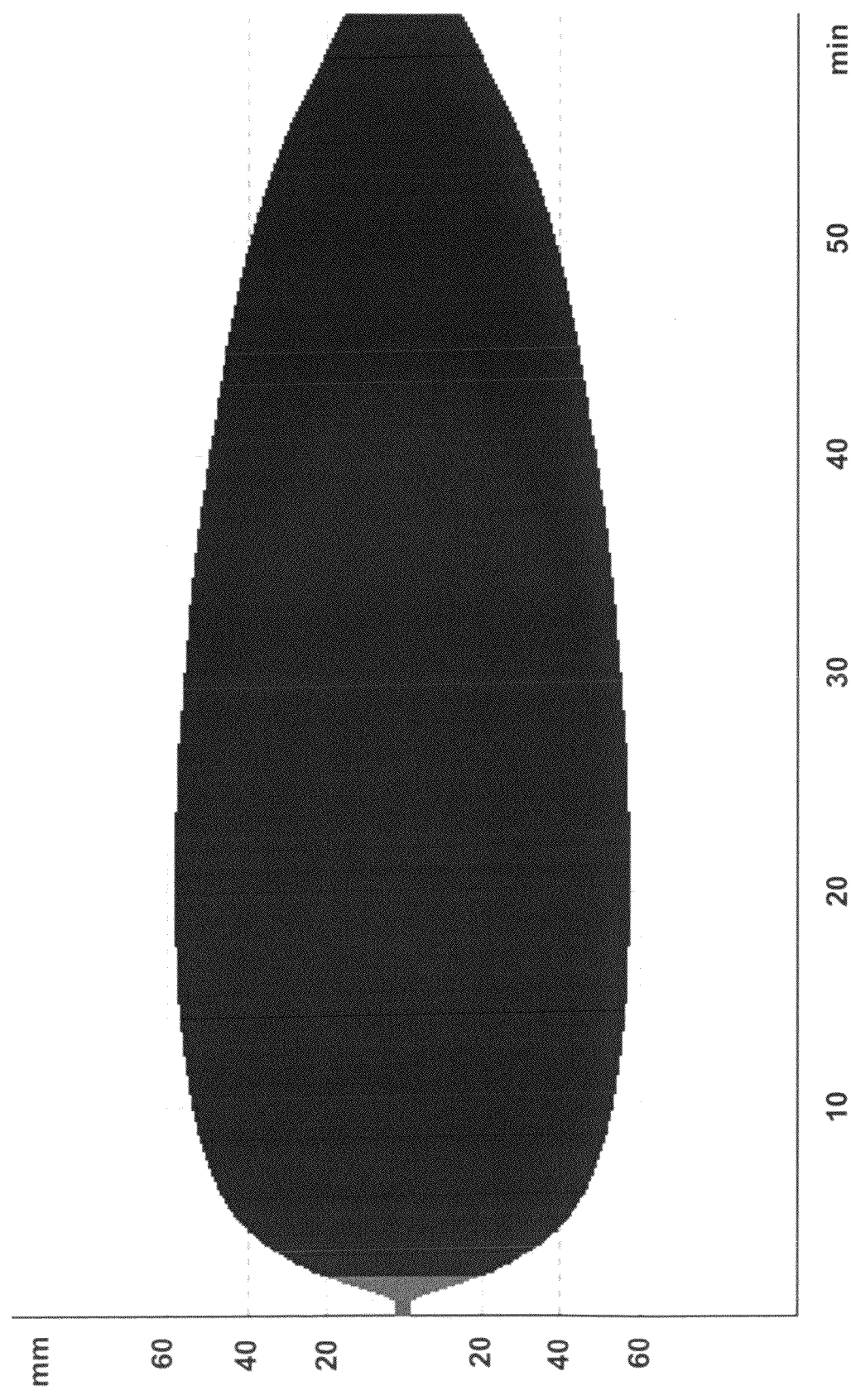

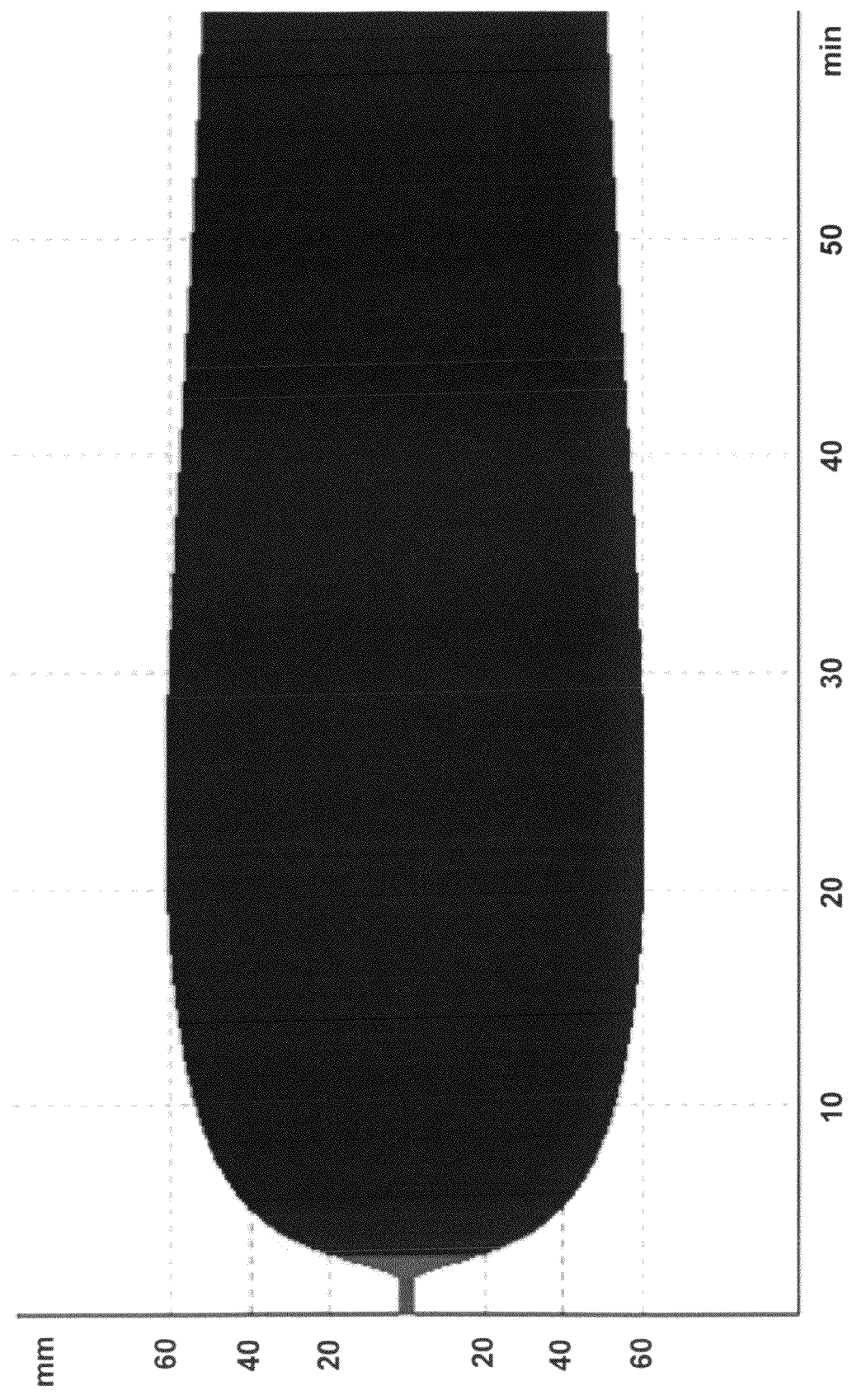
Fig. 1E: Compound No. 3 (600 nM)

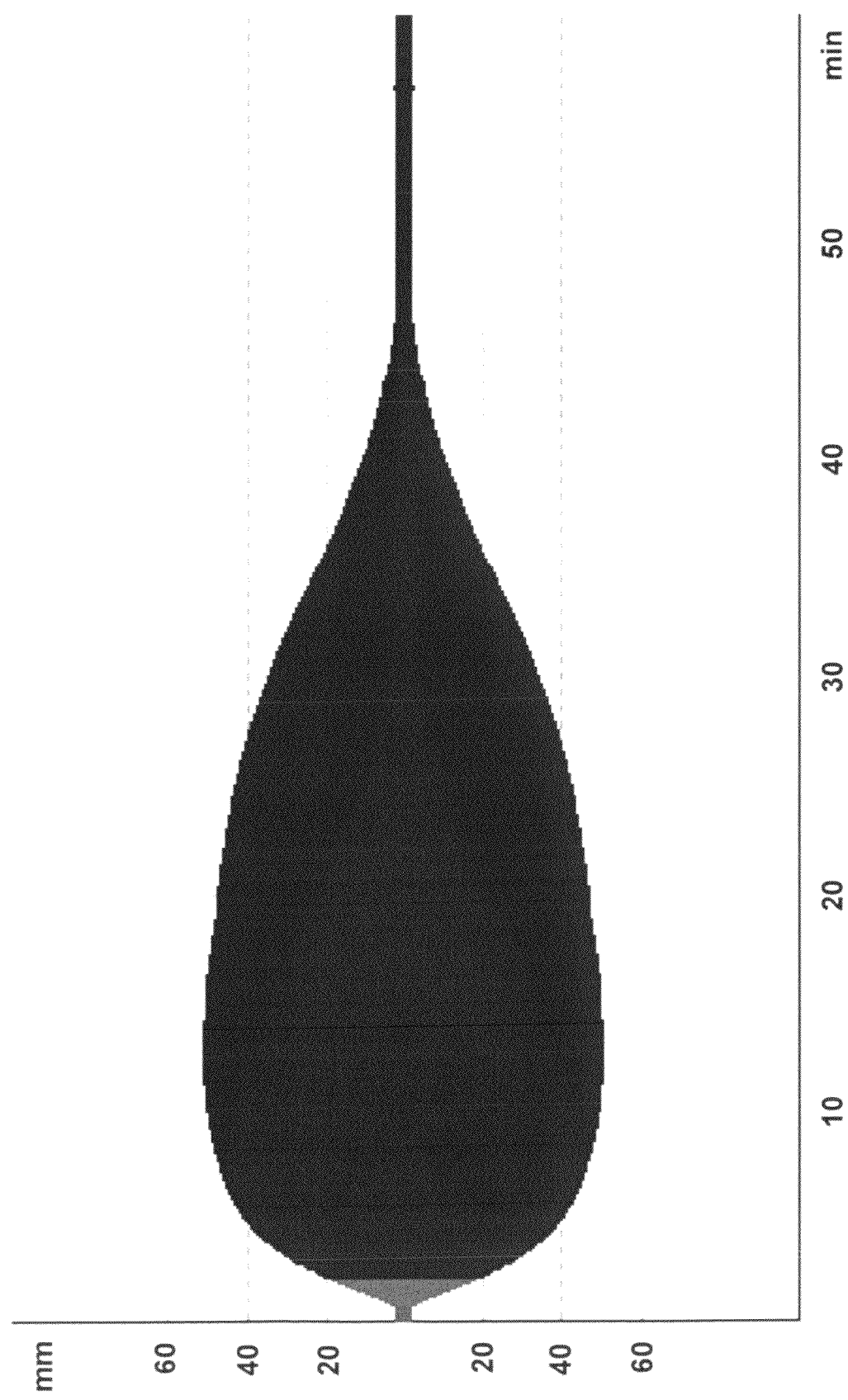
Fig. 1F: Aprotinin (60 nM)

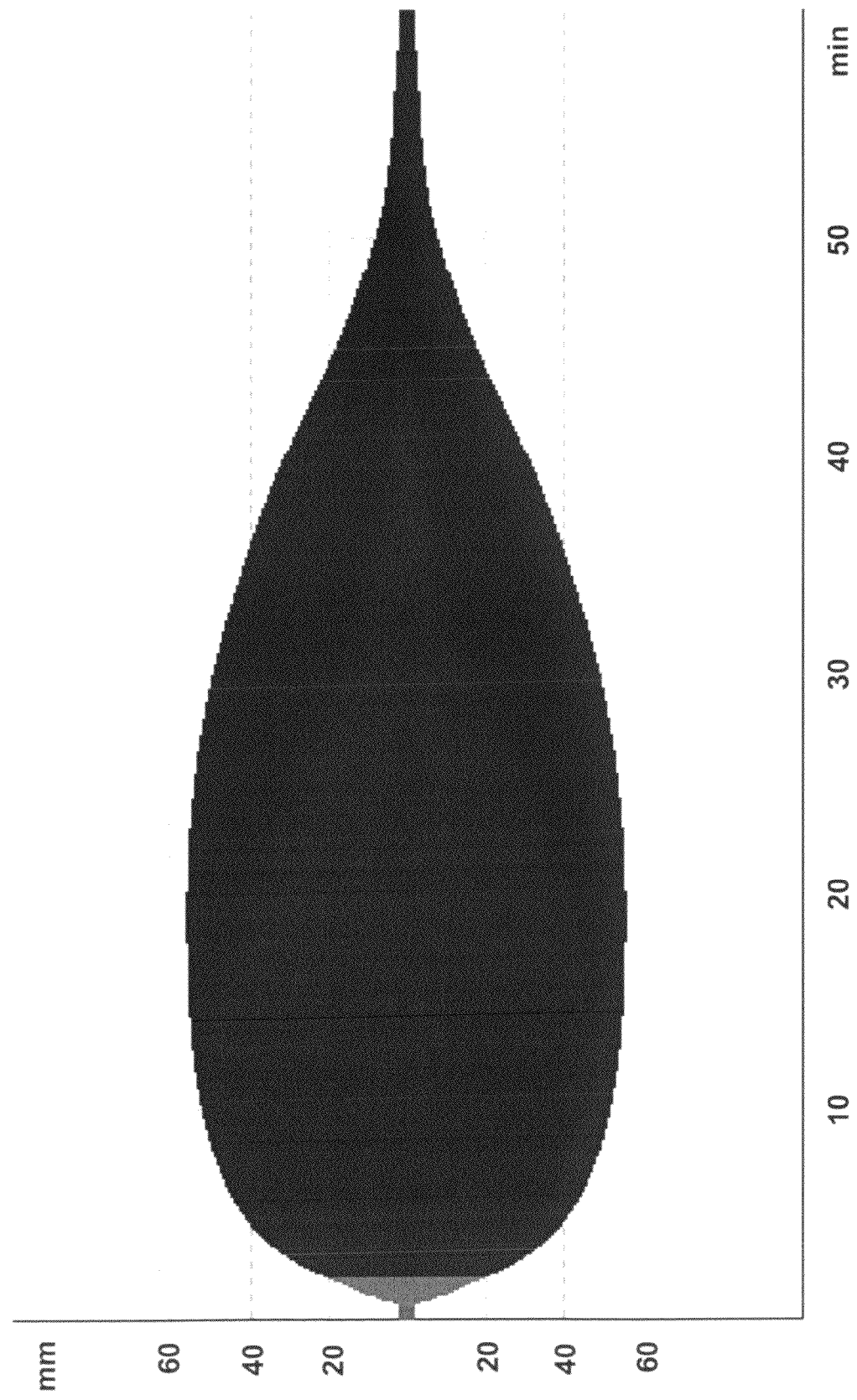
Fig. 1G: Aprotinin (200 nM)

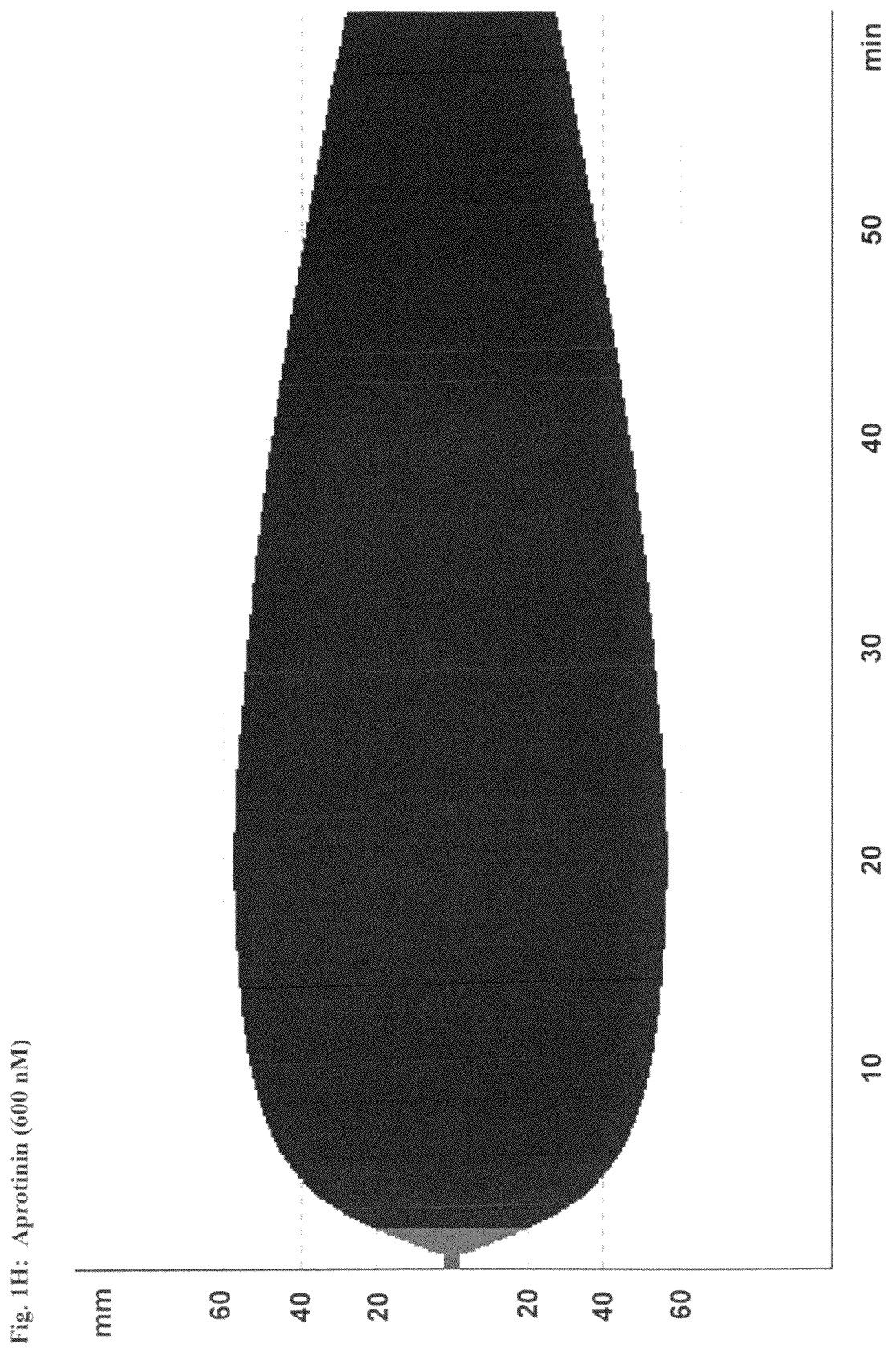
Fig. 1H: Aprotinin (600 nM)

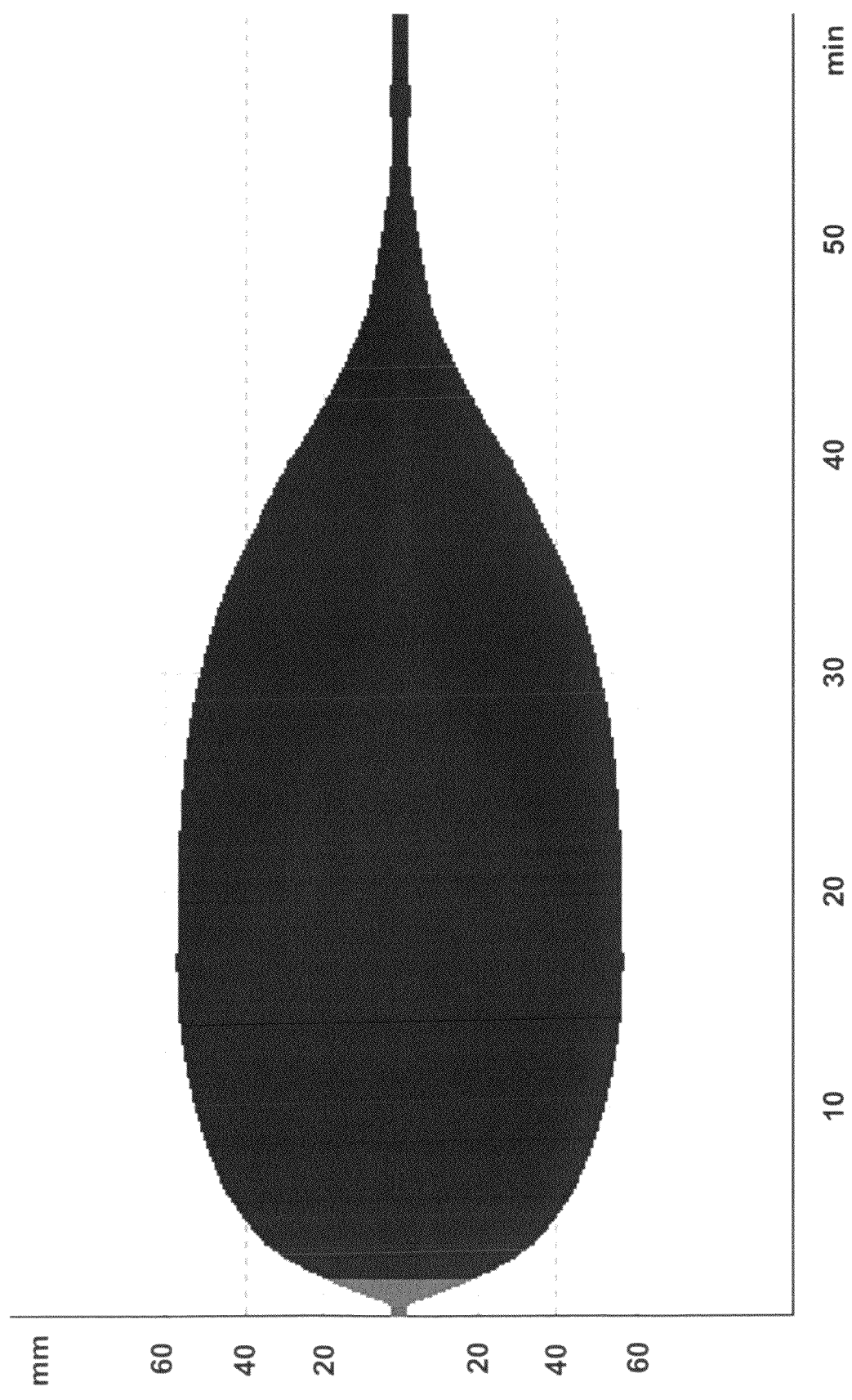

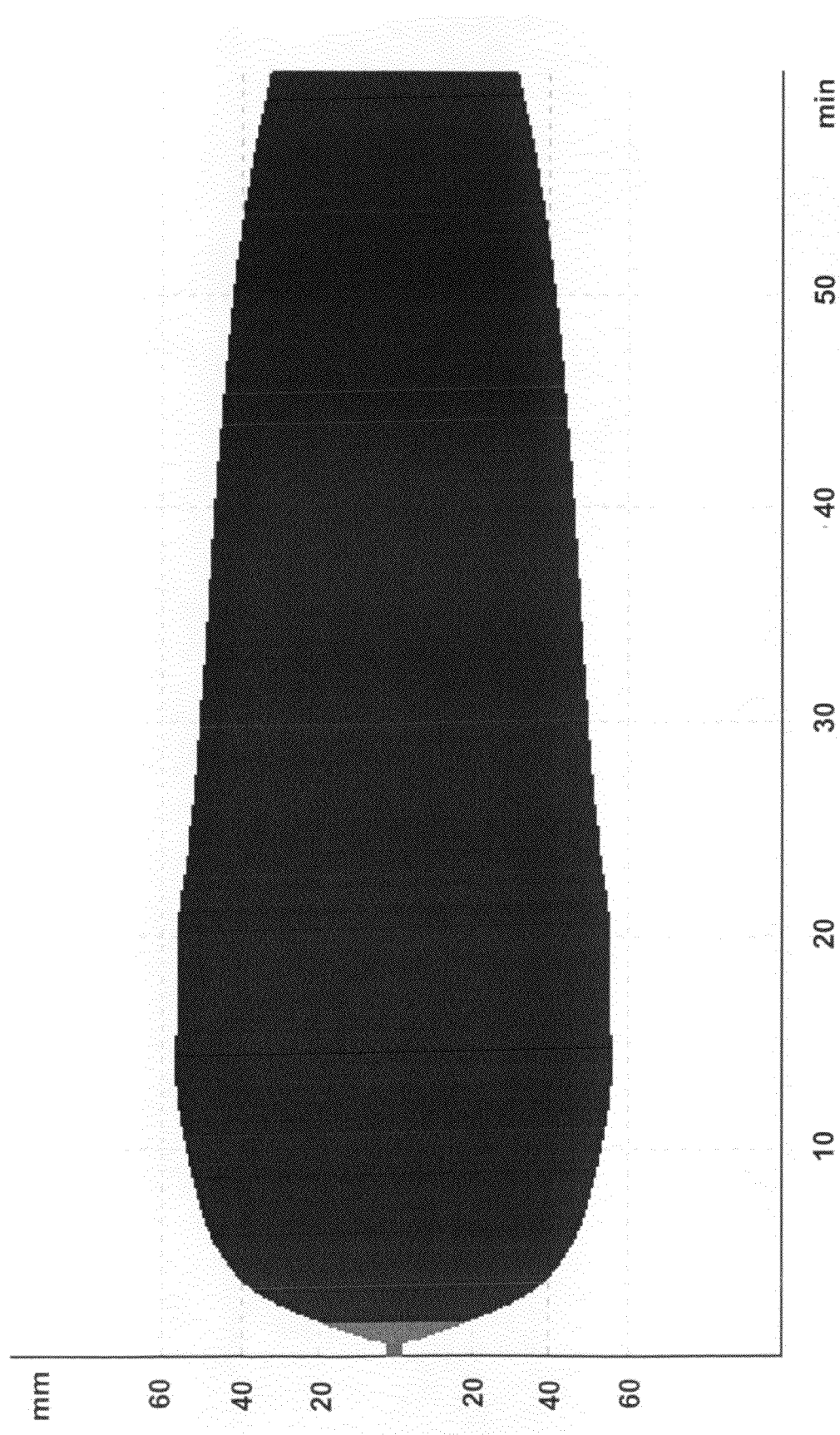

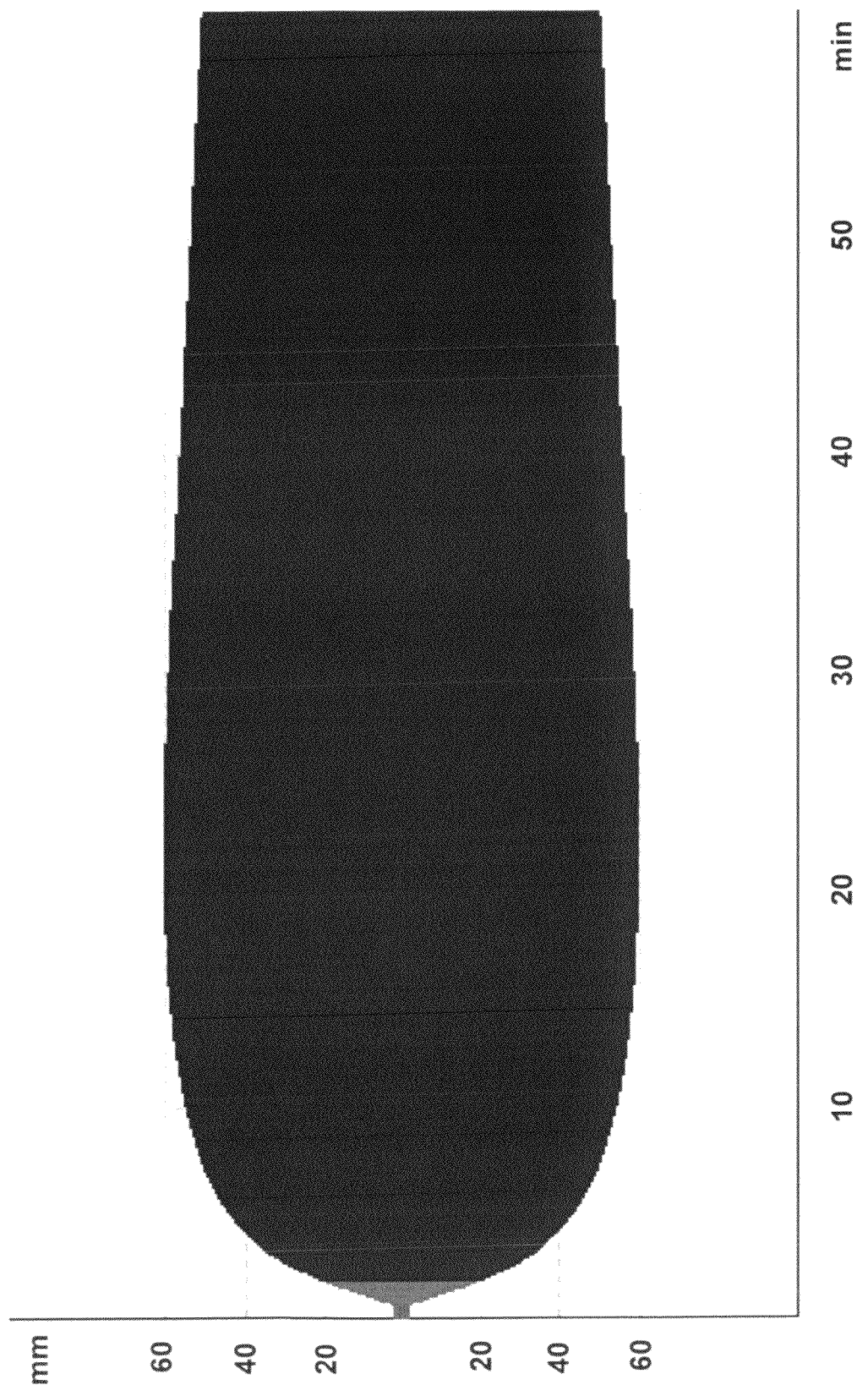
Fig. 1K: Tranexamic Acid (10000 nM)

Fig. 3

|  |  | Plasma clotting times | | Whole blood clotting times (ROTEM®) | | | Extrinsic thrombin generation | | | Intrinsic thrombin generation | | |
|---|---|---|---|---|---|---|---|---|---|---|---|---|
|  |  | PT [s] | aPTT [s] | Extrinsic CT [s] | Intrinsic CT [s] | Lag phase [min] | Peak thrombin [nM] | ETP [nM*min] | Lag phase [min] | Peak thrombin [nM] | ETP [nM*min] |
| control |  | 10.1 (8.4;10.8) | 29.8 (26.8;33.9) | 51 (41;58) | 159 (147;209) | 9.0 (8.0;14.0) | 156 (125;237) | 3304 (2973;3837) | 9.0 (8.0;10.0) | 338 (274;375) | 3444 (2982;3957) |
| Cmpd. No. 3 | 100 nM | 10.0 (9.6;10.3) | 30.3 *# (29.8;30.7) | 53 (49;54) | 188 *# (174;205) | 10.0 * (9.5;10.5) | 142 * (113;169) | 3283 (3171;3845) | 11.0 *# (10.0;12.0) | 296 *# (277;317) | 3475 (3430;3910) |
|  | 300 nM | 10.2 *# (9.8;10.4) | 33.9 *# (33.2;36.3) | 58 *# (55;59) | 243 *# (218;257) | 11.5 *# (10.0;12.0) | 130 * (98;143) | 3215 (3114;3818) | 13.0 *# (12.0;14.0) | 282 *# (243;296) | 3456 (3416;3870) |
|  | 1000 nM | 11.0 *# (10.5;11.2) | 51.6 *# (49.8;54.4) | 82 *# (75;93) | 326 *# (293;359) | 16.0 *# (14.0;16.5) | 80 *# (77;111) | 3010 * (2994;3643) | 16.5 *# (16.0;21.0) | 192 *# (192;244) | 3306 * (3209;3684) |
| Aprotinin | 100 nM | 9.9 (9.5;10.1) | 30.8 * (30.3;31.3) | 46 (44;50) | 157 * (151;162) | 9.0 (9.0;10.0) | 134 * (117;150) | 3207 * (3057;3650) | 9.5 (9.0;10.0) | 325 * (295;334) | 3401 * (3362;3818) |
|  | 300 nM | 9.9 (9.5;10.1) | 31.6 * (30.6;31.7) | 47 * (45;49) | 163 (152;163) | 9.0 * (9.0;10.0) | 125 * (117;146) | 3201 * (3075;3651) | 10.0 (9.0;10.0) | 323 * (285;332) | 3449 (3402;3852) |
|  | 1000 nM | 10.0 (9.6;10.2) | 34.7 * (33.8;35.4) | 48 (47;53) | 178 * (167;172) | 9.0 * (9.0;11.0) | 122 * (111;143) | 3200 * (3111;3689) | 10.0 * (10.0;10.5) | 311 (271;324) | 3446 (3413;3870) |

\* $p<0.05$ versus control
\# $p<0.05$ Compound No. 3 versus aprotinin at the same final concentration
PT: Prothrombin time; aPTT: activated partial thromboplastin time; ETP: Endogenous thrombin potential; TGA: Thrombin generation assay, CT: clotting time.

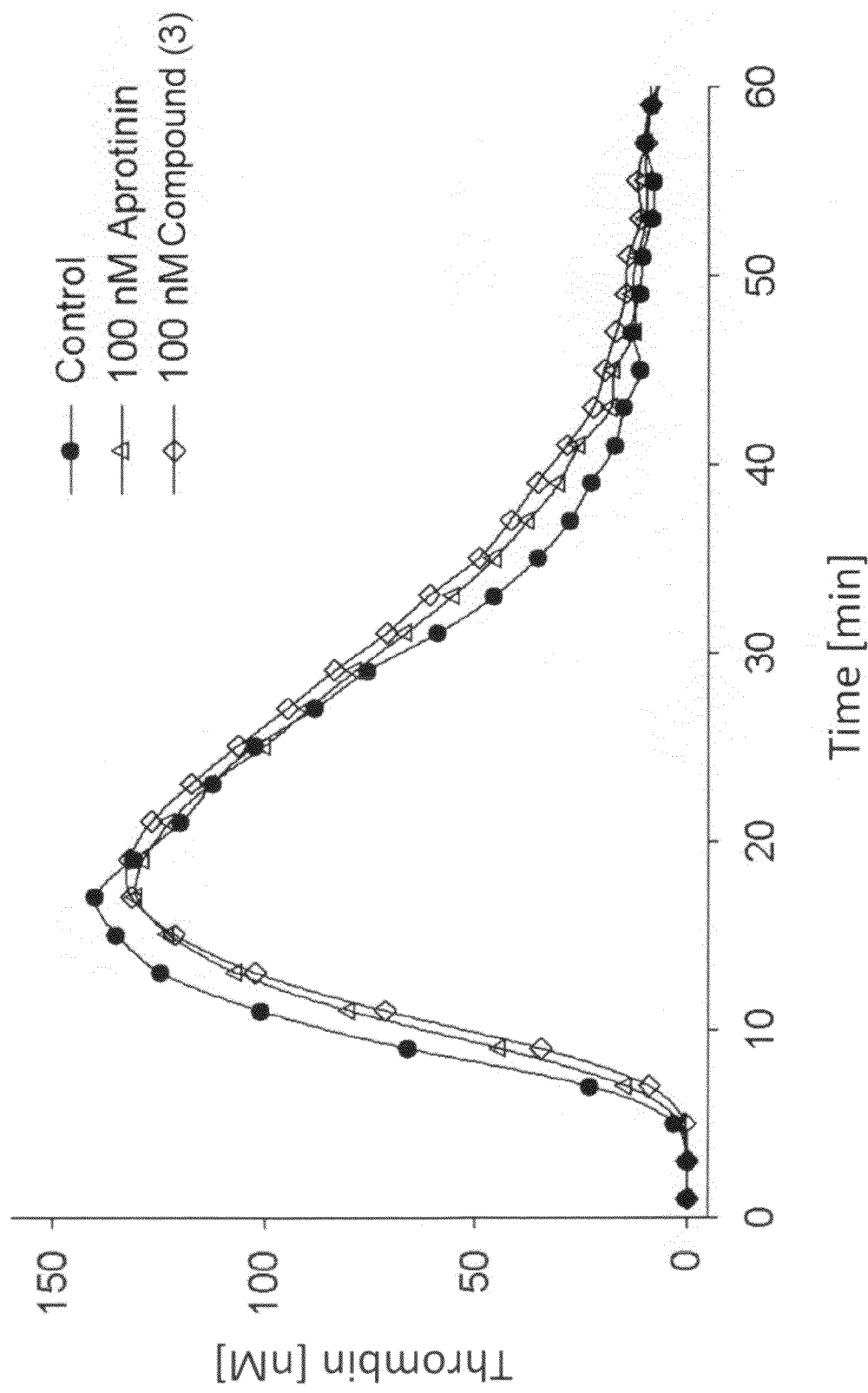
Fig. 4A Extrinsic Activation

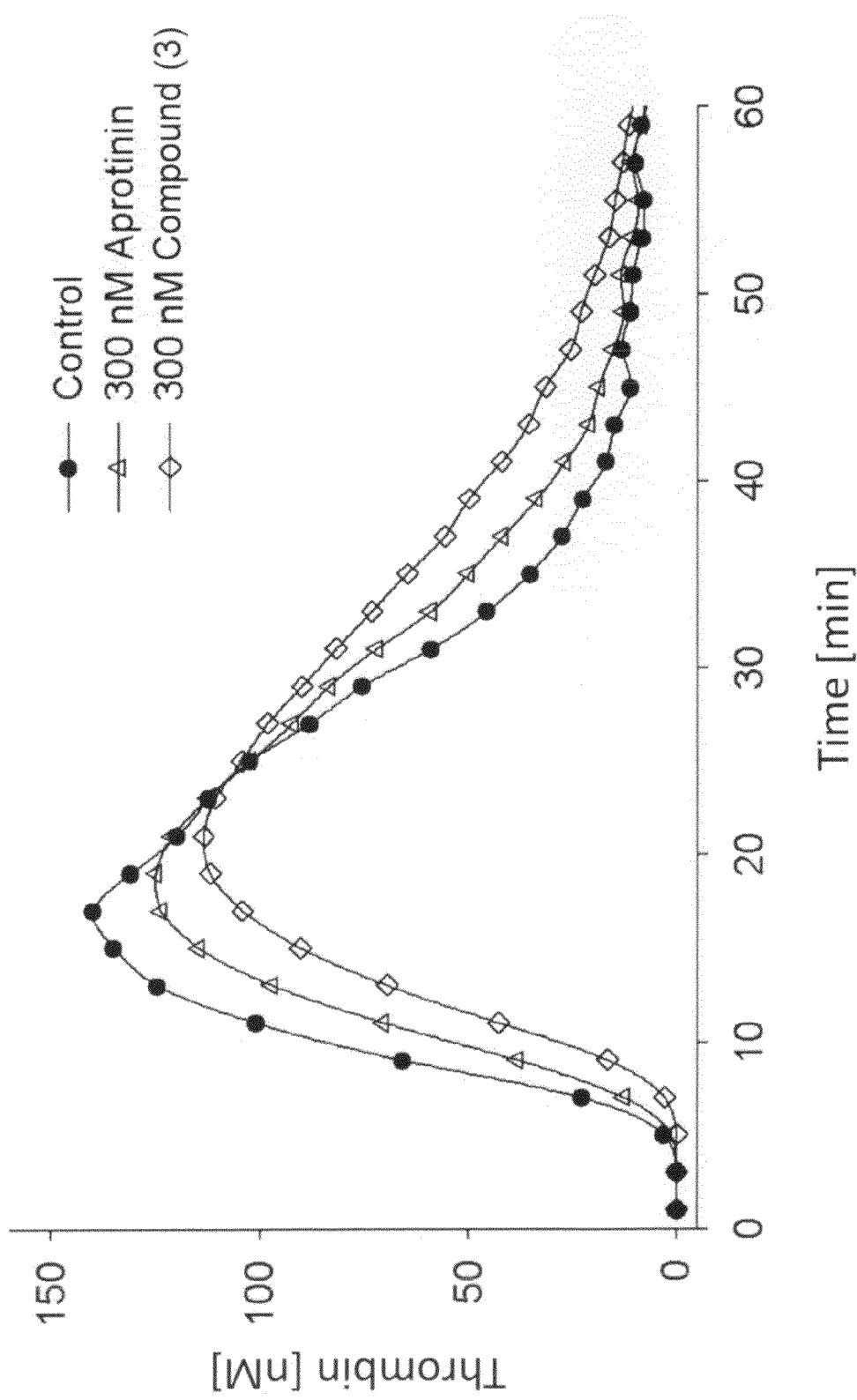
Fig. 4B Extrinsic Activation

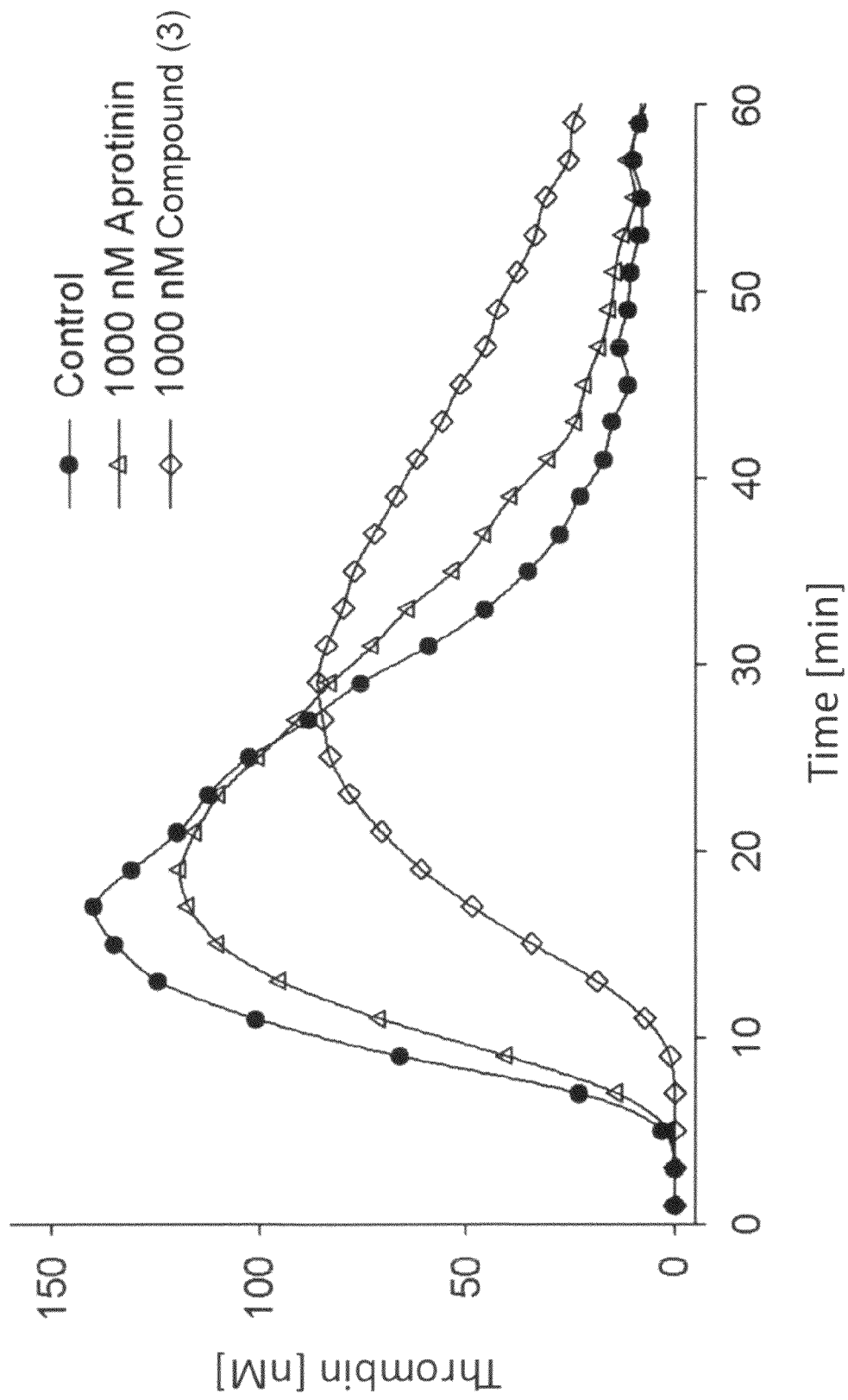
Fig. 4C Extrinsic Activation

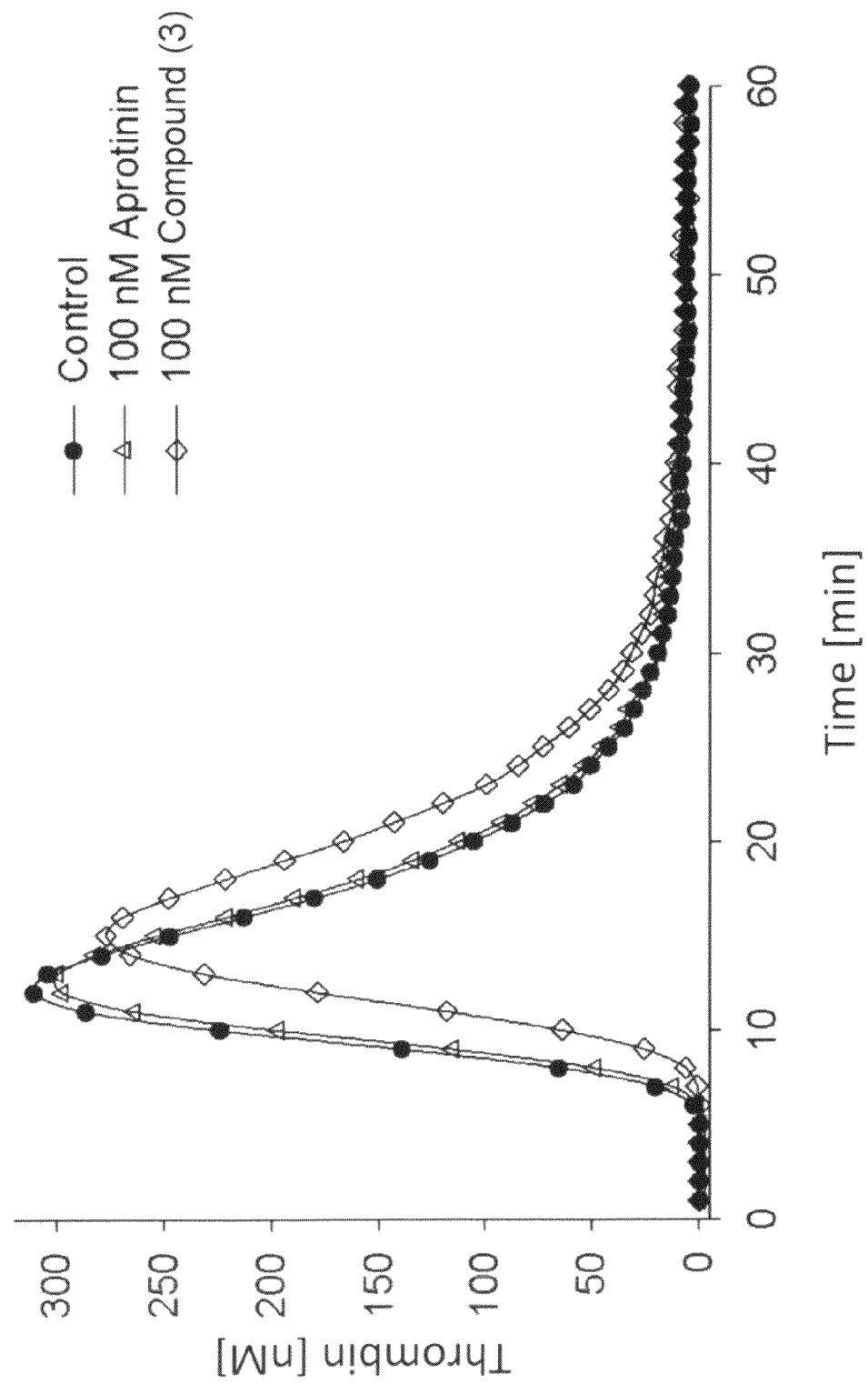
Fig. 4D Intrinsic Activation

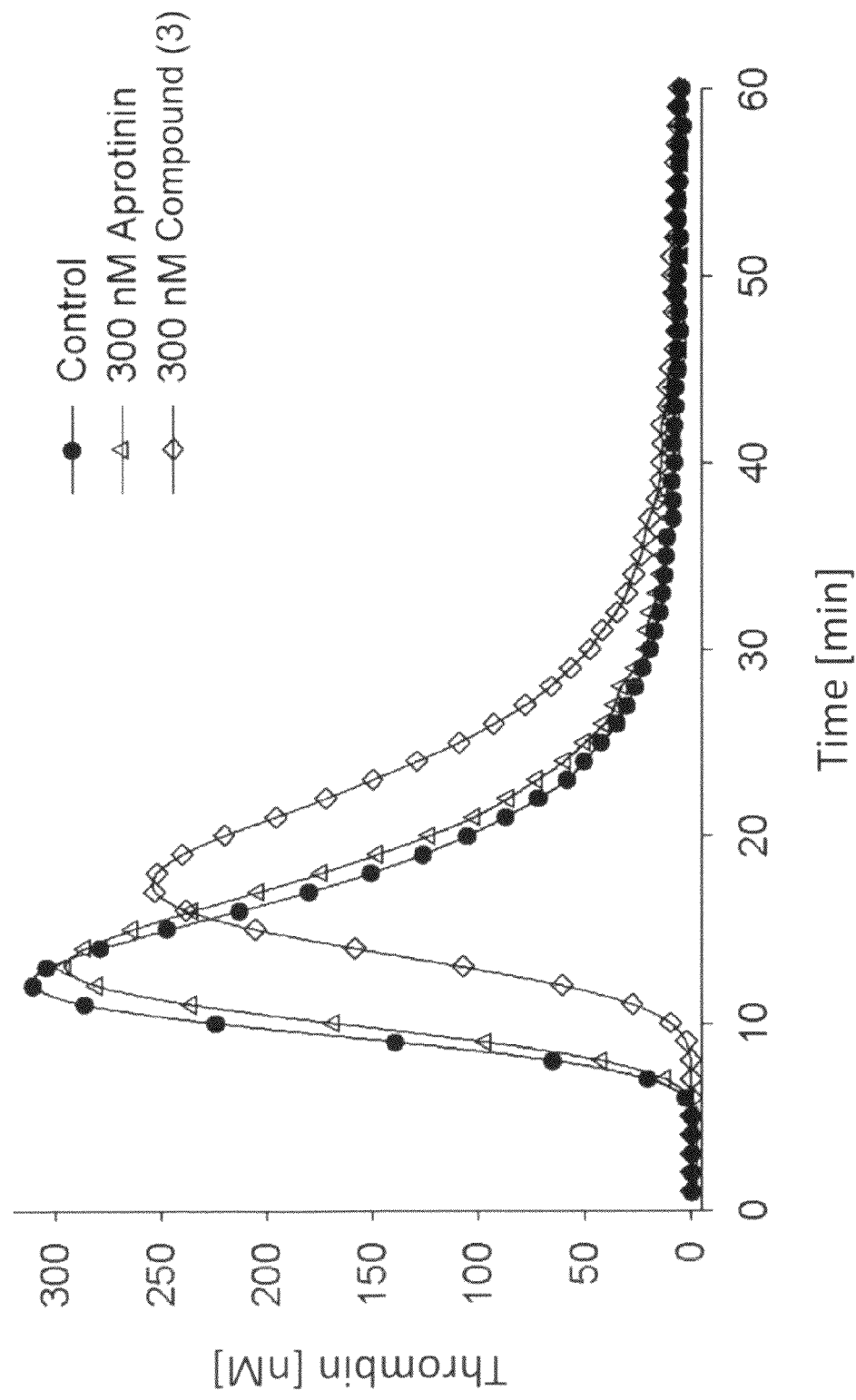
Fig. 4E Intrinsic Activation

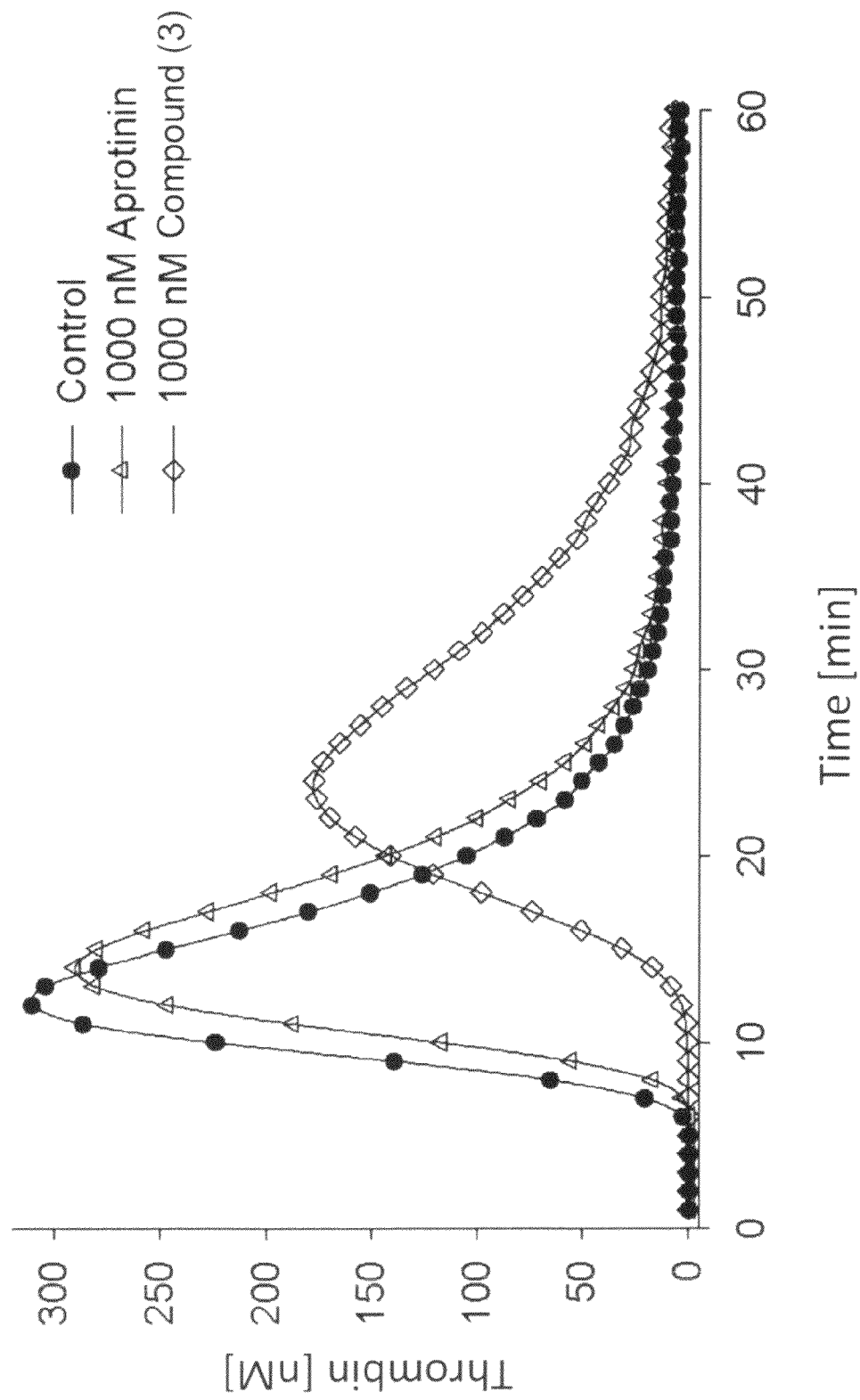
Fig. 4F Intrinsic Activation

TRYPSIN-LIKE SERINE PROTEASE INHIBITORS, AND THEIR PREPARATION AND USE

CROSS-REFERENCE TO RELATED APPLICATIONS

This application is a continuation-in-part of International Application No. PCT/EP2007/009220, filed Oct. 24, 2007, which claims benefit of German Patent Application No. 102006050672.3, filed Oct. 24, 2006. The disclosures of each application are incorporated by reference in their entirety.

BACKGROUND OF THE INVENTION

The invention relates to inhibitors of trypsin-like serine proteases of the general formula

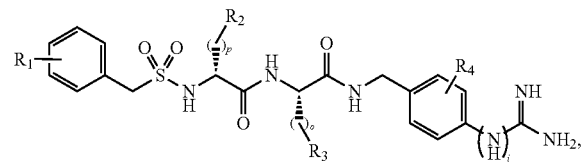

which, besides plasmin, also inhibit plasma kallikrein, and to the preparation and use thereof as medicaments, preferably for the treatment of blood loss, especially in hyperfibrinolytic conditions, in organ transplants or cardiac surgical procedures especially with cardiopulmonary bypass, or as constituent of a fibrin adhesive.

Inhibitors of plasmin and plasma kallikrein (PK) have been disclosed. Plasmin is a trypsin-like serine protease and cleaves numerous substrates C-terminally of the basic amino acids arginine or lysine. Plasmin is formed from the zymogen plasminogen by the catalytic action of the plasminogen activators urokinase or tPA. Plasmin substrates include various proteins of the extracellular matrix and basal membrane, for example fibronectin, laminin, type IV collagen or fibrin, but also numerous zymogens such as proforms of the matrix metalloproteases or of the plasminogen activator urokinase. In blood, plasmin is responsible in particular for fibrinolysis by cleaving fibrin into soluble products.

The endogenous plasmin inhibitors include α2-macroglobulin and the serpin α2-antiplasmin. Under certain pathological conditions there may be spontaneous activation of fibrinolysis. In the event of such a hyperplasminemia, not only is the wound-closing fibrin degraded, but there is also formation of anticoagulant fibrinogen degradation products. Serious impairments of hemostasis may arise thereby. Antifibrinolytics used clinically are synthetic amino carboxylic acids such as ε-aminocaproic acid, p-aminomethylbenzoic acid or tranexamic acid (trans-4-(aminomethyl)cyclo-hexanecarboxylic acid). These compounds block the binding of the zymogen plasminogen to fibrin and thus inhibit activation thereof to plasmin. These compounds are therefore not direct inhibitors of plasmin and are unable to inhibit plasmin which has already been formed. A further antifibrinolytic employed is aprotinin (Trasylol®, Bayer AG, Leverkusen), a polypeptide of 58 amino acids which is obtained from bovine lung. Aprotinin inhibits plasmin with an inhibition constant of 1 nM, but is relatively nonspecific and also effectively inhibits trypsin ($K_i$=0.1 nM) and plasma kallikrein ($K_i$=30 nM). Aprotinin also inhibits other enzymes, although with reduced activity.

A main use of aprotinin serves to reduce blood loss, especially in cardiac surgical procedures with cardiopulmonary bypass (CPB), thus distinctly reducing the need for perioperative blood transfusions (Sodha et al., 2006). In addition, aprotinin is also employed in other operations, for example in organ transplants, to inhibit blood loss, or is used as addition in fibrin adhesives.

The use of aprotinin has several disadvantages. Since it is isolated from bovine organs, there is in principle the risk of pathogenic contamination and allergic reactions. The risk of an anaphylactic shock is relatively low with the first administration of aprotinin (<0.1%), but increases on repeated administration within 200 days to 4-5%.

It was recently reported that administration of aprotinin in direct comparison with ε-aminocaproic acid or tranexamic acid induces an increased number of side effects (Mangano et al., 2006). Administration of aprotinin led to a doubling of the number of cases of kidney damage, making dialysis necessary. Likewise, the risk of myocardial infarction and apoplectic stroke was increased through administration of aprotinin by comparison with the control groups.

To date only a few synthetic inhibitors of plasmin have been disclosed. Sanders and Seto (1999) described 4-heterocyclohexanone derivatives with relatively weak activity, with inhibition constants of ≧50 μM for plasmin. Xue and Seto (2005) reported on peptidic cyclohexanone derivatives with $IC_{50}$ values of ≧2 μM, but further development thereof is unknown. Okada and Tsuda described various derivatives with a 4-aminomethylcyclohexanoyl residue which inhibit plasmin with $IC_{50}$ values of ≧0.1 μM, but clinical use of these inhibitors is not known (Okada et al., 2000; Tsuda et al., 2001).

Inhibition constants for plasmin have been published in numerous publications on the development of inhibitors of coagulation proteases as antithrombotics, where the aim in these cases was to inhibit plasmin as weakly as possible. A possible use of these compounds for reducing blood loss in cardiac surgical procedures was not mentioned in any of these papers. Thus, for example, the thrombin inhibitor melagatran inhibits plasmin with a $K_i$ value of 0.7 μM, whereas the structurally closely related compounds H317/86 has an inhibition constant of 0.22 μM for plasmin (Gustafsson et al., 1998). However, both compounds inhibit the protease thrombin distinctly more strongly with $K_i$ values of ≦2 nM, and thus administration of melagatran results in strong anticoagulation.

As described in the introduction, aprotinin inhibits not only plasmin but also plasma kallikrein (PK). PK is a multifunctional, trypsin-like serine protease for which several physiological substrates are known. Thus, PK is able to release by proteolytic cleavage the vasoactive peptide bradykinin from high molecular weight kininogen and to activate the zymogens coagulation factor XII, pro-urokinase, plasminogen and pro-MMP 3. It is therefore assumed that the PK/kinin system has an important role in various symptoms, for example in thromboembolic situations, disseminated intravascular coagulation, septic shock, allergies, the postgastrectomy syndrome, arthritis and ARDS (adult respiratory distress syndrome) (Tada et al., 2001).

Accordingly, aprotinin inhibits, by its inhibitory effect on PK, the release of the peptide hormone bradykinin. Bradykinin has, via activation of the bradykinin B2 receptor, various effects. The bradykinin-induced release of tPA, NO and prostacyclin from endothelial cells (see review paper by Schmaier, 2002) influences fibrinolysis, blood pressure and the inflammatory event. It is suggested that systemic inflammatory processes which may occur as side effect in operations are reduced by inhibiting bradykinin release.

Various bisbenzamidines such as pentamidine and related compounds, and esters of ω-amino- and ω-guanidinoalkyl-carboxylic acids with micromolar $K_i$ values have been described as PK inhibitors (Asghar et al., 1976; Muramatu and Fuji, 1971; Muramatu and Fuji, 1972; Ohno et al., 1980; Muramatu et al., 1982; Satoh et al., 1985; Teno et al., 1991).

The first selective competitive inhibitors, which are derived from arginine or phenylalanine, were developed by Okamoto et al., (1988) and inhibit PK with $K_i$ values around 1 μM. Several papers on the development of competitive PK inhibitors have been published by the Okada group, with the most active compounds, which are derived from trans-4-aminomethylcyclohexanecarbonyl-Phe-4-carboxymethylanilide, having inhibition constants around 0.5 μM (Okada et al., 1999; Okada et al., 2000, Tsuda et al., 2001). It is common to the said PK inhibitors that they have a relatively high $K_i$ value. U.S. Pat. No. 6,472,393 described potent PK inhibitors with inhibition constants around 1 nM and having a 4-amidinoaniline as P1 residue. PK inhibitors have also been described in U.S. Pat. No. 5,602,253. US 2006/0148901 described PK inhibitors whose inhibitory effect on plasmin is, however, relatively small, these inhibitors differing thereby from the inhibitors described in the present application.

The invention is therefore based on the object of providing low molecular weight active substances which are suitable for therapeutic applications and which reversibly and competitively inhibit in particular plasmin and plasma kallikrein with high activity and specificity and are therefore suitable for hemostasis in various applications, for example in cardiac surgical procedures with CPB, in organ transplants or other operations. A further advantage of these compounds is that through their effect as inhibitor of plasma kallikrein in addition kinin release is reduced and thus kinin-mediated inflammatory reactions can be suppressed. The kinin-induced release of tPA from endothelial cells is in turn suppressed by the inhibited kinin release, it being possible thereby for fibrinolysis to be downregulated by this mechanism. A further advantage of these compounds is, despite selectivity, a certain inhibitory effect of these compounds on FXa and/or thrombin, and thus thrombotic complications are additionally to be reduced on use of these compounds.

SUMMARY OF THE INVENTION

It has now surprisingly been found that it was possible to obtain inhibitors with strong inhibition constants for plasmin and plasma kallikrein by combining two sterically demanding and/or hydrophobic residues $R_2$ and $R_3$ as shown in formula I, preferably substituted or unsubstituted aromatic systems. It was also possible to obtain comparably good effects with substances having on $R_2$ nonaromatic and on $R_3$ basically substituted phenyl residues.

The present invention therefore relates to compounds of the general formula (I)

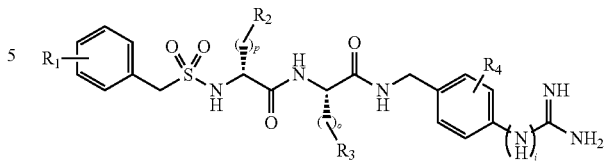

(I)

with $R_1$ optionally present one or more times and independently of one another a $COOR_5$ residue, with $R_5$ equal to hydrogen or a branched or linear lower alkyl group having 1-6 carbon atoms, preferably methyl or ethyl, in particular methyl, a branched or linear aminoalkyl residue having 1-6 carbon atoms, preferably methyl, a halogen or pseudohalogen residue, preferably chlorine or a cyano group, or a polyethylene glycol residue of the formula (II) or (III)

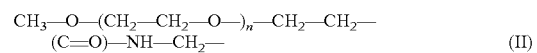 (II)

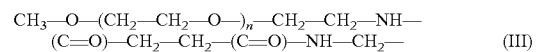 (III)

where n is ordinarily defined such that said polyethylene glycol residues have an average molecular weight of 10 000 Da, 5000 Da, 3400 Da, 2000 Da, 1000 Da or 750 Da. Normally, n is an integer between about 18 to about 250, in particular about 18, about 25, about 50, about 85, about 125 or about 250.

$R_2$ an optionally substituted, aromatic or nonaromatic cyclic or bicyclic system having 5-13 carbon atoms or aromatic heterocycle having 4-5 carbon atoms and one nitrogen atom, nitrogen oxide, oxygen atom or sulfur atom, especially a nitrogen atom or nitrogen oxide; or a residue of the structure:

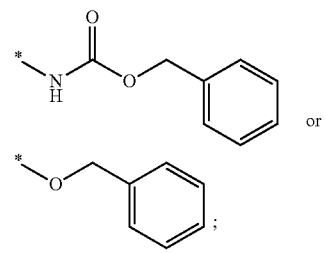

$R_3$ an optionally substituted, aromatic cyclic system having 5-6 carbon atoms or aromatic heterocycle having 3-5 carbon atoms and 1-2 nitrogen atoms, a nitrogen oxide, oxygen atom or sulfur atom, especially a nitrogen atom or nitrogen oxide;

$R_4$ optionally a halogen residue which is present one or more times, preferably fluorine;

o=1, 2 or 3, in particular 1;

p=0, 1, 2, 3 or 4, in particular 3; and i=0 or 1, in particular 0;

and the racemic mixtures and salts with organic or inorganic acids thereof.

Experimental results have shown that the inhibition of plasmin and plasma kallikrein is particularly good with compounds having cyclic structures on $R_2$ and $R_3$ and in particular having an aromatic carbocyclic system on $R_2$ and $R_3$. It has further been possible to show that by suitable choice of the substituents it is possible additionally to achieve a good inhibition of factor Xa and/or thrombin with compounds having an aromatic carbocyclic system on $R_2$ and $R_3$.

Experimental results have also shown that a marked reduction in the inhibition of thrombin is achieved when $R_1$ represents a 3-COOH group. In a preferred embodiment, therefore, $R_1$ is present once and in meta or para position, $R_1$ is preferably a COOH residue, and in particular $R_1$ is present once and is selected from hydrogen, a 4-COOH group or in particular a 3-COOH group. It was possible to achieve a further reduction in the inhibition of thrombin by $R_4$ representing a fluorine atom, in particular in ortho position.

A further preferred embodiment of the present invention relates to compounds in which $R_2$ is a substituted or unsubstituted, aromatic cyclic or bicyclic system having 6-13 carbon atoms or heterocycle having 5 carbon atoms and one nitrogen atom.

The substitution on $R_2$ can be in general a halogen residue, preferably chlorine or fluorine, in particular chlorine, an optionally fluorine-substituted, branched or linear alkyl residue having 1-6 carbon atoms, preferably methyl or tertiary butyl, an optionally fluorine-substituted, branched or linear alkyloxy residue having 1-6 carbon atoms, preferably methyl, a hydroxy residue or a cyano residue.

In an alternative embodiment, $R_2$ can also be a nonaromatic cyclic system having 6 carbon atoms.

Particularly suitable compounds have proved to be compounds of the formula (I) in which the substitution on $R_3$ is an aromatic system with basic residue, in particular an alkylamino residue having 1-3 carbon atoms, preferably 1 carbon atom, an amidino residue or guanidino residue. In particular, a compound of formula (I) with i=0 and without $R_4$ with the following residue has proved to be particularly suitable.

| Compound No. | $R_1$ | $R_2$ | p | $R_3$ | o |
|---|---|---|---|---|---|
| 3 | 3-COOH |  | 3 |  | 1 |

The salts of the compounds of the invention are generally formed from hydrochloric acid, HBr, acetic acid, trifluoroacetic acid, toluenesulfonic acid or other suitable acids.

Compounds specifically suitable are those in which $R_2$ is selected from the following residues:

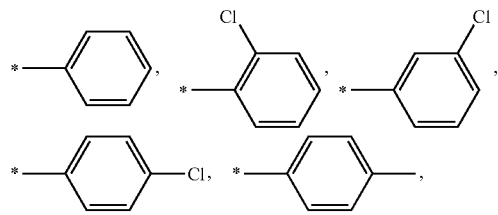

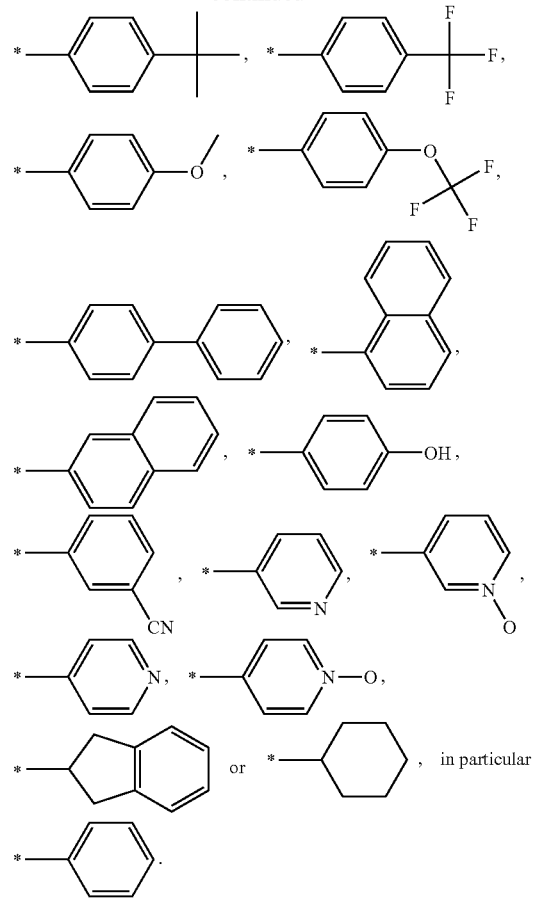

and/or in which $R_3$ is selected from

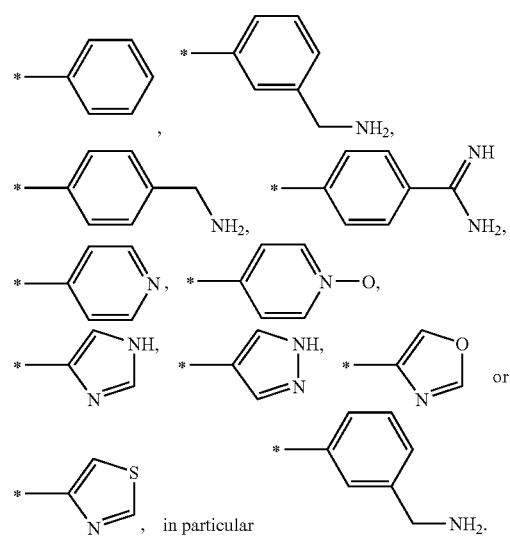

Examples of such compounds are compounds of the formula (I) which are defined as follows:

| Compound No. | R₁ | R₂ | p | R₃ | o | i | R₄ |
|---|---|---|---|---|---|---|---|
| 1 | H | 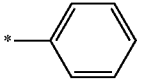 | 3 | 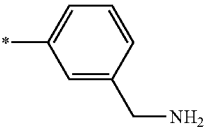 | 1 | 0 | — |
| 2 | 4-COOH | 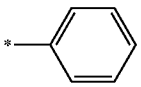 | 3 | 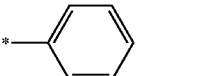 | 1 | 0 | — |
| 3 | 3-COOH | 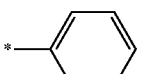 | 3 | 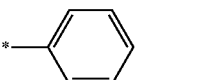 | 1 | 0 | — |
| 4 | 3-COOH | 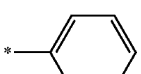 | 3 | 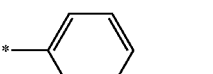 | 1 | 1 | — |
| 5 | 3-COOH | 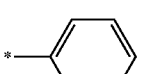 | 3 | 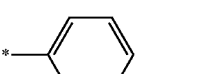 | 1 | 0 | 2-F |
| 6 | H | 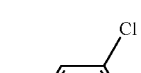 | 3 | 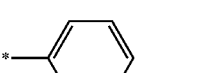 | 1 | 0 | — |
| 7 | H | 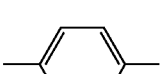 | 3 | 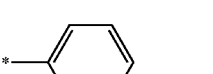 | 1 | 0 | — |
| 8 | H | 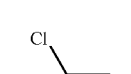 | 3 | 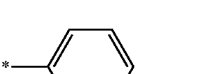 | 1 | 0 | — |
| 9 | H | 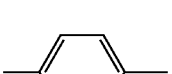 | 3 | 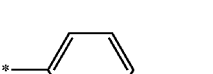 | 1 | 0 | — |
| 10 | H | 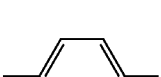 | 3 | 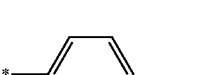 | 1 | 0 | — |

-continued
| Compound No. | R₁ | R₂ | p | R₃ | o | i | R₄ |
|---|---|---|---|---|---|---|---|
| 11 | H | 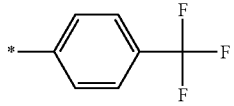 | 3 | 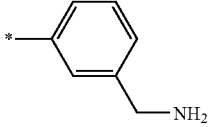 | 1 | 0 | — |
| 12 | H | 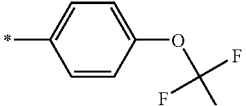 | 3 | 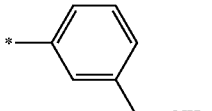 | 1 | 0 | — |
| 13 | H | 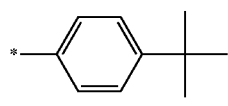 | 1 | 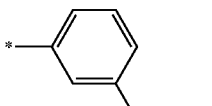 | 1 | 0 | — |
| 14 | H | 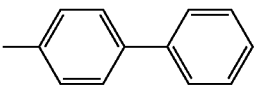 | 1 | 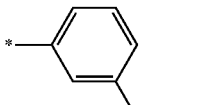 | 1 | 0 | — |
| 15 | H | 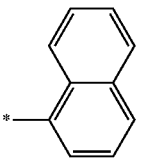 | 1 | 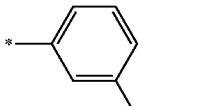 | 1 | 0 | — |
| 16 | 4-COOH | 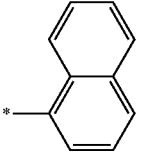 | 1 | 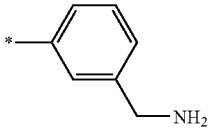 | 1 | 0 | — |
| 17 | H | 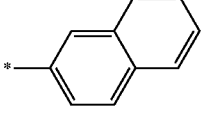 | 1 | 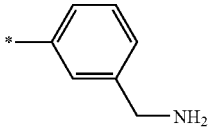 | 1 | 0 | — |
| 18 | 3-COOH | 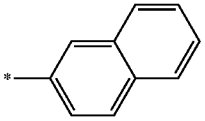 | 1 | 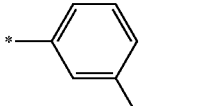 | 1 | 0 | — |
| 19 | 4-COOH | 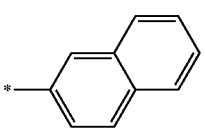 | 1 | 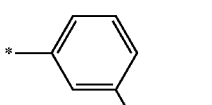 | 1 | 0 | — |
| 20 | H | 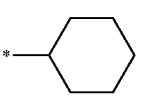 | 1 | 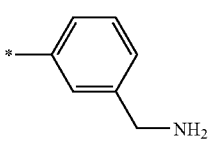 | 1 | 0 | — |

-continued

| Compound No. | R₁ | R₂ | p | R₃ | o | i | R₄ |
|---|---|---|---|---|---|---|---|
| 21 | H | *-cyclohexyl | 3 | *-C₆H₄-CH₂NH₂ (meta) | 1 | 0 | — |
| 22 | H | *-CH(C₆H₅)₂ | 0 | *-C₆H₄-CH₂NH₂ (meta) | 1 | 0 | — |
| 23 | 3-COOH | *-CH(C₆H₅)₂ | 0 | *-C₆H₄-CH₂NH₂ (meta) | 1 | 0 | — |
| 24 | H | *-C₆H₄-OH (para) | 2 | *-C₆H₄-CH₂NH₂ (meta) | 1 | 0 | — |
| 25 | 3-COOH | *-C₆H₄-OH (para) | 2 | *-C₆H₄-CH₂NH₂ (meta) | 1 | 0 | — |
| 26 | H | *-C₆H₄-OH (para) | 2 | *-C₆H₄-CH₂NH₂ (para) | 2 | 0 | — |
| 27 | H | *-C₆H₄-OH (para) | 2 | *-C₆H₅ | 2 | 0 | — |
| 28 | H | *-C₆H₅ | 3 | *-C₆H₄-CH₂NH₂ (para) | 1 | 0 | — |
| 29 | 4-COOH | *-C₆H₅ | 3 | *-C₆H₄-CH₂NH₂ (para) | 1 | 0 | — |
| 30 | 3-COOH | *-C₆H₅ | 3 | *-C₆H₄-CH₂NH₂ (para) | 1 | 0 | — |
| 31 | H | *-C₆H₅ | 3 | *-C₆H₄-CH₂NH₂ (para) | 2 | 0 | — |
| 32 | H | *-C₆H₅ | 3 | *-(1H-imidazol-4-yl) | 1 | 0 | — |

-continued
| Compound No. | R₁ | R₂ | p | R₃ | o | i | R₄ |
|---|---|---|---|---|---|---|---|
| 33 | 3-COOH | 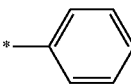 | 3 | 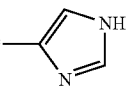 | 1 | 0 | — |
| 34 | H | 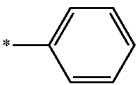 | 3 | 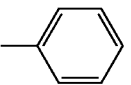 | 2 | 0 | — |
| 35 | 4-COOH | 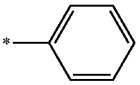 | 3 | 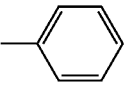 | 2 | 0 | — |
| 36 | 3-COOH | 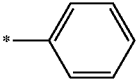 | 3 | 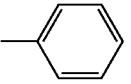 | 2 | 0 | — |
| 37 | H | 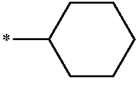 | 1 | 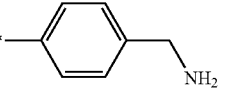 | 2 | 0 | — |
| 38 | H | 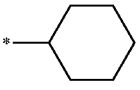 | 1 | 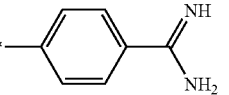 | 2 | 0 | — |
| 39 | H | 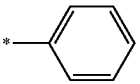 | 3 | 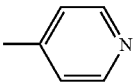 | 2 | 0 | — |
| 40 | 3-COOH | 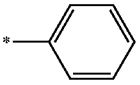 | 3 | 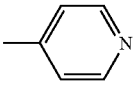 | 2 | 0 | — |
| 41 | H | 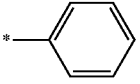 | 3 | 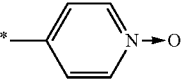 | 2 | 0 | — |
| 42 | 3-COOH | 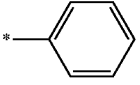 | 3 | 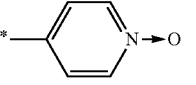 | 2 | 0 | — |
| 43 | H | 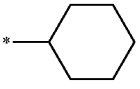 | 1 | 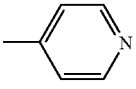 | 2 | 0 | — |
| 44 | H | 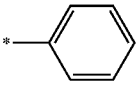 | 2 | 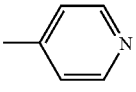 | 2 | 0 | — |
| 45 | H | 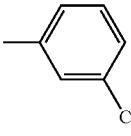 | 1 | 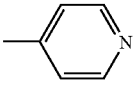 | 2 | 0 | — |
| 46 | H | 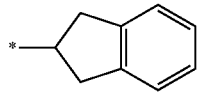 | 0 | 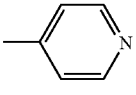 | 2 | 0 | — |
| 47 | H |  | 2 | 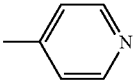 | 2 | 0 | — |

| Compound No. | $R_1$ | $R_2$ | p | $R_3$ | o | i | $R_4$ |
|---|---|---|---|---|---|---|---|
| 48 | H | *-pyridin-4-yl | 2 | *-phenyl | 3 | 0 | — |
| 49 | H | *-pyridin-4-yl | 3 | *-phenyl | 2 | 0 | — |
| 50 | 3-COOH | *-pyridin-4-yl | 3 | *-phenyl | 2 | 0 | — |
| 51 | H | *-pyridin-3-yl | 3 | *-phenyl | 2 | 0 | — |
| 52 | 3-COOH | *-pyridin-3-yl | 3 | *-phenyl | 2 | 0 | — |
| 53 | H | *-pyridin-4-yl N-oxide | 3 | *-phenyl | 2 | 0 | — |
| 54 | 3-COOH | *-pyridin-4-yl N-oxide | 3 | *-phenyl | 2 | 0 | — |
| 55 | H | *-pyridin-3-yl N-oxide | 3 | *-phenyl | 2 | 0 | — |
| 56 | 3-COOH | *-pyridin-3-yl N-oxide | 3 | *-phenyl | 2 | 0 | — |

It has also emerged that compounds of the general formula (IV)

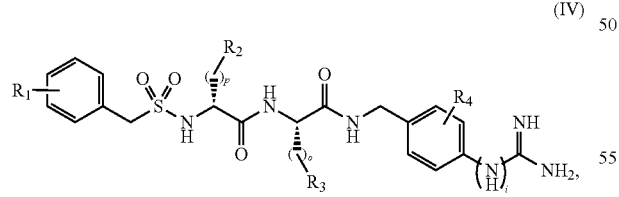

(IV)

which corresponds to the general formula (I), with $R_1$, optionally present one or more times and independently of one another a $COOR_5$ residue, with $R_5$ equal to hydrogen or a branched or linear lower alkyl group having 1-6 carbon atoms, preferably methyl or ethyl, in particular methyl, a branched or linear aminoalkyl residue having 1-6 carbon atoms, preferably methyl, a halogen or pseudohalogen residue, preferably chlorine or a cyano group, or a polyethylene glycol residue of the formula (V) or (VI)

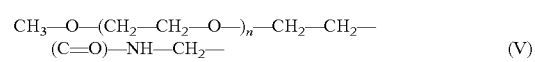

(V)

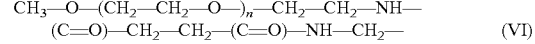

(VI)

where n is defined such that the polyethylene chain has an average molecular weight of 10 000 Da, 5000 Da, 3400 Da, 2000 Da, 1000 Da or 750 Da, n is preferably an integer between about 18 to about 250, in particular about 18, about 25, about 50, about 85, about 125 or about 250;

$R_2$ a branched or linear alkyloxy residue having 1-6 carbon atoms, preferably tertiary butyl, a hydroxyl residue, amino residue or a branched or linear alkyloxycarbonylamido residue having 1-6 carbon atoms, preferably tertiary butyl, or a polyethylene glycol residue of the formula (V) or (VI) with n as defined above;

$R_3$ selected from the following residues:

preferably

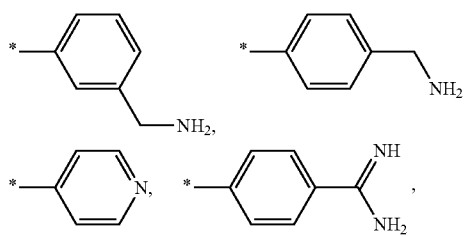

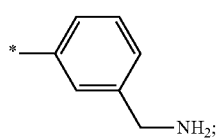

$R_4$ optionally a halogen residue which is present one or more times, preferably fluorine, o=1 or 2;

p=1, 2, 3 or 4, in particular 1 or 4, i=0 or 1, in particular 0;

and the racemic mixtures and salts with organic or inorganic acids thereof, are also suitable according to the present invention.

Preferred compounds in this case also are those in which $R_1$ is present once and in meta or para position, $R_1$ is preferably hydrogen or a COOH residue, and in particular $R_1$ is present once and is selected from hydrogen, a 4-COOH group or a 3-COOH group.

The salts of these compounds are once again generally formed from hydrochloric acid, HBr, acetic acid, trifluoroacetic acid, toluenesulfonic acid or other suitable acids.

Examples of such compounds are compounds of the formula (IV) with i=0 and without $R_4$ residue, which are defined as follows:

| Compound No. | $R_1$ | $R_2$ | p | $R_3$ | o |
|---|---|---|---|---|---|
| 57 | H | *-NH-C(=O)-O-C(CH3)3 | 4 | *-C6H4-CH2-NH2 (meta) | 1 |
| 58 | 4-COOH | *-NH-C(=O)-O-C(CH3)3 | 4 | *-C6H4-CH2-NH2 (meta) | 1 |
| 59 | H | *—NH2 | 4 | *-C6H4-CH2-NH2 (meta) | 1 |
| 60 | H | *-NH-C(=O)-O-C(CH3)3 | 1 | *-C6H4-CH2-NH2 (meta) | 1 |
| 61 | H | *—NH2 | 1 | *-C6H4-CH2-NH2 (meta) | 1 |
| 62 | H | *-NH-C(=O)-O-C(CH3)3 | 4 | *-4-pyridyl | 2 |
| 63 | H | *-O-C(CH3)3 | 1 | *-C6H4-CH2-NH2 (meta) | 1 |

-continued
| Compound No. | R₁ | R₂ | p | R₃ | o |
|---|---|---|---|---|---|
| 64 | 4-COOMe | 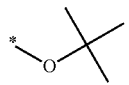 | 1 | 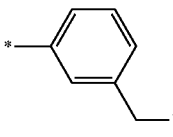 | 1 |
| 65 | 4-COOH | 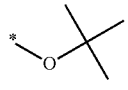 | 1 | 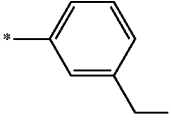 | 1 |
| 66 | 3-COOMe | 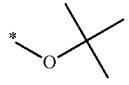 | 1 | 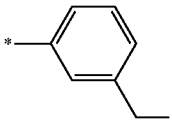 | 1 |
| 67 | 3-COOH | 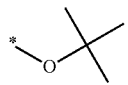 | 1 | 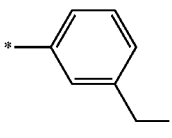 | 1 |
| 68 | H | *—OH | 1 | 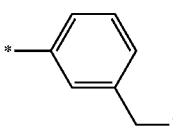 | 1 |
| 69 | 4-COOMe | *—OH | 1 | 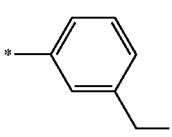 | 1 |
| 70 | 4-COOH | *—OH | 1 | 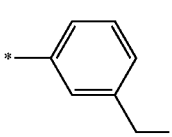 | 1 |
| 71 | H | 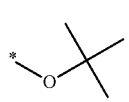 | 1 | 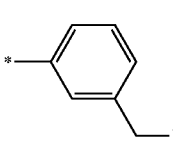 | 1 |
| 72 | H | *—OH | 1 | 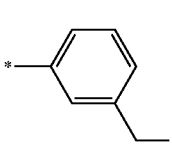 | 1 |
| 73 | H |  | 1 | 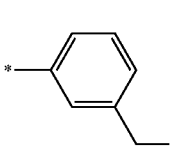 | 2 |
| 74 | H | *—OH | 1 | 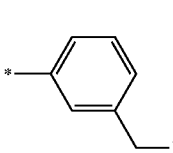 | 2 |

The compounds of the general formula I can be prepared in a manner known in principle, as described hereinafter, for example as follows, with in general the appropriate amino acids being coupled sequentially to an amidinobenzylamine protected at the amidino group. In this case, the N-terminal amino acid either already has the P4 residue, or the latter is subsequently linked thereto.

The nomenclature of the individual constituents P1, P2, P3 and P4 of the compounds of the invention is evident hereinafter (see also Schechter and Berger, 1967).

For example, the protected, preferably Boc-protected, amidinobenzylamine which is protected at the amidino 7 group, in particular 4-acetyloxamidinobenzylamine, is obtained from the commercially available 4-cyanobenzylamine (Showa Denko K.K., Japan) by processes known to a person skilled in the art. Cleavage of the protective group is followed by coupling of the further amino acids and of the P4 residue by standard coupling methods and protective groups, preferably with Boc as N-terminal protective group. The P3 amino acid can also be coupled directly as protected, preferably benzylsulfonyl-protected, amino acid already having the R1 residue. The peptide analogs are assembled sequentially, starting from the acetyloxamidinobenzylamine. Most of the intermediates crystallize well and can thus be easily purified. The final purification of the inhibitors takes place at the last stage, preferably by preparative, reversed-phase HPLC.

The invention therefore further relates to a process for preparing a compound of the invention, where the appropriate amino acids are coupled sequentially to an amidino- or guanidinobenzylamine protected at the amidino or guanidino group, for example to a 4-acetyloxamidinobenzylamine or to a 4-(benzyloxycarbonylamidino)benzylamine, with the N-terminal amino acid either already having the P4 residue, or the latter subsequently being linked thereto. After possible purification, the resulting compounds can optionally be PEGylated.

An exemplary process for preparing the compounds of the invention includes the following steps:

(a) amidation of an appropriate Nα-protected amino acid with the residue $R_3$ with an appropriate protected aminomethylbenzamidine or -guanidine, (b) after cleavage of the Nα-protective group of the amino acid with $R_3$ reaction of the resulting product with the appropriate benzylsulfonylamino acid with the residues $R_1$ and $R_2$ and cleavage of remaining protective groups to give the compound of the invention and, after a possible purification, (c) the resulting compound is optionally PEGylated.

Further process details which are generally known to a person skilled in the art, e.g. concerning the chosen protective groups or the PEGylation, can be found in the examples. A preferred protective group of the amide nitrogen is for example tert-butyloxycarbonyl (Boc). The starting compounds are, for example, amino acid derivatives or PEG derivatives. The chemicals can generally be obtained by purchase. The PEGylation, i.e. the derivatization with polyethylene glycol, generally took place either via the P3 amino acid or via the P4 benzylsulfonyl residue with activated PEG derivatives, e.g. with PEG activated as n-hydroxysuccinimide ester.

An advantageous property of the PEG-coupled compounds is the prolongation of the half-life of the inhibitors in the blood circulation. The following structure shows an example in which the PEG chain has been coupled via the P3 amino acid (D-Lys).

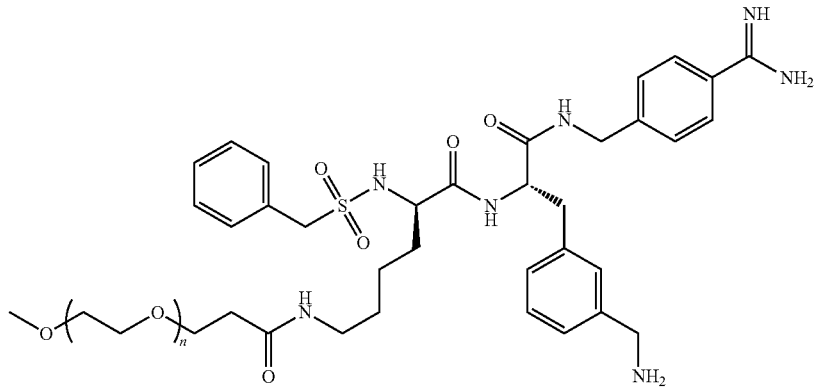

The following compound was obtained by using a succinyl linker:

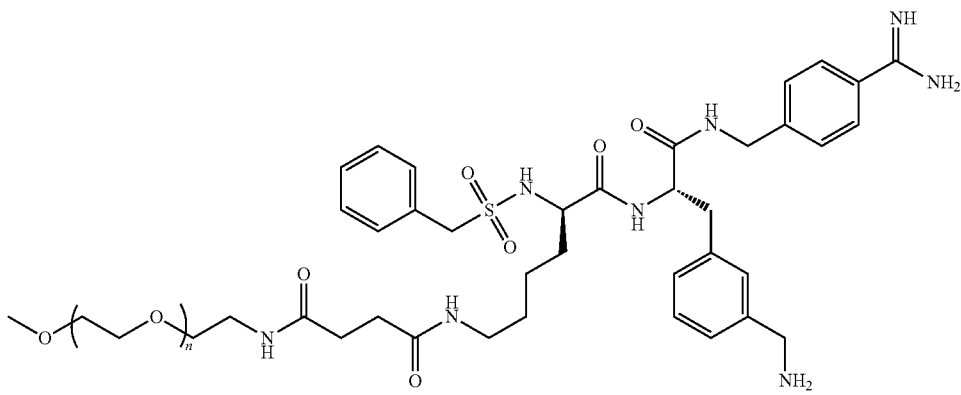

In addition, the PEG chain was coupled to via a suitable P4-benzylsulfonyl residue in accordance with the general formula depicted below, with the P4 residue having been modified in the para or ortho position with an aminomethyl group.

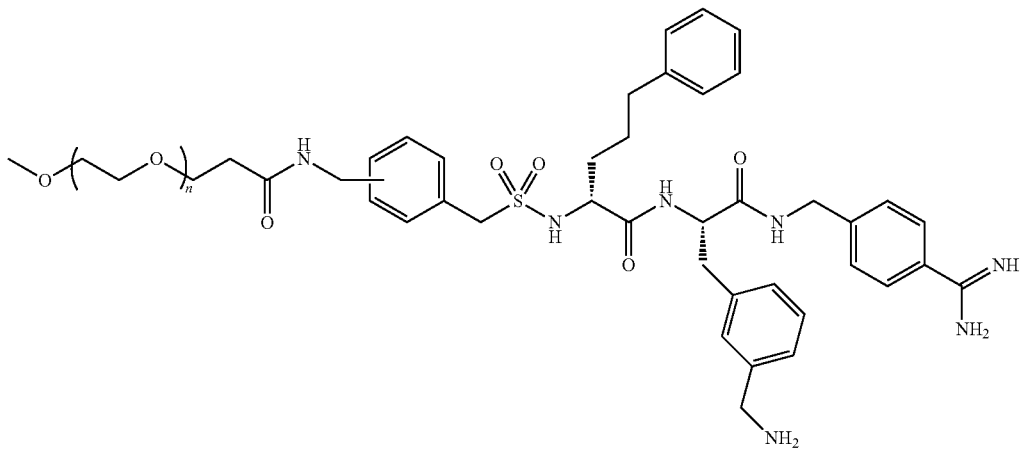

The following compound was obtained using a succinyl linker:

However, other preparation processes which can be carried out in the same way are also known to a person skilled in the art. The PEGylated compounds are generally mixtures of compounds with various degrees of PEGylation, and the molecular weight of the PEG residues is normally in the region of 750, 1000, 2000, 3400, 5000 or 10 000 Da. How-

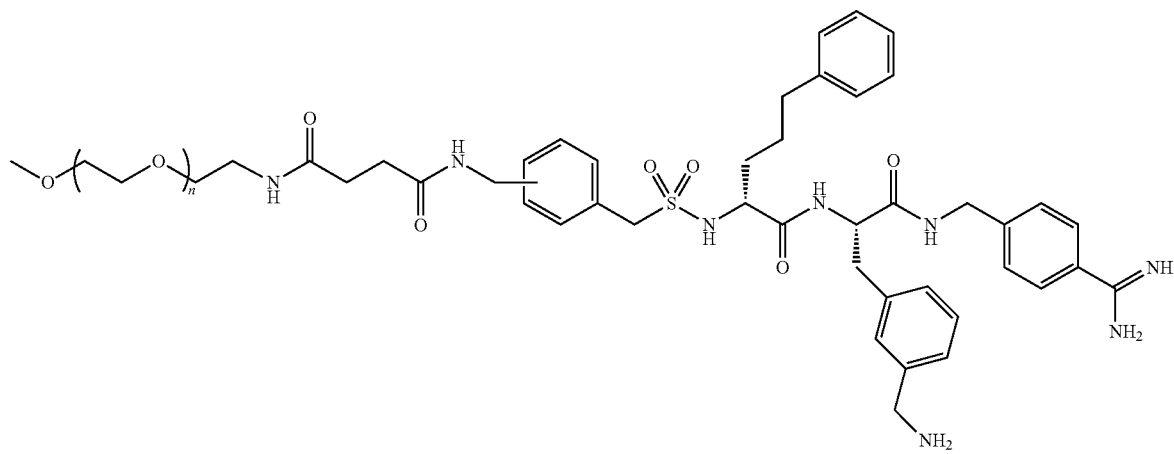

ever, other specific polyethylene glycols with defined molecular weight can also be obtained by purchase.

The present invention also extends to a medicament comprising at least one of the compounds of the invention, preferably for the treatment of blood loss, in particular in hyperfibrinolytic conditions, in organ transplants or cardiac surgical procedures, in particular with cardiopulmonary bypass.

The present invention also includes a fibrin adhesive which comprises at least one of the compounds of the invention, in which aprotinin is replaced by a suitable inhibitor of the present invention.

Fibrin adhesives generally mean a physiological two-component adhesive which comprises as first component fibrinogen, factor XIII and aprotinin or at least one of the compounds of the invention, and as second component thrombin and calcium chloride for factor XIII activation.

The present invention also relates to the use of at least one compound of the invention for the manufacture of a medicament of the invention or of a fibrin adhesive of the invention by processes generally known to a person skilled in the art, e.g. by mixing with suitable excipients or additives.

The present invention also relates to the following aspects:
Compounds of the General Formula

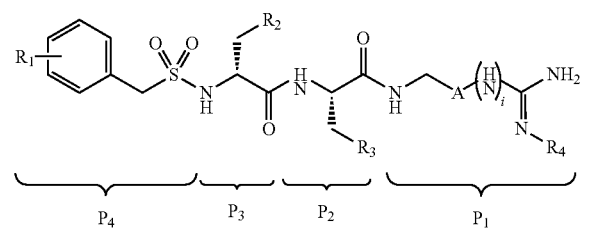

i is 0 or 1, preferably 0
$R_4$ is H or OH, preferably H
A is selected from the following structures:

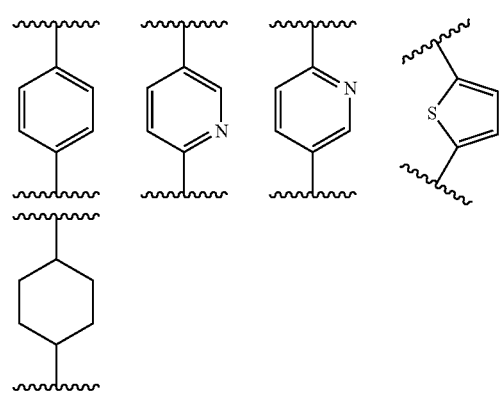

where A is preferably a phenyl residue,
$R_1$ is H, COOH, COOR$_5$ (with R$_5$=methyl or ethyl), aminomethyl, halogen, pseudohalogen, but preferably H and COOH and particularly preferably COOH, because the carboxyl group prolongs the half-life of the inhibitors in the circulation, $R_3$ is

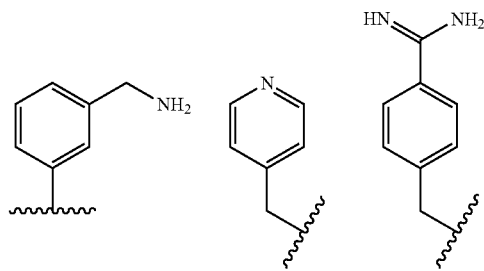

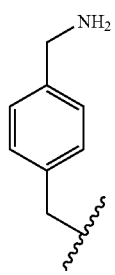

$R_2$ is branched or unbranched alkyl having 3-12 C atoms, also cycloalkyl-substituted, aryl or aralkyl having 6-14 C atoms, heteroaryl or as heteroarylalkyl having 6-12 C atoms and 1-3 heteroatoms, also

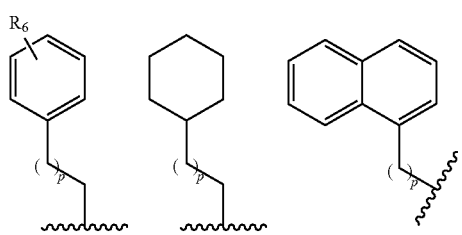

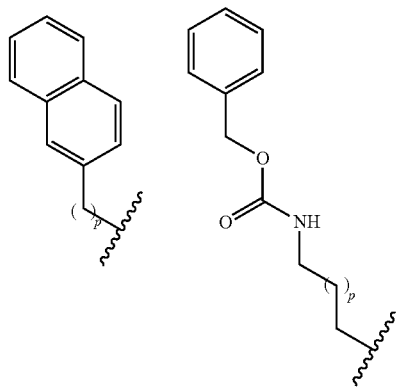

$R_6$ is halogen or pseudohalogen with p=0, 1, 2, and the racemates, crystal forms and hydrates and salts with organic and inorganic acids thereof.

Compounds of the following formula in which the individual positions are designated P4-P1:

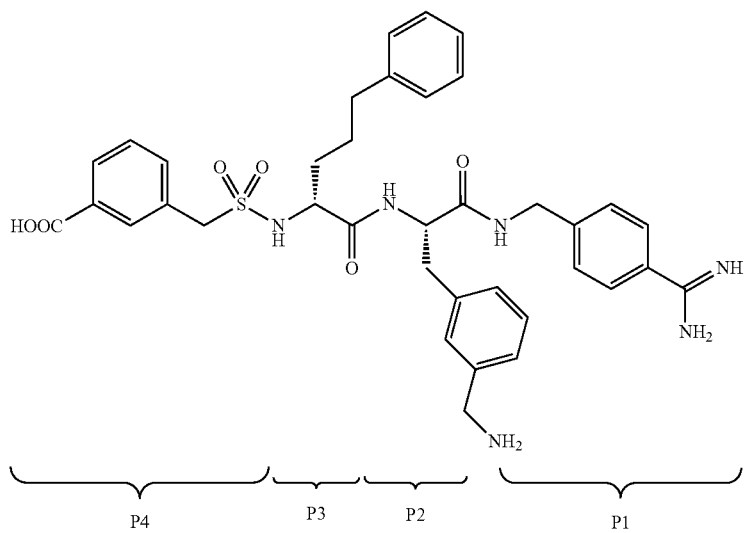

with
P4=benzylsulfonyl residue unmodified or substituted
P3=hydrophobic amino acid in the D configuration, D-phenylpropylglycine and further amino acids
P2=basic-hydrophobic amino acids in the L configuration
P1=4-amidinobenzylamide residue and related groups.

Compounds of the following structure which are coupled to PEG via P3 as follows:

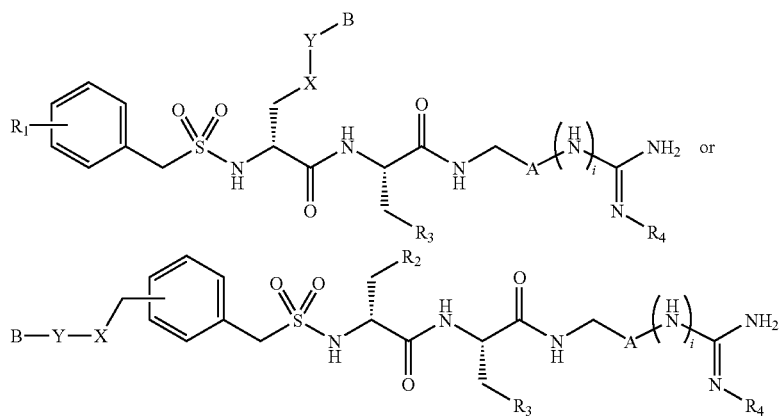

The designations $R_1$, $R_2$, $R_3$, $R_4$, A and i correspond to the definitions indicated above. B corresponds to the PEG chain which is in the form of the methyl ether at the end. Y is a suitable linker for coupling the PEG to the P3 amino acid, for example a propionyl residue, and X is either an NH or an NH-alkyl or NH-aryl group. The coupling takes place in a manner known per se.

The compounds of the invention have for example a PEG chain which has an average molecular mass of 750 Da, 1000 Da, 2000 Da, 5000 Da, 10 000 Da, 20 000 Da or is a specific PEG chain.

Use of the compounds of the invention for the manufacture of a medicament which is suitable for reducing blood loss in hyperfibrinolytic conditions, and use of the compounds of the invention as means for preparing a fibrin adhesive.

BRIEF DESCRIPTION OF THE DRAWINGS

FIGS. 1A-1K show the inhibitory effects of Compound No. 3, aprotinin, and tranexamic acid on t-PA-induced lysis of whole blood clots.

FIG. 3 shows the influence of Compound No. 3 and aprotinin on coagulation parameters in vitro.

FIGS. 4A-4F show the effects of Compound No. 3 and aprotinin on thrombin generation in platelet-rich human plasma.

DETAILED DESCRIPTION OF THE INVENTION

Figures 2A, 2B:
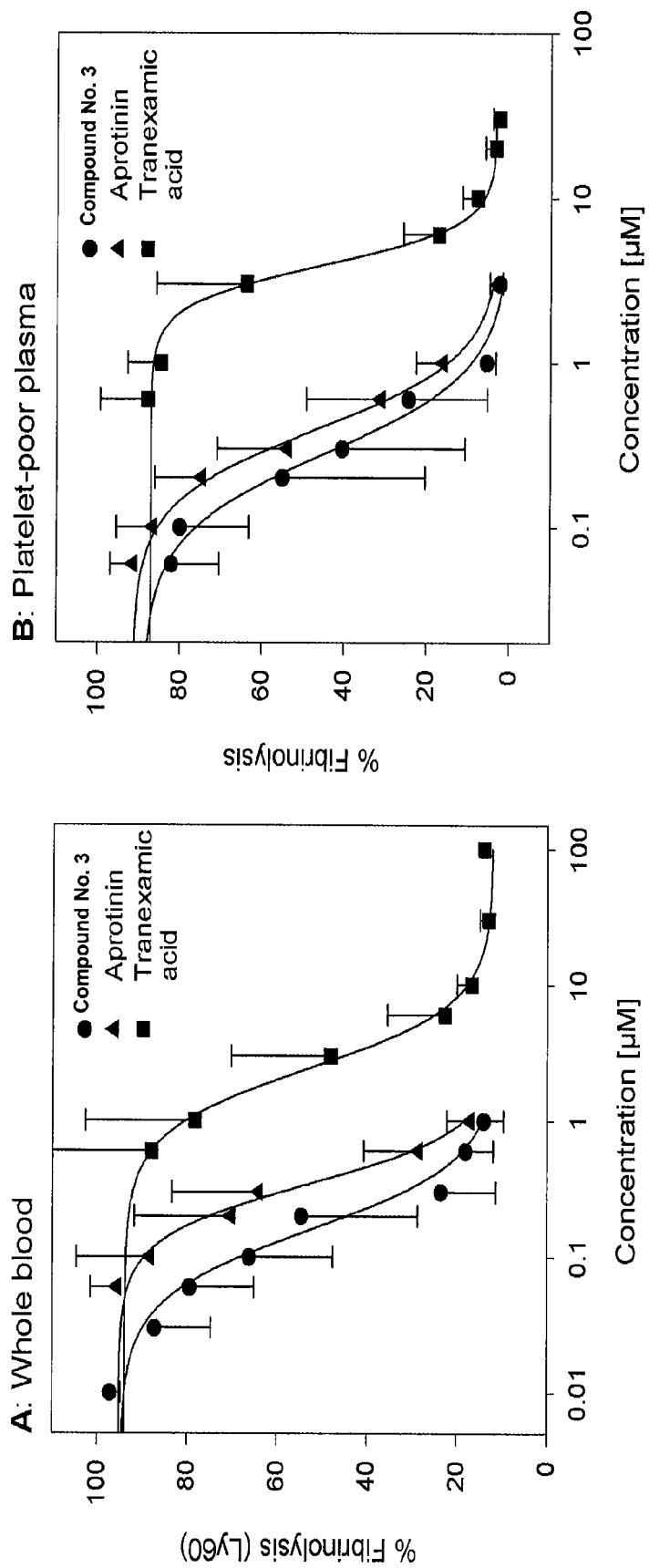
FIGS. 2A and 2B show the concentration-response curves of antifibrinolytic efficacy of Compound No. 3, aprotinin, and tranexamic acid in human whole blood and plasma.

In one aspect, the present invention relates to compounds of the general formula (I)

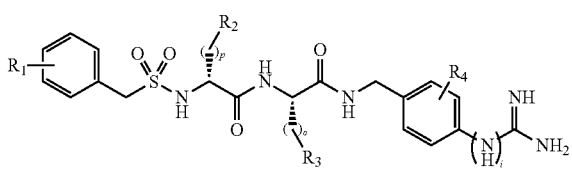

wherein
$R_1$ is optionally present one or more times and each $R_1$ is, independently, hydrogen or $COOR_5$;
$R_2$ is an optionally substituted ring system wherein said ring system is selected from (i) an aromatic or nonaromatic cyclic or bicyclic system comprising 5-13 carbon atoms, (ii) an aromatic heterocycle comprising 4-5 carbon atoms and one nitrogen atom, nitrogen oxide, oxygen atom, or sulfur atom, and (iii) a residue of the structure:

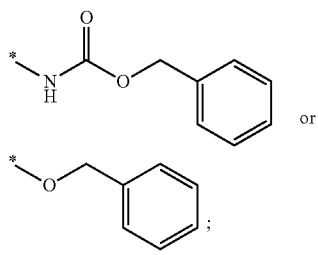

$R_3$ is an optionally substituted ring system wherein said ring system is selected from (i) an aromatic cyclic system comprising 5-6 carbon atoms, and (ii) an aromatic heterocycle comprising 3-5 carbon atoms and 1-2 nitrogen atoms, a nitrogen oxide, oxygen atom, or sulfur atom;
$R_4$ is optionally present one or more times and each $R_4$ is, independently, hydrogen or a halogen;
$R_5$ is hydrogen, a branched or linear lower alkyl group comprising 1-6 carbon atoms, a branched or linear aminoalkyl residue comprising 1-6 carbon atoms, a halogen or pseudohalogen residue, or a polyethylene glycol residue of the formula (II) or (III):

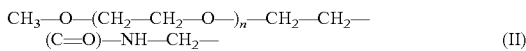

or

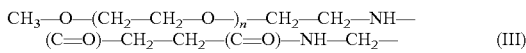

wherein said polyethylene glycol residue has a molecular weight of from 750 Da to 10,000 Da, and n is an integer from 25 to 250;
o=1, 2 or 3;
p=0, 1, 2, 3 or 4;
i=0 or 1;
and salts thereof.

In some embodiments, $R_5$ is methyl, ethyl, a branched or linear aminoalkyl residue comprising a methyl group, chlorine, a cyano group, or a polyethylene glycol residue of the formula (II) or (III) in which n is 18, 25, 50, 85, 125, or 250; $R_2$ is an optionally substituted ring system wherein said ring system is an aromatic heterocycle comprising 4-5 carbon atoms and one nitrogen atom or nitrogen oxide; $R_3$ is an optionally substituted ring system wherein said ring system is an aromatic heterocycle comprising 4-5 carbon atoms and one nitrogen atom or nitrogen oxide; $R_4$ is fluorine; o is 1; p is 3; and i is 0.

In some embodiments, $R_1$ is a $COOR_5$ residue present once and in the meta or para position; $R_2$ is an optionally substituted ring system wherein said ring system is phenyl, napthyl, pyridinyl, or pyridinyl-N-oxide group; $R_3$ is phenyl or phenyl substituted with an alkylamino residue having 1-3 carbon atoms; $R_4$ is hydrogen; $R_5$ is hydrogen or a branched or linear lower alkyl group having 1-6 carbon atoms; o is 1 or 2; and i is 0.

In some embodiments, $R_1$ is $COOR_5$ present once and in the meta or para position.

In some embodiments, $R_5$ is hydrogen.

In some embodiments, $R_2$ is an aromatic cyclic or bicyclic system comprising 6-13 carbon atoms or a heterocycle comprising 5 carbon atoms and a nitrogen atom.

In some embodiments, $R_2$ is an optionally substituted ring system comprising a substituent selected from a halogen residue, an optionally fluorine-substituted branched or linear alkyl residue having 1-6 carbon atoms, an optionally fluorine-substituted branched or linear alkyloxy residue having 1-6 carbon atoms, a hydroxy residue, or a cyano residue. In further embodiments, the substituent is selected from chlorine, fluorine, methyl, tertiary butyl, and $OCH_3$.

In some embodiments, $R_2$ is a nonaromatic cyclic system comprising 6 carbon atoms.

In some embodiments, $R_3$ is a basic residue.

In some embodiments, $R_3$ is an optionally substituted ring system comprising a substituent selected from an alkylamino residue having 1-3 carbon atoms, an amidino residue, and guanidino residue. In other embodiments, substituent is an alkylamino residue comprising 3 carbon atoms.

In other embodiments, the compound is a salt selected from chloride, bromide, acetate, trifluoroacetate, and toluenesulfonate.

In some embodiments, $R_2$ is selected from the following residues:

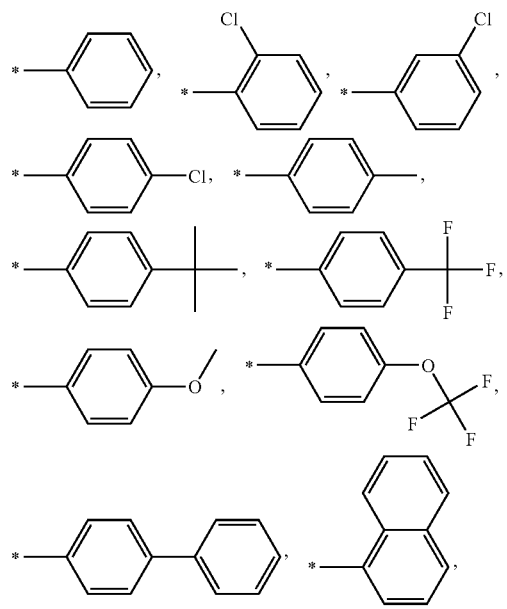

-continued

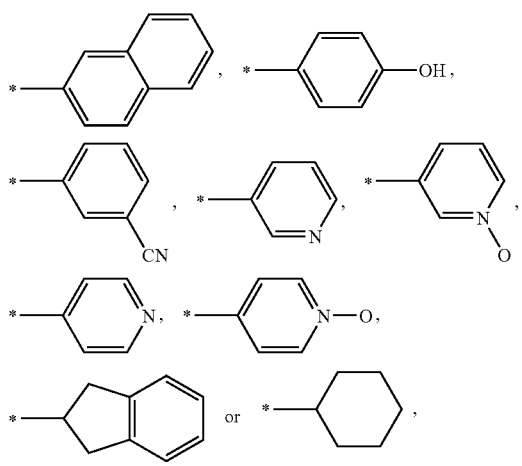

In some embodiments, $R_2$ is

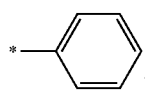

In some embodiments, $R_3$ is selected from

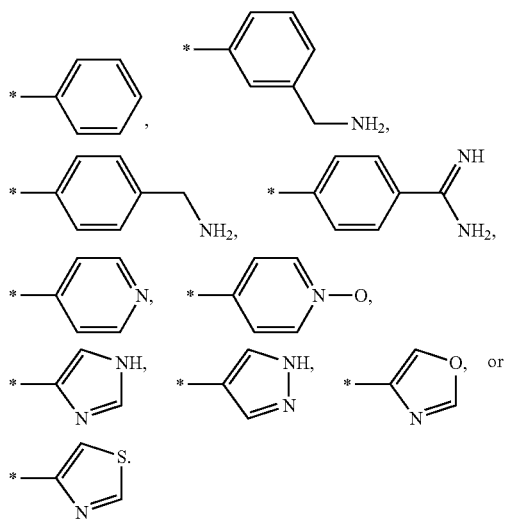

In certain embodiments, $R_3$ is

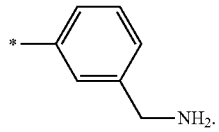

In some embodiments, the compound, or a salt thereof, is any of Compounds Nos. 1-56 as described herein. In some embodiments, the compound is Compound No. 3 which has the following structure:

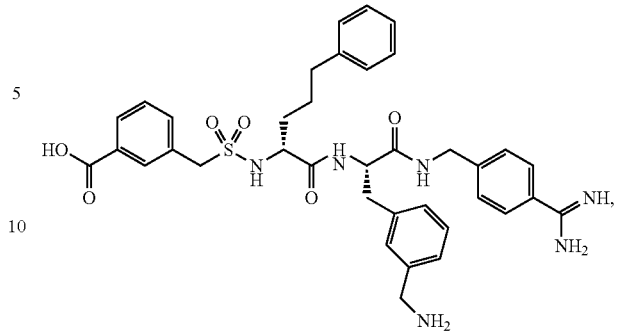

or a salt thereof.

In another aspect, the invention features compounds of the general formula (IV)

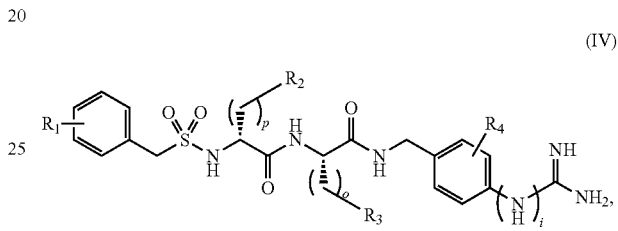

which corresponds to the general formula (I), wherein
  $R_1$ is optionally present one or more times and each $R_1$ is, independently, hydrogen or $COOR_5$;
  $R_2$ is a branched or linear alkyloxy residue comprising 1-6 carbon atoms, a branched or linear alkyloxycarbonylamido residue comprising 1-6 carbon atoms, or a polyethylene glycol residue of the formula (V) or (VI) with n as defined below;
  $R_3$ selected from the following residues:

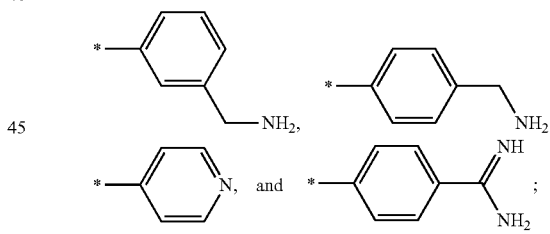

$R_4$ is optionally present one or more times and each $R_4$ is, independently, hydrogen or a halogen;
  $R_5$ is hydrogen, a branched or linear lower alkyl group comprising 1-6 carbon atoms, a branched or linear aminoalkyl residue comprising 1-6 carbon atoms, a halogen or pseudohalogen residue, or a polyethylene glycol residue of the formula (V) or (VI)

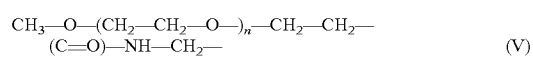

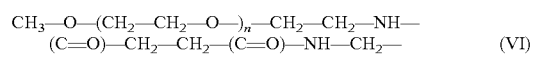

wherein said polyethylene glycol residue has a molecular weight of from 750 Da to 10,000 Da and n is an integer from 25 to 250;
  o=1 or 2;

p=1, 2, 3 or 4;
i=0 or 1, in particular 0;
and salts thereof.

In some embodiments, $R_5$ is methyl, ethyl, a branched or linear aminoalkyl residue comprising a methyl group, chlorine, a cyano group, or a polyethylene glycol residue of the formula (V) or (VI) in which n is 18, 25, 50, 85, 125, or 250; $R_2$ is a branched or linear alkyloxy residue comprising a tertiary butyl group or a branched or linear alkyloxycarbonylamido residue having a tertiary butyl group; $R_3$ is

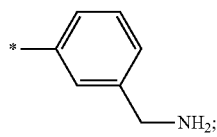

$R_4$ is fluorine; p is 1 or 4; and i is 0.

In some embodiments, $R_1$ is $COOR_5$ present once and in meta or para position. In some embodiments, $R_5$ is hydrogen (e.g., a 4-COOH group or a 3-COOH group).

In some embodiments, the compound is a salt selected from chloride, bromide, acetate, trifluoroacetate, and toluenesulfonate.

In some embodiments, the compound, or salt thereof, is any of Compound Nos. 60-78 as described herein.

In another aspect, the invention relates to a medicament that includes the compound of the invention (e.g., a compound of formula (I)), or a salt thereof, and can further comprise suitable excipients or additives. In further embodiments, the medicament is for the treatment of blood loss. In some embodiments, the blood loss occurs in hyperfibrinolytic conditions, in organ transplants, or cardiac surgical procedures. The invention also features fibrin adhesive comprising the compound of the invention (e.g., a compound of formula (I)), or a salt thereof.

The following examples are intended to explain the invention in detail without restricting it.

Examples

1. Analytical Methods 1.1 Analytical HPLC

A Shimadzu LC-10A HPLC system consisting of the subsystems CTO-10AS column oven, LC-10AD pumps (2×), DGU-14A degaser, SIL-10AD autoinjector, SCL-10A system controller, SPD-10A UV-Vis detector and a Phenomenex Luna 5 μm C18(2) 100 Å, 250×4.6 mm column, was used for the analytical reversed-phase HPLC, utilizing the relevant Shimadzu CLASS-VP software, Version 5.3. Detection took place at 220 nm. Water with 0.1% TFA (A) and acetonitrile with 0.1% TFA (B) served as eluents at a flow rate of 1 ml/min and a linear gradient (1% B/min). Different starting conditions were used for the analytical HPLC depending on the compound, which are indicated for the corresponding compounds.

A Phenomenex Jupiter 5 μm C18(2) 300 Å, 250×4.6 mm column was used for analyzing all the polyethylene glycol-modified active substances.

1.2 Preparative HPLC

A Shimadzu HPLC system consisting of the subsystems LC-8A preparative pumps (2×), DGU-14A degaser, FRC-10A fraction collector, SCL-10A system controller, SPD-10A UV-Vis detector and a Phenomenex Luna 5 μm C8(2) 100 Å, 250×30.0 mm column was used for the preparative RP-HPLC, utilizing the relevant Shimadzu CLASS-VP software, Version 5.3. Detection took place at 220 nm. Water with 0.1% TFA (A) and acetonitrile with 0.10% TFA (B) likewise served as eluents, at a flow rate of 10 or 20 ml/min and a suitable gradient.

1.3 Mass Spectroscopy

The mass spectra were recorded routinely on a Finnigan ESI-MS LCQ (Bremen, Germany). All the polyethylene glycol-coupled compounds were analyzed in a Bruker Maldi Ultraflex Tof/Tof instrument.

Abbreviations Used
ACN Acetonitrile
4-Amba 4-Amidinobenzylamide
Ame Aminomethyl
Boc tert.-Butyloxycarbonyl
BSA bovine serum albumin
Bzl Benzyl
Bzls Benzylsulfonyl
DIEA Diisopropylethylamine
DCM Dichloromethane
DMF N,N-Dimethylformamide
HBTU 2-(1H-Benzotriazol-1-yl)-1,1,3,3-tetramethyluronium hexafluorophosphate
HPLC High performance liquid chromatography
MS Mass spectroscopy
ONHS N-Hydroxysuccinimide ester
NMM N-Methylmorpholine
PEG Polyethylene glycol
Phe(3-Ame) 3-Aminomethylphenylalanine
Ppg Phenylpropylglycine
RT Room temperature
tBu tert.-Butyl
Tfa Trifluoroacetyl
TFA Trifluoroacetic acid
TEA Triethylamine
TMS-CL Trimethylsilyl chloride
Me Methyl 2. Synthesis of the Inhibitors 2.1 3-HOOC-Bzls-d-Ppg-Phe(3-Ame)-4-Amba×2 acetate (3)

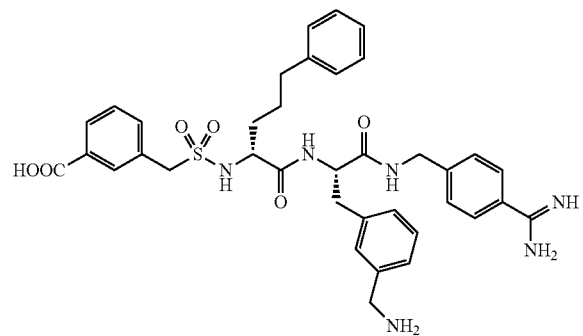

a) Boc-Phe(3-Ame)-OH×acetate

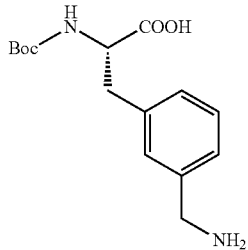

5 g (17.2 mmol) of Boc-Phe(3-CN)—OH (Acros Organics) were dissolved in 700 ml of 90% strength acetic acid and hydrogenated with hydrogen under atmospheric pressure and 800 mg of 10% Pd/C as catalyst at 40° C. for 3 hours. The solvent was removed in vacuo, and the residue was dissolved in a small amount of methanol and precipitated by adding diethyl ether.

Yield: 4.1 g (HPLC: 16.7 min, Start with 10% B)

b) Boc-Phe(3-Tfa-Ame)-OH

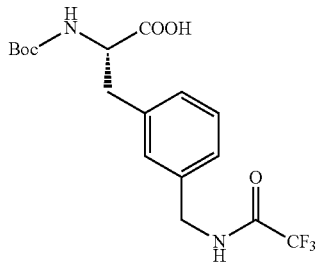

4.6 g (13 mmol) of Boc-Phe(3-Ame)-OH×acetate were dissolved in 30 ml of methanol, and 4 ml (29.9 mmol) of DIEA and 2 ml (16.78 mmol) of ethyl trifluoroacetate were added at room temperature. The mixture is stirred until the original suspension has completely dissolved after about 15 min. After one hour, the solvent is removed in vacuo, and the residue is dissolved in ethyl acetate and water. The ethyl acetate phase is washed 2× with 5% $KHSO_4$ solution and 3× with saturated NaCl solution, and the organic phase is dried with $Na_2SO_4$. The solvent is removed in vacuo.

Yield: 4.9 g of amorphous solid (HPLC: 28.13 min, Start with 20% B)

c) Boc-Phe(3-Tfa-Ame)-4-(acetylhydroxyamidino) benzylamide

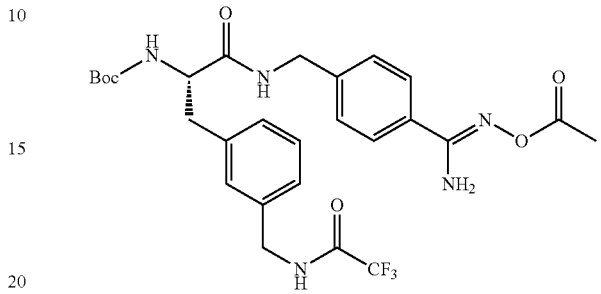

5.43 g (13.9 mmol) of Boc-Phe(3-Tfa-Ame)-OH and 4.28 g (15.3 mmol) of 4-(acetylhydroxyamidino)benzylamine (synthesis described in the supplement to Schweinitz et al., 2004) were dissolved in 50 ml of DMF and, at 0° C., 5.2 ml (30 mmol) of DIEA and 5.81 g (15.3 mmol) of HBTU were added. The mixture is stirred at 0° C. for 15 min and at RT for a further 3 h. The solvent is removed in vacuo, and the residue is dissolved in ethyl acetate. The ethyl acetate phase is washed 3× with 5% $KHSO_4$ solution, 1× with saturated NaCl solution, 3× with saturated $NaHCO_3$ solution and 2× with saturated NaCl solution. The product which precipitates between the phases is filtered off with suction and dried in vacuo.

Yield: 4.17 g of white crystals (HPLC: 28.08 min, Start with 20% B)

d) H-Phe(3-Tfa-Ame)-4-(acetylhydroxyamidino) benzylamide×HCl

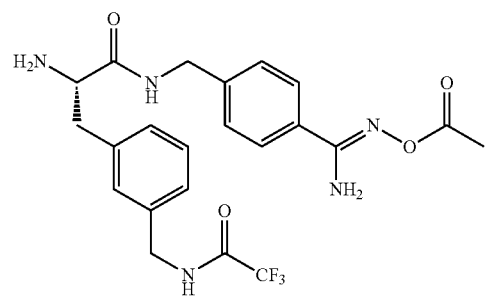

4.1 g of Boc-Phe(3-Tfa-Ame)-4-(acetylhydroxyamidino) benzylamide were suspended in 60 ml of dry dioxane, and 11 ml of 4 N HCl in dioxane were added. After brief ultrasonic treatment, the mixture is shaken at room temperature for 1 h. After 1 h, the product is precipitated by adding diethyl ether and is filtered off with suction and dried in vacuo.

Yield: 3.8 g of white solid (HPLC: 9.47 min, Start with 20% B)

e) 3-MeOOC-Bzl-SO$_3^-$×Na$^+$

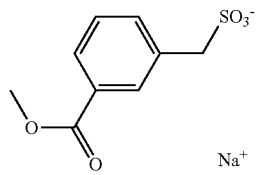

5 g (21.8 mmol) of methyl 3-bromomethylbenzoate (Acros Organics) were suspended in 25 ml of water, and 2.94 g (23.8 mmol) of Na$_2$SO$_3$ were added. The mixture was refluxed for 5 h and then part of the solvent was removed in vacuo until crystallization had started. The mixture was stored at 4° C. overnight, and the product was filtered off.

Yield: 3.7 g of white crystals (HPLC: 12.02 min, Start with 10% B)

f) 3-MeOOC-Bzls-Cl

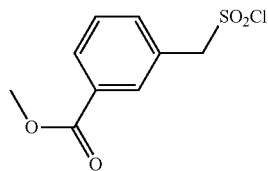

2.5 g (9.91 mmol) of 3-MeOOC-Bzl-SO$_3^-$×Na$^+$ were moistened with phosphoryl chloride, and 2.27 g (10.9 mmol) of PCl$_5$ were added. The mixture was cooled at 0° C. for about 5 min and then heated on an oil bath (bath temperature 80° C.) for 4 h. The mixture was then poured onto ice and vigorously stirred. After stirring for about 30 min, the acid chloride begins to precipitate and is filtered off with suction and dried in vacuo.

Yield: 1.4 g of white solid g) 3-MeOOC-Bzls-d-Ppg-OH

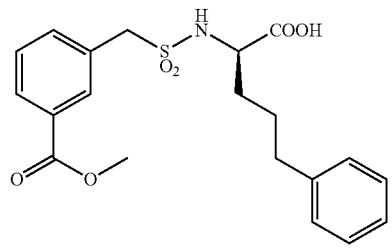

1.3 g (6.72 mmol) of H-d-Ppg-OH (Peptech, Burlington, Mass.) were suspended in 90 ml of dry DCM, and 2 ml (15.7 mmol) of TMS-Cl and 2.6 ml (15 mmol) of DIEA were added. The mixture was refluxed for 1 h, the clear solution was cooled to 0° C., and 2 g (8 mmol) of 3-MeOOC-Bzls-Cl and 2.6 ml of DIEA were added. The mixture was stirred at 0° C. for 15 min and at RT for 1.5 h. The solvent was removed in vacuo, and the residue was dissolved in 700 ml of half-saturated NaHCO$_3$ solution. The mixture was extracted 2× with a little ethyl acetate, and then the aqueous phase was acidified with HCl (pH about 2-3). The mixture is extracted 3× with 150 ml of ethyl acetate, and the combined ethyl acetate phase is washed 2× with 5% KHSO$_4$ solution and 1× with saturated NaCl solution. The organic phase is dried with Na$_2$SO$_4$, and the solvent is removed in vacuo.

Yield: 2.4 g of oil (HPLC: 33.53 min, Start with 20% B)

h) 3-MeOOC-Bzls-d-Ppg-Phe(3-Tfa-Ame)-4-(acetylhydroxyamidino)benzylamide

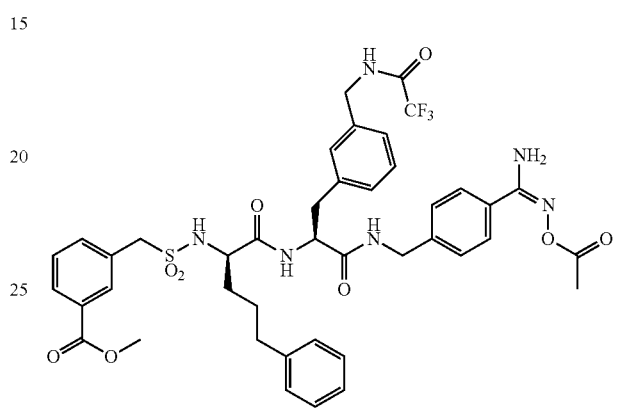

0.605 g (1.5 mmol) of 3-MeOOC-Bzls-d-Ppg-OH and 0.85 g (1.65 mmol) of H-Phe(3-Tfa-Ame)-4-(acetylhydroxyamidino)benzylamide×HCl were dissolved in 40 ml of dry DMF and, at 0° C., 0.63 g (1.65 mmol) of HBTU and 0.6 ml (0.34 mmol) of DIEA were added. The mixture is stirred at 0° C. for 15 min and at RT for a further 3 h. The solvent is removed in vacuo, and the residue is dissolved in ethyl acetate. The ethyl acetate phase is washed 3× with 5% KHSO$_4$ solution, 1× with saturated NaCl solution, 3× with saturated NaHCO$_3$ solution and 2× with saturated NaCl solution. The solvent is removed in vacuo.

Yield: 1.36 g of oil (HPLC: 38.40 min, Start with 20% B)

i) 3-MeOOC-Bzls-d-Ppg-Phe(3-Tfa-Ame)-4-amidinobenzylamide×acetate

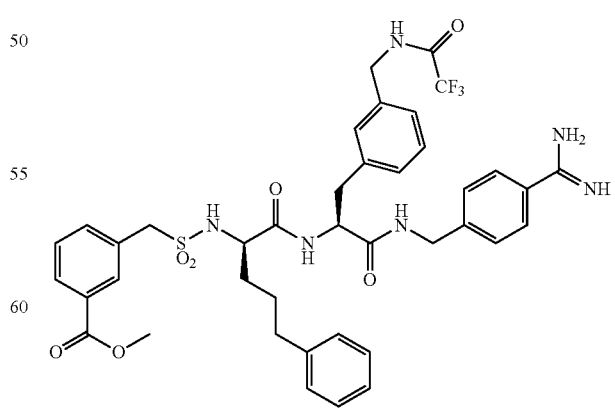

1.3 g of 3-MeOOC-Bzls-d-Ppg-Phe(3-Tfa-Ame)-4-(acetylhydroxyamidino)benzylamide are dissolved in 100 ml of 90% acetic acid and hydrogenated with hydrogen under atmospheric pressure and 150 mg of 10% Pd/C as catalyst overnight. The catalyst is filtered off and the filtrate is concentrated in vacuo.

Yield: 1.2 g of oil (HPLC: 29.45 min, Start with 20% B)

2.2 3-HOOC-Bzls-d-Ppg-Phe(3-Ame)-4-amidinobenzylamide×2 acetate (3)

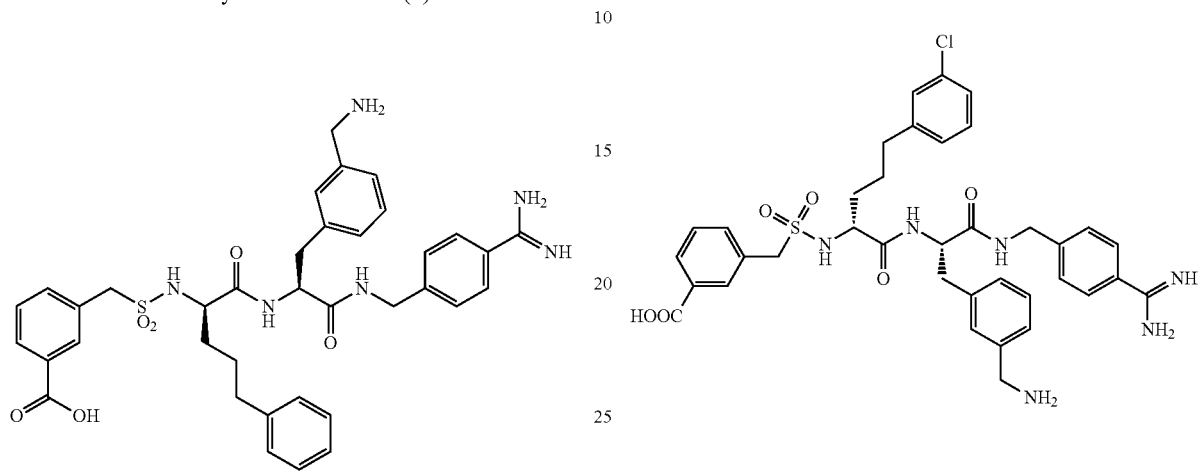

1.2 g of 3-MeOOC-Bzls-d-Ppg-Phe(3-Tfa-Ame)-4-amidinobenzylamide×acetate were stirred in a mixture of 10 ml of dioxane and 10 ml of 1 N LiOH for 1.5 h. The mixture was then neutralized by adding TFA, and the product was purified by preparative reversed-phase HPLC. The product-containing fractions were combined and lyophilized.

Yield: 0.4 g as TFA salt (HPLC: 24.16 min, Start with 10% B)

MS: calculated: 698.29 found: 699.3 (M+H)$^+$

The product was converted into the acetate salt by preparative HPLC by elution with an increasing acetonitrile gradient containing 0.1% acetic acid.

Yield: 0.32 g

Further inhibitors were synthesized in accordance with the above synthesis description, incorporating differently substituted or unsubstituted benzylsulfonyl residues and various P3 amino acids as replacement for d-phenylpropylglycine. Further analogs of d-phenylpropylglycine were synthesized by Heck coupling and incorporated into the P3 position of the inhibitors. The synthesis can be carried out for example as follows:

2.3 Bzls-d-Gly(3-Cl-Phpr)-Phe(3-Ame)-4-Amba×2 TFA (6)

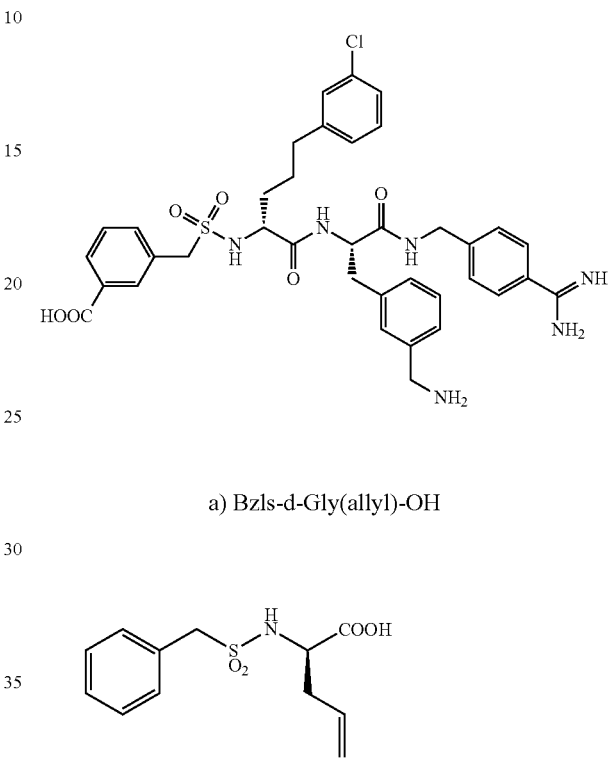

a) Bzls-d-Gly(allyl)-OH 1.0 g (8.68 mmol) of D-allylglycine (Peptech, Burlingtom, Mass.) was suspended in 50 ml of dry DCM, and 2.4 ml (19 mmol) of TMS-Cl and 3.3 ml (19 mmol) of DIEA were added. The mixture was refluxed for 1 h, the clear solution was cooled to 0° C., and 2.35 g (9.55 mmol) of Bzls-Cl and 1.8 ml of DIEA were added. The mixture was stirred at 0° C. for 15 min and at RT for 1.5 h. The solvent was removed in vacuo and the residue was dissolved in 700 ml of half-saturated NaHCO$_3$ solution. The mixture was extracted 2× with ethyl acetate and then the aqueous phase was acidified with HCl (pH about 2-3). The mixture was extracted 3× with 150 ml of ethyl acetate, and the combined ethyl acetate phase was washed 2× with 5% KHSO$_4$ solution and 1× with saturated NaCl solution. The organic phase was dried with Na$_2$SO$_4$, and the solvent was removed in vacuo.

Yield: 2.2 g of oil (HPLC: 21.1 min, Start with 20% B)

method 2h. The resulting intermediate was hydrogenated in analogy to method 2i, but in this case no cleavage of the Cl atom of the P3 amino acid was observed. In the last step, the trifluoroacetyl protective group was cleaved off with LiOH in dioxane in analogy to the final synthesis step in the preparation of compound 3.

HPLC: 29.04 min, Start with 10% B
MS: calculated: 688.26 found: 689.2 (M+H)$^+$

2.4 3-HOOC-Bzls-d-Ppg-Phe(3-Ame)-4-guanidinobenzylamide×2 acetate (4)

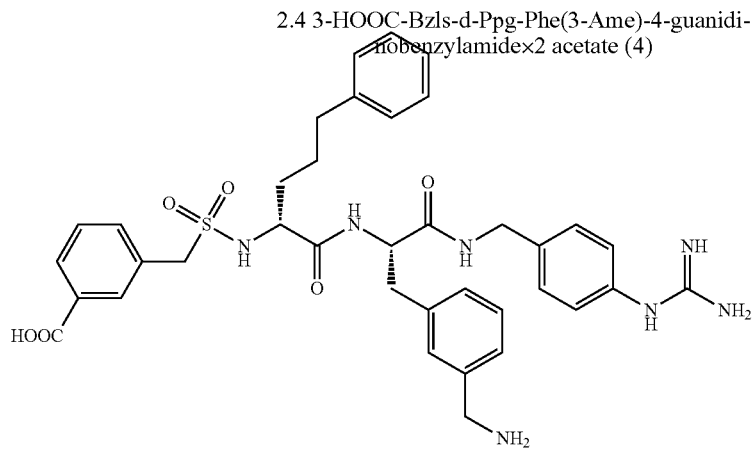

MS (ESI, m/e): 267 [M−1]$^−$ b) Bzls-d-Ala(3-Cl-styryl)-OH

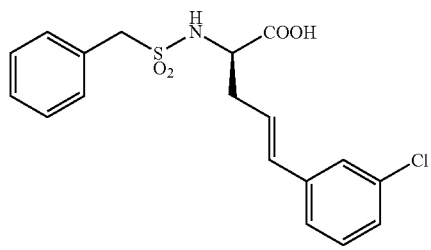

A suspension of 0.476 g (1.48 mmol) of tetra-n-butylammonium bromide, 0.34 g (4.05 mmol) of NaHCO$_3$, 0.32 g (1.34 mmol) of 1-Cl-3-iodobenzene and 9 mg (0.04 mmol) of palladium(II) acetate in a mixture of 2.5 ml of DMF and 2.5 ml of water is stirred at RT for 10 min. A solution of 0.4 g (1.48 mmol) of Bzls-d-Gly(allyl)-OH in 2.5 ml of DMF and 2.5 ml of water is added to this suspension, and the mixture is heated at 45-50° C. for 4-6 days, repeatedly supplementing where appropriate with small amounts of catalyst. The catalyst is filtered off, the solvent is removed in vacuo, and the residue is suspended in 50 ml of 5% KHSO$_4$ solution. The mixture is extracted 3× with 15-20 ml of ethyl acetate each time, and the combined ethyl acetate phase is washed 2× with 5% KHSO$_4$ solution and 1× with saturated NaCl solution. The organic phase is dried with Na$_2$SO$_4$, and the solvent is removed in vacuo. The residue (0.55 g of dark oil) is purified by flash chromatography on silica gel 60 (40-63 μm) (gradient 0-20% methanol in DCM).

Yield: 0.23 g (HPLC: 39.7 min, Start with 20% B)

Further assembling of the inhibitor took place in analogy to the synthesis described for inhibitor 1. The intermediate 2.2.b was coupled to the intermediate 2d (H-Phe(3-Tfa-Ame)-4-(acetylhydroxyamidino)benzylamide×HCl) in analogy to method 2h. Compound 4 was also synthesized in analogy to the above synthesis description 2.2a-i, using p-nitrobenzylamide for step c) instead of 4-(acetylhydroxyamidino)benzylamide. The nitrobenzylamide residue was reduced to the p-aminobenzylamide in analogy to step 2.2i with methanol/THF (1:1) as solvent. The guanylation of the p-aminobenzylamide residue took place with commercially available 1,3-di-Boc-2-(trifluoromethylsulfonyl)guanidine (Fluka) as guanylating reagent. For this purpose, the intermediate from the reduction was dissolved in dioxane and stirred with the guanylating reagent and TEA at 50° C. for 1 day. After the solvent has been evaporated, the Boc protective groups were cleaved off with TFA in a known manner. After the solvent had been evaporated, the trifluoroacetyl protective group and the methyl ester were cleaved off in the last step using LiOH in dioxane in analogy to the final synthesis step in the preparation of compound 3.

HPLC: 25.1 min, Start with 10% B
MS: calculated: 713.3 found: 714.4 (M+H)$^+$

2.5 Pegylated Compounds

Further inhibitors to which polyethylene glycol (PEG) chains of varying chain length were covalently coupled were synthesized by standard processes. Commercially available PEG derivatives from Fluka, Nektar Therapeutics or Rapp Polymere with different average molecular weights (1000 Da, 2000 Da, 5000 Da, 10 000 Da) were used for all the syntheses. The PEG derivatives used are protected as methyl ether at one end and modified at the other end with a propionic acid or succinic acid residue activated as N-hydroxysuccinimide ester. It was thus possible to react these activated PEG derivatives with a free amino group of the inhibitor (see synthesis schemes 1 to 5). In the last step, the TFA protective group was cleaved off by mixing with 1 N NaOH solution, and the products were purified by ion exchange chromatography on Fractogel® CE (Merck KGaA, Darmstadt) using an ammonium acetate gradient and were lyophilized 3× from water. The following examples yielded inhibitors with a PEG chain of an average mass of about 1000, 2000, 5000 or 10 000 Da.

Scheme 1:
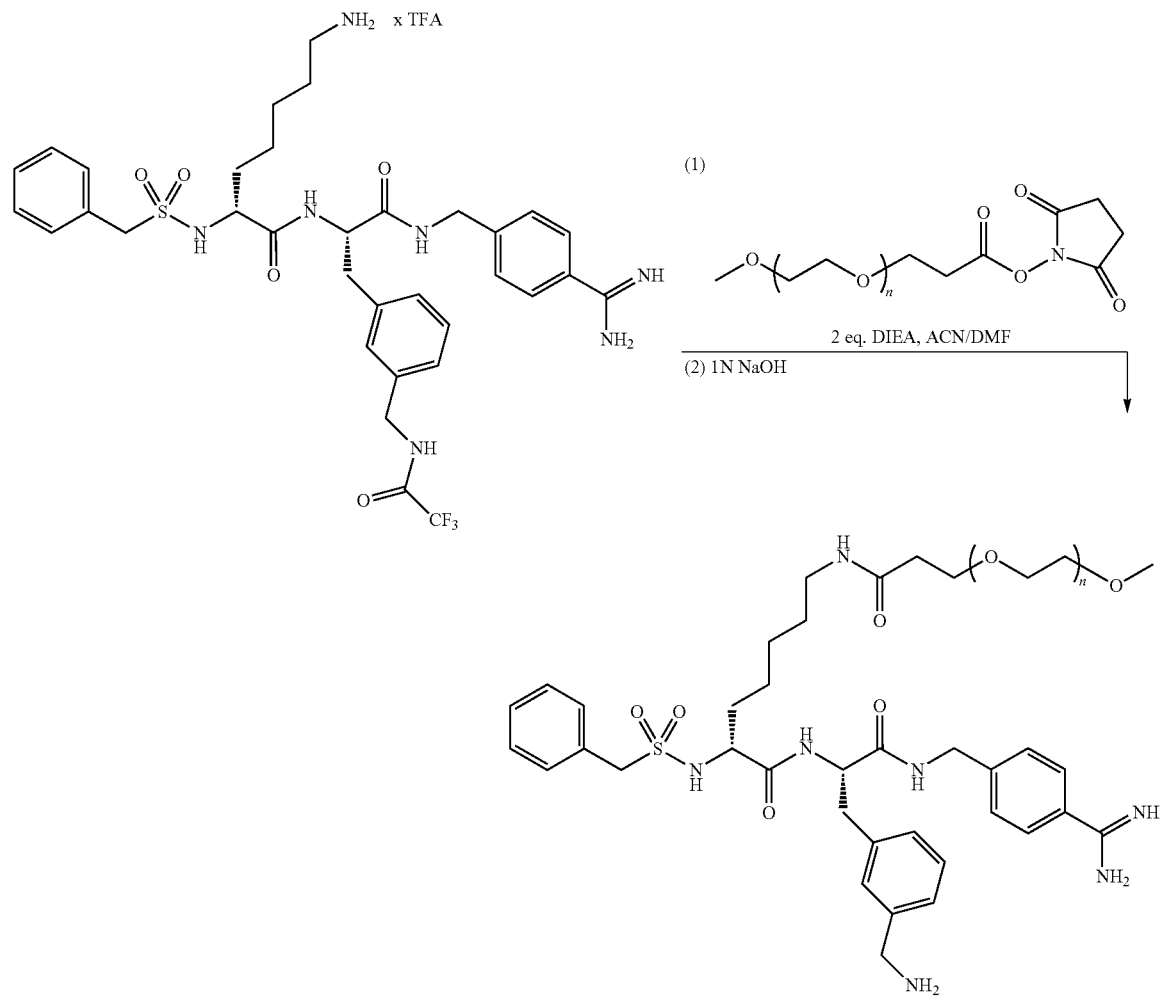

Scheme 2:
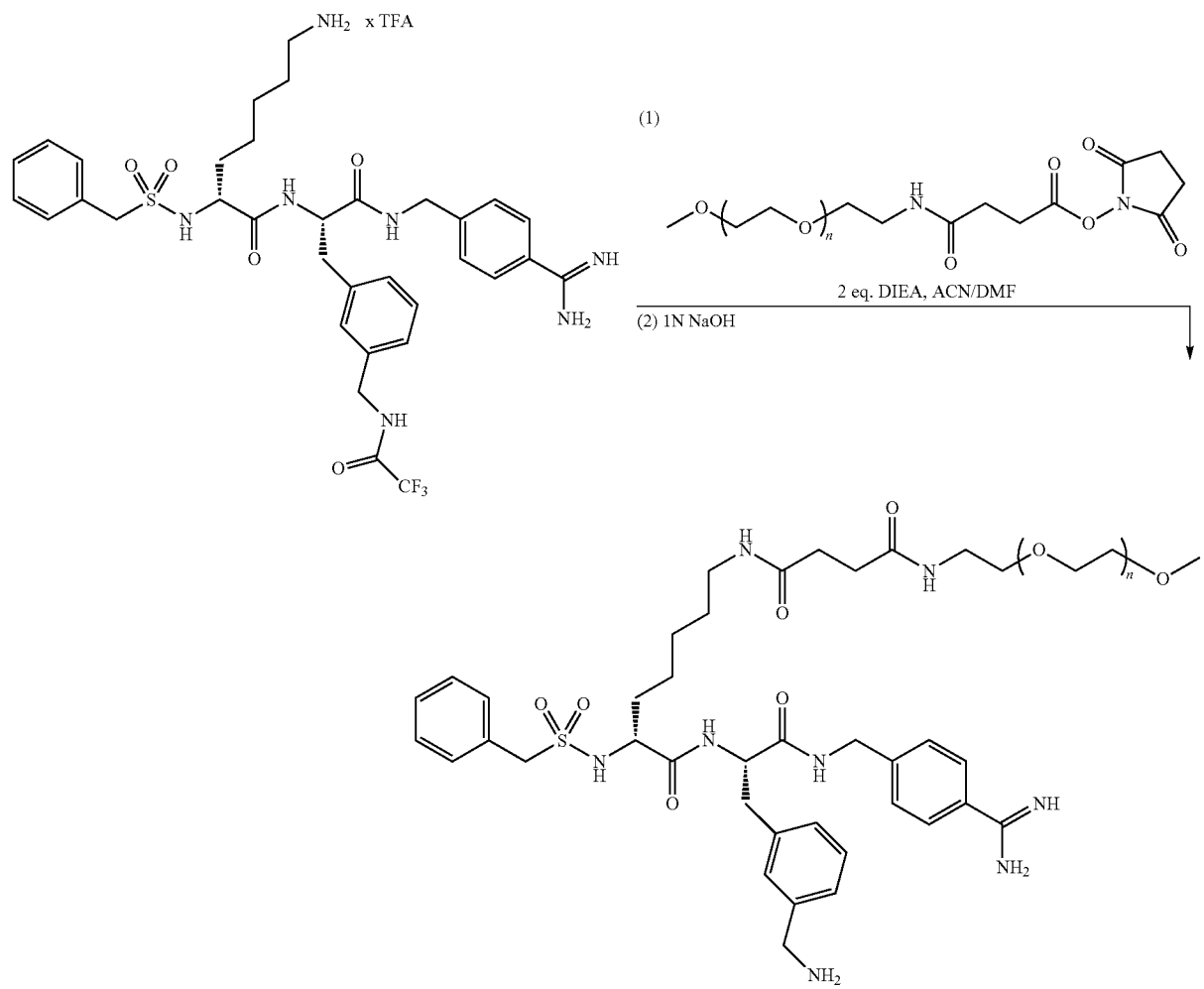

Scheme 3:
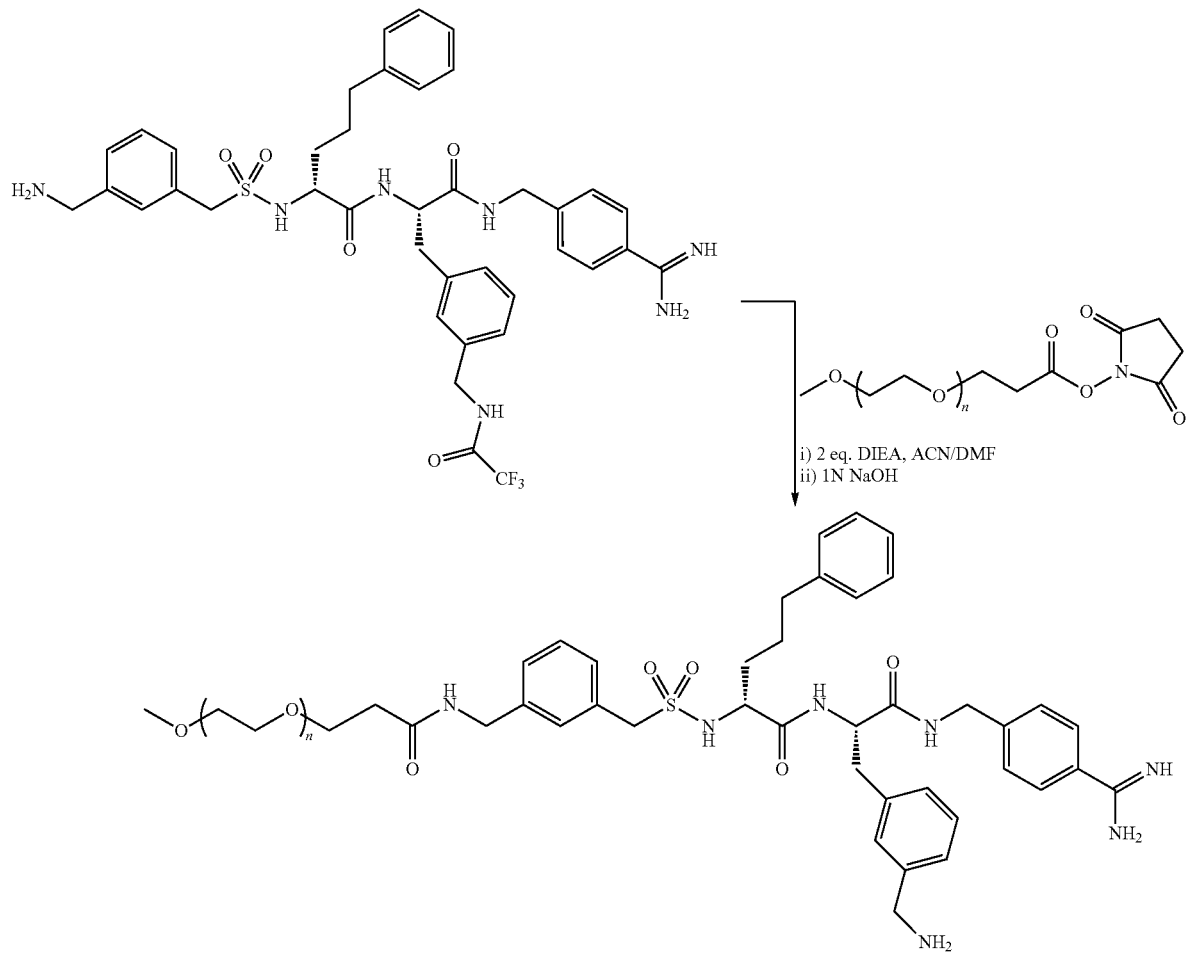

Scheme 4:
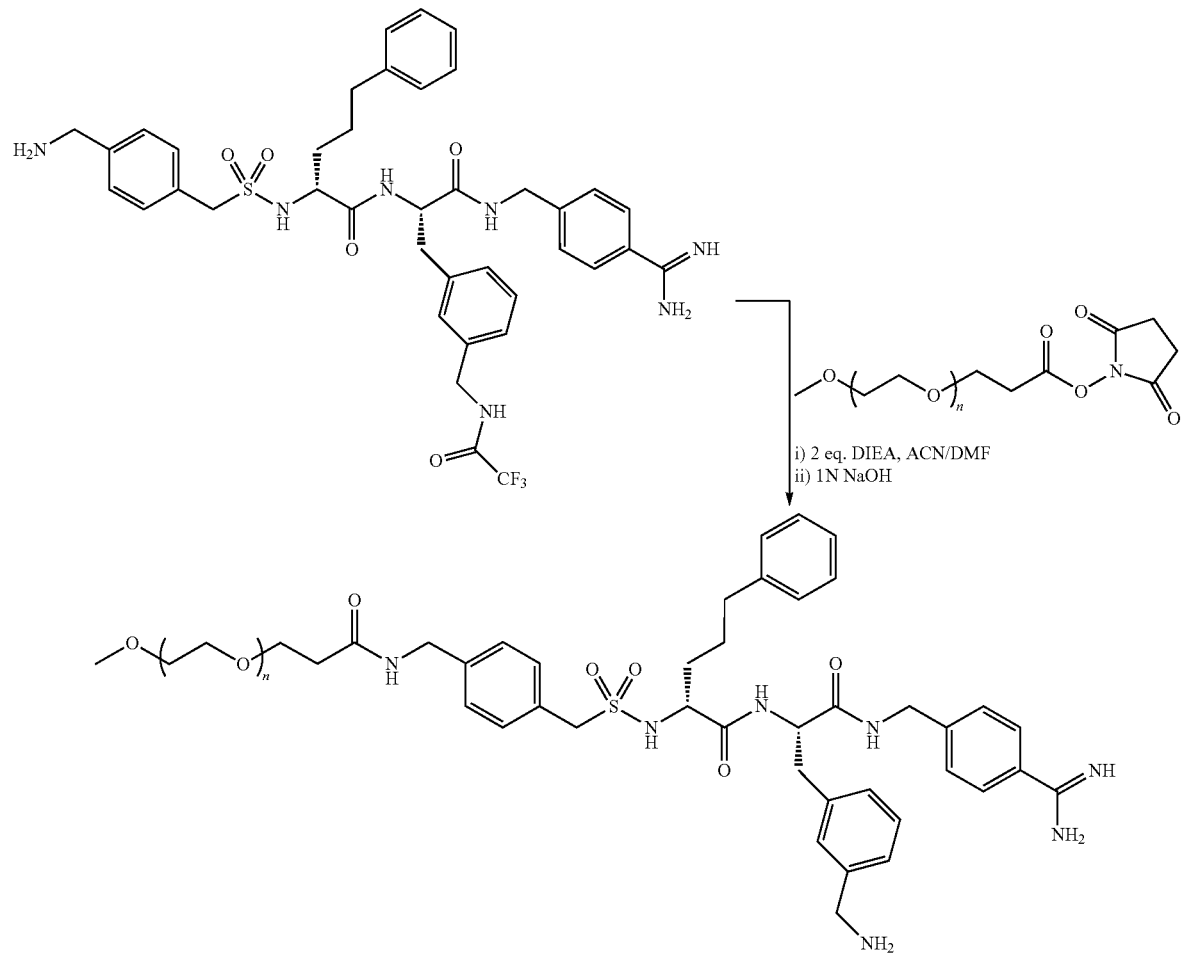
Scheme 5:
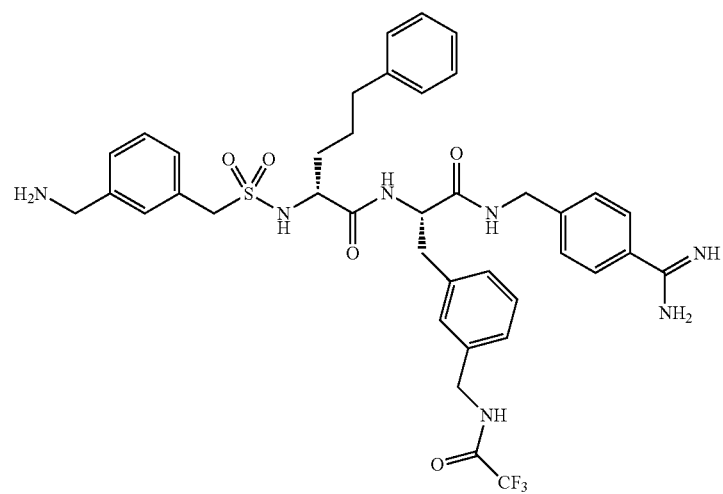

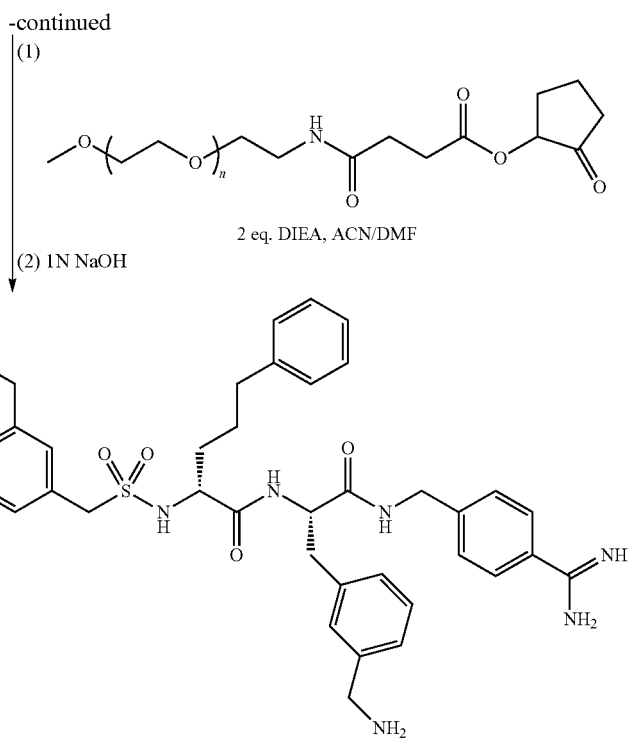

The compounds synthesized in the examples are summarized, including their inhibition constants, in the table below.

3. Determination of the Inhibition Constants for Plasmin and PK ($K_i$ Values in nM)

The inhibitory effect for the individual enzymes was determined in analogy to a previously disclosed method (Stürzebecher et al., 1997).

The reactions to determine the inhibition of human plasmin and human plasma kallikrein were carried out in the following mixture at 25° C.:

200 µl of TBS (0.05 M trishydroxymethylaminomethane; 0.154 M NaCl, 2% ethanol, pH 8.0; contains the inhibitor)

25 µl of substrate (2 mM, 1 mM and 0.67 mM tosyl-Gly-Pro-Lys-pNA=Chromozym PL from LOXO for plasmin and 2 mM, 1 mM and 0.5 mM H-D-Pro-Phe-Arg-pNA=S2302 from Chromogenix for PK, dissolved in $H_2O$)

50 µl of enzyme solution (plasmin from Calbiochem: 2-5 mU/ml in 0.154 M NaCl+0.1% BSA m/v+25% v/v glycerol; plasma kallikrein from Enzyme Research Lab.: 20-60 ng/ml in 0.154 M NaCl+0.1% BSA m/v)

For zero order kinetics, the reaction was stopped after 20 min by adding 25 µl of acetic acid (50% v/v), and the absorption at 405 nm was determined using a Microplate Reader (Multiscan Ascent, from Thermo). In the case of pseudo-first order kinetics, the reaction rates in the equilibrium state were ascertained by recording the reaction kinetics. The $K_i$ values were ascertained either in accordance with Dixon (1953) by linear regression using a computer program or by parameter fitting in accordance with the rate equation for competitive inhibition. The $K_i$ values are the average of at least two determinations.

Table $K_i$ values: A means <10 nM, B means <100 nM, C means <1000 nM and D means >1000 nM

| | | | $1^{st}$ group | | | |
|---|---|---|---|---|---|---|
| No. | Mass (found/calculated) | HPLC % AN | Plasmin $[K_i]$ | PK $[K_i]$ | Xa $[K_i]$ | Thrombin $[K_i]$ |
| 1 | 655.3/654.3 | 37.4 | A | A | B | C |
| 2 | 699.5/698.3 | 33.6 | A | A | B | C |
| 3 | 699.3/698.3 | 34.1 | A | A | B | D |
| 4 | 714.4/713.3 | 35.1 | B | A | D | D |
| 5 | 717.3/716.3 | 34.9 | A | A | B | D |
| 6 | 689.2/688.3 | 39.8 | A | A | B | C |
| 7 | 689.3/688.26 | 41.9 | A | A | A | B |
| 8 | 689.3/688.26 | 39.0 | A | A | B | B |
| 9 | 669.3/668.3 | 39.3 | A | A | B | C |
| 10 | 685.6/684.3 | 37.2 | A | A | B | C |
| 11 | 723.2/722.3 | 41.6 | A | A | A | C |
| 12 | 739.4/738.3 | 44.4 | A | A | B | C |
| 13 | 683.3/682.3 | 41.9 | B | A | B | C |
| 14 | 703.3/702.3 | 40.7 | A | A | B | C |
| 15 | 677.3/676.3 | 37.4 | A | A | B | B |
| 16 | 721.2/720.3 | 34.3 | A | A | C | C |
| 17 | 677.3/676.3 | 37.7 | A | A | B | C |
| 18 | 721.1/720.3 | 35.6 | A | A | B | D |
| 19 | 721.2/720.3 | 34.6 | A | A | C | C |
| 20 | 633.8/632.3 | 36.1 | A | A | B | C |
| 21 | 661.4/660.3 | 41.5 | A | A | B | C |
| 22 | 703.4/702.3 | 38.4 | A | A | B | A |
| 23 | 747.3/746.3 | 36.3 | A | A | B | B |
| 24 | 657.3/656.3 | 29.1 | A | A | A | C |
| 25 | 747.3/746.3 | 36.3 | A | A | B | D |
| 26 | 671.4/670.3 | 30.7 | A | A | A | C |
| 27 | 642.3/641.3 | 42.4 | A | A | A | C |
| 28 | 655.4/654.3 | 37.0 | A | A | C | C |
| 29 | 699.4/698.3 | 31.8 | A | A | C | C |
| 30 | 699.4/698.3 | 34.2 | A | A | C | D |
| 31 | 669.4/668.3 | 36.9 | A | B | C | B |
| 32 | 616.2/615.3 | 35.3 | A | B | C | B |
| 33 | 660.3/659.3 | 31.9 | A | B | C | D |

-continued

| | | 1st group | | | | |
|---|---|---|---|---|---|---|
| No. | Mass (found/calculated) | HPLC % AN | Plasmin $[K_i]$ | PK $[K_i]$ | Xa $[K_i]$ | Thrombin $[K_i]$ |
| 34 | 640.4/639.3 | 52.7 | A | A | C | B |
| 35 | 684.3/683.3 | 48.6 | A | A | C | C |
| 36 | 684.3/683.3 | 49.8 | A | A | B | C |
| 37 | 647.9/646.3 | 39.3 | B | B | B | B |
| 38 | 660.6/659.4 | 39.3 | A | B | B | A |
| 39 | 641.5/640.3 | 36.1 | A | A | B | A |
| 40 | 685.5/684.3 | 32.2 | A | A | C | B |
| 41 | 657.5/656.3 | 40.0 | A | A | C | B |
| 42 | 701.5/700.3 | 35.4 | B | A | D | C |
| 43 | 619.2/618.3 | 35.1 | A | B | B | A |
| 44 | 627.2/626.3 | 33.7 | B | B | B | B |
| 45 | 638.8/637.3 | 30.6 | A | A | C | B |
| 46 | 638.7/638.2 | 34.0 | A | A | C | B |
| 47 | 643.3/642.3 | 28.0 | A | A | A | A |
| 48 | 641.4/640.3 | 34.4 | A | A | A | C |
| 49 | 641.4/640.3 | 33.7 | A | A | B | B |
| 50 | 685.3/684.3 | 31.5 | A | A | B | C |
| 51 | 641.3/640.3 | 33.9 | A | A | A | A |
| 52 | 685.2/684.3 | 31.5 | A | A | A | B |
| 53 | 657.3/656.3 | 36.7 | A | A | A | B |
| 54 | 701.4/700.3 | 34.4 | A | A | B | D |
| 55 | 657.4/656.3 | 37.1 | A | A | A | B |
| 56 | 701.5/700.3 | 34.9 | A | A | A | C |

| | | 2nd group: | | | | |
|---|---|---|---|---|---|---|
| # | MS (found/calculated) | HPLC % AN | Plasmin | PK | Xa | Thrombin |
| 57 | 708.6/707.38 | 36.5 | A | A | B | D |
| 58 | 752.4/751.4 | 31.9 | B | A | C | D |
| 59 | 608.4/607.3 | 41.0 | B | A | C | D |
| 60 | 666.8/665.3 | 34.4 | B | A | C | D |
| 61 | 566.5/565.3 | 21.5 | B | A | D | D |
| 62 | 694.9/693.4 | 34.6 | A | A | C | C |
| 63 | 623.6/622.3 | 34.8 | A | A | C | C |
| 64 | 681.7/680.3 | 34.7 | A | A | D | D |
| 65 | 667.7/666.3 | 30.1 | B | A | C | D |
| 66 | 681.3/680.8 | 34.4 | A | A | B | D |
| 67 | 667.5/666.8 | 30.1 | A | A | B | D |
| 68 | 567.8/566.3 | 25.4 | B | A | D | D |
| 69 | 625.6/624.3 | 26.1 | B | A | D | D |
| 70 | 611.9/610.3 | 21.0- | B | A | D | D |
| 71 | 623.7/622.3 | 33.9 | A | A | D | C |
| 72 | 567.7/566.3 | 24.6 | B | B | D | D |
| 73 | 637.6/636.3 | 35.1 | B | B | C | B |
| 74 | 581.5/580.3 | 25.2 | B | B | D | D |
| 75 | 636.5/635.3 | 33.2 | B | B | C | C |
| 76 | 580.6/579.3 | 23.1 | B | B | D | D |
| 77 | 650.6/649.3 | 35.0 | A | A | C | B |
| 78 | 594.6/593.3 | 25.1 | B | A | D | D |

PEGylated Compounds:

| No. | Mass (found/calculated) | HPLC % AN | Plasmin $[K_i]$ | PK $[K_i]$ | Xa $[K_i]$ | Thrombin $[K_i]$ |
|---|---|---|---|---|---|---|
| 79a | ~1000 Da | 34.9 | A | A | C | D |
| 79b | ~2000 Da | 39.4 | A | — | — | — |
| 79c | ~5000 Da | 43.6 | A | A | B | D |
| 79d | ~10000 Da | 45.4 | A | A | C | D |
| 80 | ~10000 Da | 45.8 | A | A | B | D |
| 81 | ~10000 Da | 46.4 | A | A | C | C |
| 82 | ~10000 Da | 46.0 | A | A | C | C |
| 83 | ~10000 Da | 45.2 | A | A | C | C |

Results:

1. The $K_i$ value of the plasmin inhibition was generally <100 nM. The $K_i$ value was distinctly lower than 100 nM in particular for compounds with cyclic structures at $R_2$ and $R_3$ and was below about 10 nM for compounds with an aromatic carbocyclic system on $R_2$ and $R_3$. Surprisingly there is a particularly large number of compounds of the invention with a $K_i$ value below 5 nM, e.g. compounds Nos. 1-11, 13, 14, 16-18, 20-33, 35, 38, 39, 46 and 48-56.
2. The $K_i$ value of the plasma kallikrein inhibition was likewise generally <100 nM. The $K_i$ value was distinctly less than 100 nM in particular for compounds with an aromatic carbocyclic system at $R_2$ and $R_3$. Surprisingly, there is a particularly large number of compounds of the invention with a $K_i$ value below 1 nM, e.g. compounds Nos. 1-3, 5-6, 8-25, 27, 29, 34-36, 39, 40, 49-57, 59-61, 64, 65 and 68-70.
3. It was possible by incorporating homotyrosine or pyridine and the corresponding N-oxides as heterocycles in P3 to reduce distinctly the selectivity for FXa.
4. It was generally possible to achieve a distinct reduction in the inhibition of thrombin when $R_1$ represents a 3-COOH group. A further reduction in the inhibition of thrombin was achieved when $R_4$ represents a fluorine atom, especially in ortho position.
5. A particularly suitable compound has proved to be the compound of formula (I) with i=0 and without $R_4$ with the following residues:

| Compound No. | $R_1$ | $R_2$ | p | $R_3$ | o |
|---|---|---|---|---|---|
| 3 | 3-COOH | 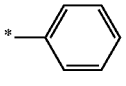 | 3 | 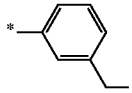 | 1 |

4. Antifibrinolytic and Anticoagulant Properties of Compound No. 3

EXPERIMENTAL

In the in vitro studies described below, the antifibrinolytic efficacy of Compound No. 3, aprotinin, and tranexamic acid was compared. In addition, the anticoagulant effects of Compound No. 3 were assessed through measurement of plasma and whole blood clotting times and thrombin generation.

Aprotinin and tranexamic acid were purchased from SIGMA (Schnelldorf, Germany). Human factor Xa, factor XIa, factor XIIa, thrombin, and plasma kallikrein were purchased from Enzyme Research Laboratories, and human plasmin from Chromogenix (both via Haemochrom, Essen, Germany). Various synthetic peptide chromogenic substrates used for determination of inhibition constants were obtained from Pentapharm (Basel, Switzerland), Roche (Mannheim, Germany), and Chromogenix: Chromozyme PL for plasmin, S2302 for plasma kallikrein, Pefachrome FXa for factor Xa, Chromozym XII for FXIIa, Pefachrom tPA for thrombin, and Pefachrome PCa for factor XIa. Tissue-type plasminogen activator was obtained from Boehringer Ingelheim (Ingelheim, Germany). INTEM, EXTEM and STARTEM reagents and disposables for ROTEM® measurements were obtained from Pentapharm (Munich, Germany).

Venous blood was withdrawn from the antecubital vein from healthy volunteers after written informed consent in accordance with local and federal guidelines with approval of the local review board (Ethikkommission, Klinikum Charité, Sauerbruchweg 5, 10117 Berlin). The blood was mixed with 0.11 mol/L sodium citrate (1:10). For ROTEM® analysis, whole citrated blood was used within 8 h after collection. Platelet-rich plasma (PRP) was prepared from citrated blood by centrifugation at 330×g for 10 min at room temperature, platelet-poor plasma (PPP) was collected following centrifugation at 1220×g for 12 min. The PRP was then adjusted to $3 \times 10^8$ platelets per mL using the autologous PPP. PRP was maintained at room temperature for less than 4 h before analysis. The remaining PPP was subjected to a high-speed centrifugation at 40,000×g for 30 min at 4° C. to remove any particulate material and was then stored at −70° C. until use.

Statistics

Statistical analyses were performed using SigmaPlot® 9.0 (SSI, San Jose, Calif.) and SPSS software (SPSS Inc., Chicago, Ill., USA). Data are presented as mean±standard deviation (SD) or median with 25% and 75% percentile for non-normal distributed measurements.

Differences among groups were assessed by non-parametric Kruskal-Wallis test followed by pairwise post-hoc comparisons using Mann-Whitney-U test. Assessment of differences between two related samples was conducted by Wilcoxon signed ranks test. To reduce multiple test issues, Bonferroni correction of p-values was applied within each many-one group comparison (several concentrations versus one control) as well in any pairwise post-hoc comparison. A p-value <0.05 was considered to outline statistical significance.

(A) Inhibition Constants ($K_i$) of Compound No. 3 and Aprotinin Against Human Serine Proteases Experimental Design Inhibition of purified human serine proteases by Compound No. 3 and aprotinin was studied using the established methods described herein in Example 3 (i.e., Stürzebecher et al., 1997). Enzyme kinetic experiments were carried out in 96-well flat-bottom plates (Brand, Wertheim, Germany) in 50 mM Tris-HCl pH 8.0, 154 mM NaCl in the presence of different substrate and inhibitor concentrations. Steady-state velocities of substrate conversion were obtained from progress curves generated by continuous monitoring of the absorbance at 405 nM with a microplate reader (Multiskan Ascent, Thermo Electron Corporation, Dreieich, Germany). For determination of $K_i$ values below 1 nM, measurements were performed in acrylic cuvettes (Brand, Wertheim, Germany) using a UV/VIS spectrophotometer (Specord® M-400, Carl Zeiss, Jena, Germany). Inhibition constants ($K_i$) were calculated from non-linear fits of individual data sets to the Michaelis-Menten equation for competitive inhibitors using an enzyme kinetic analysis software (SIGMA Plot® 9.0 Enzyme Kinetics Module, SSI, San Jose, Calif.). Dixon plot analysis was applied to confirm the competitive inhibition mode.

Results

The results of these enzyme kinetic experiments are summarized in Table 1. Compound No. 3 and aprotinin show comparable inhibition of plasmin, whereas Compound No. 3 displayed substantially stronger inhibition of plasma kallikrein (2000-fold), FXa (1200-fold) and FXIa (100-fold).

|  | Compound No. 3 $K_i$ [nM] | Aprotinin $K_i$ [nM] |
|---|---|---|
| Plasmin | 2.2 ± 0.2 | 4.2 ± 0.4 |
| Plasma kallikrein | 0.019 ± 0.003 | 38 ± 2 |

-continued

|  | Compound No. 3 $K_i$ [nM] | Aprotinin $K_i$ [nM] |
|---|---|---|
| FXa | 45 ± 5 | 55,600 ± 400 |
| FXIa | 18 ± 1 | 1840 ± 40 |
| FXIIa (alpha) | 5200 ± 400 | 5400 ± 100 |
| Thrombin | 1700 ± 200 | 76,000 ± 2,000 |

(B) Establishment of Antifibrinolytic Potency

Experimental Design

The antifibrinolytic activity of Compound No. 3 in comparison to aprotinin and tranexamic acid was investigated in plasma and whole blood assays. In both assays, tissue factor was added to initiate rapid clot formation via the extrinsic pathway which produces a clot that remains stable for several hours under normal conditions. Supplementation of plasma or whole blood with tissue-type plasminogen activator (t-PA) before stimulation results in activation of endogenous plasminogen and thus fibrinolysis while the initial clot formation is not impaired. The amount of t-PA added was found to determine lysis time. A final concentration of 50 U/mL and 100 U/mL in plasma and whole blood, respectively, was chosen to achieve complete lysis within about 60 min. In the presence of antifibrinolytics, clot lysis is delayed in a concentration-dependent manner.

a) Plasma fibrinolysis assay: Inhibition of fibrinolysis in plasma was examined using a turbidometric method in 96-well flat-bottom plates. The time course of clot formation and lysis, reflected by an initial increase and subsequent decrease in turbidity, was recorded by continuously measuring the optical density (OD) at 405 nm. Similar models have been used widely to study the clot lysis process in human plasma (Kim et al., *J. Thromb. Haemost.* 5: 1250-6, 2007) as well as its inhibition by antifibrinolytic drugs (Sperzel et al., *J. Thromb. Haemost.* 5: 2113-8, 2007). Frozen and thawed human plasma (PPP) was pre-incubated with test compound or vehicle (Owren's Veronal buffer) for 5 min at 37° C. Coagulation and subsequent fibrinolysis was started by adding tissue factor (Innovin®, Dade Behring at 1:9000 final dilution), $CaCl_2$ (12 mM final concentration) and t-PA (50 U/mL final concentration) simultaneously to the wells. OD at 405 nm was monitored every 45 s for 180 min at 37° C. with a microplate reader (POLARstar OPTIMA, BMG Labtech, Offenburg, Germany). Fibrinolysis was quantified as the relative decrease in OD at 45 min after the maximum OD was reached. Compound No. 3 and aprotinin were each tested at concentrations of 60, 100, 200, 300, 600, 1000, and 3000 nM, tranexamic acid was tested at concentrations of 600, 1000, 3000, 6000, 10,000, 20,000, and 30,000 nM to cover the complete concentration-response for each compound. These aprotinin concentrations range between 2.8 and 140 kallikrein inhibiting units (KIU)/mL based on the conversion factor of 7.14 KIU/μg. Concentration-response curves were established by plotting percentage fibrinolysis versus test compound concentration.

b) Whole blood fibrinolysis assay: Fibrinolysis in whole blood was studied with rotational thromboelastometry (Luddington, *Clin. Lab. Haematol.* 27: 81-90, 2005) using a computerized, multi-channel ROTEM® instrument (Pentapharm, Munich, Germany) (Ganter et al., *Anesth. Analg.* 106: 1366-75, 2008). Activation of test samples accelerated the measurement process and enhanced reproducibility compared with conventional thromboelastography. To allow observation of fibrinolysis, ROTEM® analysis with tissue factor activation (EXTEM) was modified through addition of t-PA (Nielsen et al. *Blood Coagul Fibrinolysis* 17: 75-81, 2006). Citrated blood was pre-incubated at 37° C. for 5 min with test compound or saline before tissue factor, $CaCl_2$ and t-PA (100 U/mL final concentration) were added to start the reaction. Fibrinolysis was determined by measuring loss of clot strength with time and was recorded as Ly60 (percentage reduction of the maximum amplitude at 60 min after the onset of clotting). In control samples without inhibitor, clots were lysed completely within 60 min, such that Ly60 was above 90%. By plotting Ly60 versus test compound concentration, $IC_{50}$ values for each compound were calculated.

Results

The effect of Compound No. 3, aprotinin, and tranexamic acid on the dynamics of clot formation and lysis in whole blood ROTEM® is depicted in FIGS. 1A-1K. All three agents have equivalent antifibrinolytic efficacy; however, potency differs significantly: Compound No. 3 and aprotinin largely suppress clot lysis at concentrations of 600 and 1000 nM, respectively, while tranexamic acid requires concentrations between 3000 and 10,000 nM for effective inhibition. Both Compound No. 3 and aprotinin produce a concentration-dependent decrease of Ly60 (FIG. 2A). The concentrations resulting in 50% suppression of clot lysis ($IC_{50}$, median [25%; 75% percentile]) are 150 [115; 210] nM and 345 [304; 497] nM (corresponding to 16 KIU/mL) for Compound No. 3 and aprotinin, respectively ($p<0.001$ for comparison of Compound No. 3 vs. aprotinin). Tranexamic acid also reduced clot lysis in a concentration-dependent manner, although with substantially lower potency ($IC_{50}=2750$ [1875; 3225] nM, $p<0.001$ vs. Compound No. 3, $p=0.002$ vs. aprotinin).

Similar results were obtained when human plasma was used instead of whole blood as shown in FIG. 2B. Compound No. 3 and aprotinin exhibit comparable potency on t-PA-induced fibrinolysis in plasma, with $IC_{50}$ values of 315 [135; 506] nM and 327 [280; 537] nM (15 KIU/mL), respectively ($p=0.9$ for comparison of Compound No. 3 vs. aprotinin). Tranexamic acid exhibits an $IC_{50}$ of 4225 [3050; 4280] nM ($p<0.001$ vs. Compound No. 3 and aprotinin), indicating its significantly lower antifibrinolytic potency.

(C) Assessment of Anticoagulant Potency

Experimental Design

Since Compound No. 3 inhibits multiple proteases of the coagulation system, we investigated possible anticoagulant properties using established tests in vitro. Whereas tissue factor is the physiologic trigger of coagulation, both extrinsic and contact-mediated stimulation contribute to hemostatic activation under conditions like CPB (Boisclair et al. *Blood* 82: 3350-7, 1993 and Edmunds et al., *Ann. Thorac. Surg.* 82: 2315-22, 2006). We therefore studied the impact of Compound No. 3 and aprotinin on coagulation in plasma and whole blood following both intrinsic and extrinsic stimulation. Tranexamic acid has no influence on other proteases than plasminogen and, therefore, is not included in these experiments.

a) Plasma coagulation times: Prothrombin time and activated partial thromboplastin time were determined after human plasma (PPP) was supplemented with test compound solution or saline using a conventional coagulation analyzer (Sysmex CA-560, Dade Behring). Reagents used were Innovin® (extrinsic activator containing tissue factor) for prothrombin time and Actin® FSL (contact activator containing ellagic acid and phospholipids) for activated partial thromboplastin time, both from Dade Behring (Eschborn, Germany).

b) Whole blood coagulation assay: The influence on whole blood clotting was assayed with rotational thrombelastometry (Ganter et al., *Anesth. Analg.* 106: 1366-75, 2008) using ellagic acid (INTEM reagent) as activator of the intrinsic system or tissue factor (EXTEM reagent) as extrinsic coagulation activator. Following a 5-min pre-incubation with test compounds or saline, citrated human blood was subjected to ROTEM® analysis according to the manufacturer's instructions. ROTEM® clotting time (equal to reaction time, r) and maximum clot strength (equal to maximum amplitude) were obtained as coagulation parameters.

c) Thrombin Generation Assay: The impact of Compound No. 3 and aprotinin on thrombin generation was studied in PRP using the commercially available Technothrombin® TGA kit (Technoclone, Vienna, Austria). This method allows assessment of the dynamics of thrombin generation, i.e. initiation, propagation, and inactivation phases, including the contribution of platelet function to the clotting process (Hemker et al., *Pathophysiol. Haemost. Thromb.* 33: 4-15, 2003). PRP was spiked with test compounds at different concentrations and pre-warmed to 37° C. in a black 96-well flat-bottom plate (Nunc, Wiesbaden, Germany). Thrombin generation was then initiated by adding a mixture of activator and fluorogenic thrombin substrate. Two different activators were used; a tissue factor-containing reagent provided by the manufacturer for extrinsic stimulation, and Actin FSL® (Dade Behring, Eschborn, Germany) at 1:120 final dilution for intrinsic stimulation of thrombin generation. Starting immediately after addition of reagents, fluorescence was recorded every 60 s for 120 min using the BMG POLARstar microplate reader (BMG Labtech, Offenburg, Germany) set at 390 nm excitation and 460 nm emission maintaining a temperature of 37° C. Data analysis was performed with the Technothrombin® software provided by Technoclone. A typical thrombin generation curve is generated by plotting the first derivative (dF/dt) of the original fluorescence versus time curve and comparing it to a standard run containing known amounts of thrombin in buffer. From these curves representing the time course of thrombin activity the following parameters are derived: the lag phase (in min) from time zero until the start of thrombin generation, peak thrombin level (in nM) and the area under the thrombin generation curve (endogenous thrombin potential, in nM*min).

Results

In addition to its inhibition of plasma kallikrein, Compound No. 3 also affects factors Xa and XIa. Hence, a significant prolongation of plasma and whole blood coagulation times was observed in the presence of Compound No. 3 at antifibrinolytic concentrations ranging from 100 to 1000 nM (see FIG. 3). These effects were more pronounced upon intrinsic activation—reflected in activated partial thromboplastin time and INTEM results—compared to tissue factor activation—represented by prothrombin time and EXTEM clotting time. Aprotinin had almost no influence on plasma or whole blood coagulation at equivalent concentrations (see FIG. 3). A marked prolongation of both activated partial thromboplastin time and intrinsic ROTEM® clotting times occurred at higher aprotinin concentrations whereas extrinsic coagulation was not affected (data not shown).

Neither Compound No. 3 nor aprotinin impaired clot strength—reflected in ROTEM® maximum amplitude—in any of the ROTEM® assays over the concentration range tested (data not shown).

Compound No. 3 also had a similar effect on thrombin generation following both intrinsic and extrinsic activation that was statistically significant compared to aprotinin as illustrated in FIGS. 3 and 4A-F. A concentration-dependent delay in the onset of thrombin generation as well as a reduction in the peak thrombin level was observed whereas there was no impact on endogenous thrombin potential in the presence of 100 to 1000 nM Compound No. 3.

Discussion of Examples 4A-C

This study demonstrates the efficacy and potency in vitro of the synthetic, small molecule direct serine protease inhibitor Compound No. 3. The findings are summarized as follows: First, Compound No. 3 and aprotinin have almost similar nanomolar potency (2.3 vs. 4.2 nM) regarding inhibition of plasmin enzymatic activity. Second, consistent with $K_i$ data, Compound No. 3 and aprotinin display similar nanomolar potencies at inhibiting clot lysis in whole blood ($IC_{50}$ of 150 vs. 345 nM) and plasma ($IC_{50}$ of 315 vs. 327 nM), both drugs being ~10-fold more potent than tranexamic acid. Third, Compound No. 3 and aprotinin, but not tranexamic acid, display anticoagulant properties, with Compound No. 3 being more potent than aprotinin as assessed by ROTEM®, global plasma coagulation tests, and inhibition of thrombin generation. Thus, Compound No. 3 is an inhibitor of fibrinolysis that is at least equivalent to aprotinin and more potent compared to tranexamic acid in all investigations in vitro so far.

Compound No. 3 offers a number of potential benefits compared to aprotinin; it is a synthetic compound with no risks of transmitting animal-derived diseases; it has a low molecular weight, so it is unlikely to elicit anaphylactic reactions; finally, due to its shorter half-life—terminal half-life is 20 min in rats and dogs—stable plasma concentrations may be more easily controlled.

In summary, Compound No. 3 is a small synthetic antifibrinolytic compound which concentration-dependently inhibits several serine proteases of the hemostatic system. It is not of animal origin and its profile is comparable to that of aprotinin with a stronger impact on the coagulation enzymes factor Xa and plasma kallikrein. Due to its low molecular weight, antigenicity is unlikely.

ADDITIONAL REFERENCES

Asghar et al., *Biochim. Biophys. Acta* 438:250-264, 1976
Asimakopoulos et al., *J. Thorac. Cardiovasc. Surg.* 120:361-9, 2000
Avidan et al., *Br. J. Anaesth.* 92:178-86, 2004
Bhoola et al., *Pharmacol. Rev.* 44:1-80, 1992
Brown et al., *Circulation* 115:2801-13, 2007
Cammerer et al., *Anesth. Analg.* 96:51-7, 2003
Collen et al., *J. Lab. Clin. Med.* 99:76-83, 1982
Dietrich et al., *Anesth. Analg.* 103:1074-81, 2006
Dietrich et al., *Ann. Thorac. Surg.* 84:1144-50, 2007
Dietrich et al., *Anesthesiology* 108:189-98, 2008
Dixon et al., *Biochem. J.* 55:170-171, 1953
Edmunds et al., *Ann. Thorac. Surg.* 82:2315-22, 2006
Fergusson et al., *New Engl. J. Med.* 358:2319-31, 2008
Ferraris et al., *Ann. Thorac. Surg.* 83:S27-86, 2007
Fritz et al., *Arzneim. Forsch./Drug. Res.* 33:479-94, 1983
Gerotziafas et al., *J. Thromb. Haemost.* 5:886-8, 2007
Gustafsson et al., *Thromb. Res.* 79:110-118, 1998
Henry et al., Cochrane Database Syst. Rev. CD001886 (2007)
Hill et al., *Anesth. Analg.* 84:1198-202, 1997
Karkouti et al., *Transfusion* 46:327-38, 2006
Katz et al., *Chem. Biol.* 8:1107-21, 2001
Kleinschnitz et al., *J. Exp. Med.* 203:513-8, 2006
Laffey et al., *Anesthesiology* 97:215-52, 2002
Landis et al., *Ann. Thorac. Surg.* 72:2169-75, 2001
Levy et al., *Ann. Thorac. Surg.* 75:S715-20, 2003
Mangano et al., *New Engl. J. Med.* 354:353-365, 2006
Mannucci et al., *New Engl. J. Med.* 356:2301-11, 2007
Mojcik et al., *Ann. Thorac. Surg.* 71:745-54, 2001
Mouton et al., *Lancet* 371:475-82, 2008
Muramatu and Fuji, *Biochim. Biophys. Acta.* 242:203-208, 1971
Muramatu and Fuji, *Biochim. Biophys. Acta.* 268:221-224, 1972
Muramatu et al., *Hoppe-Seyler's Z. Physiol. Chem.* 363:203-211, 1982
Ohno et al., *Thromb. Res.* 19:579-588, 1980
Okada et al., *Chem. Pharm. Bull.* 48:1964-1972, 2000
Okada et al., *Biopolymers* 51:41-50, 1999
Okada et al., *Bioorg. Med. Chem. Lett.* 10:2217-2221, 2000
Okamoto et al., *Thromb. Res.*, Suppl VIII, 131-141, 1988
Sanders and Seto, *J. Med. Chem.* 42:2969-2976, 1999
Satoh et al., *Chem. Pharm. Bull.* 33:647-654, 1985
Schechter and Berger, *Biochem. Biophys. Res. Comm.* 27:157-162, 1967
Schmaier, A. H., *Journal of Clinical Investigation* 109:1007-1009, 2002
Schweinitz et al., *J. Biol. Chem.*, 279:33613-33622, 2004
Sedrakyan et al., *J. Thorac. Cardiovasc. Surg.* 128:442-8, 2004
Sperzel et al., *J. Thromb. Haemost.* 5:2113-8, 2007
Sodha et al., *Expert Rev. Cardiovasc. Ther.* 4:151-160, 2006
Stürzebecher et al., *J. Med. Chem.* 40:3091-3099, 1997
Tada et al., *Biol. Pharm. Bull.* 24:520-524, 2001
Teno et al., *Chem. Pharm. Bull.*, 39:2930-2936, 1991
Tsuda et al., *Chem. Pharm. Bull.*, 49:1457-1463, 2001
Wachtfogel et al., *J. Thorac. Cardiovasc. Surg.* 106:1-9, 1993
Weitz, *Am. J. Cardiol.* 75:B 18-B22, 1995
Westaby, *J. Thorac. Cardiovasc. Surg.* 135:487-91, 2008
Xue and Seto, *J. Med. Chem.*, 48:6908-6917, 2005
Zufferey et al., *Anesthesiology* 105:1034-46, 2006
U.S. Pat. No. 5,602,253
U.S. Pat. No. 6,472,393
US 2006/0148901

Other Embodiments

The content of each publication, patent, and patent application mentioned in the present application is incorporated by reference. Although the invention has been described in details herein and illustrated in the accompanying drawings, it is to be understood that the invention is not limited to the embodiments described herein and that various changes and modifications may be effected without departing from the scope or spirit of the invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A compound of the formula (I)

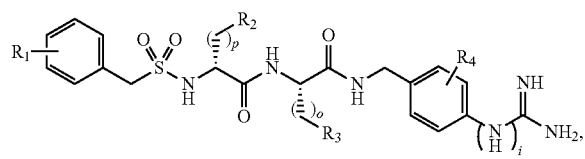

wherein
- $R_1$ is optionally present one or more times and each $R_1$ is, independently, hydrogen or $COOR_5$;
- $R_2$ is an optionally substituted ring system wherein said ring system is an aromatic or nonaromatic cyclic or bicyclic system comprising 5-13 carbon atoms;
- $R_3$ is an optionally substituted ring system wherein said ring system is selected from (i) an aromatic cyclic system comprising 5-6 carbon atoms, and (ii) an aromatic heterocycle comprising 3-5 carbon atoms and 1-2 nitrogen atoms, a nitrogen oxide, oxygen atom, or sulfur atom;
- $R_4$ is optionally present one or more times and each $R_4$ is, independently, hydrogen or a halogen;
- $R_5$ is hydrogen, a branched or linear lower alkyl group comprising 1-6 carbon atoms, a branched or linear aminoalkyl residue comprising 1-6 carbon atoms, a halogen or pseudohalogen residue, or a polyethylene glycol residue of the formula (II) or (III):

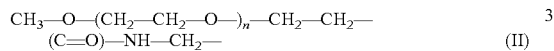

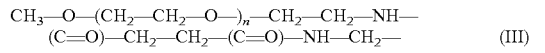

wherein said polyethylene glycol residue has a molecular weight of from 750 Da to 10,000 Da, and n is an integer from 25 to 250;
- o=1, 2 or 3;
- p=0, 1, 2, 3 or 4;
- i=0 or 1;

and salts thereof.

2. The compound of claim 1, wherein
- $R_5$ is methyl, ethyl, a branched or linear aminoalkyl residue comprising a methyl group, chlorine, a cyano group, or a polyethylene glycol residue of the formula (II) or (III) in which n is 18, 25, 50, 85, 125, or 250;
- $R_3$ is an optionally substituted ring system wherein said ring system is an aromatic heterocycle comprising 4-5 carbon atoms and one nitrogen atom or nitrogen oxide;
- $R_4$ is fluorine;
- o is 1;
- p is 3; and
- i is 0.

3. The compound of claim 1, wherein
- $R_1$ is a $COOR_5$ residue present once and in the meta or para position;
- $R_2$ is an optionally substituted ring system wherein said ring system is phenyl or napthyl;
- $R_3$ is phenyl or phenyl substituted with an alkylamino residue having 1-3 carbon atoms;
- $R_4$ is hydrogen;
- $R_5$ is hydrogen or a branched or linear lower alkyl group having 1-6 carbon atoms;
- o is 1 or 2; and
- i is 0.

4. The compound of claim 1, wherein $R_1$ is $COOR_5$ present once and in the meta or para position.

5. The compound of claim 4, wherein $R_5$ is hydrogen.

6. The compound of claim 1, wherein $R_2$ is a substituted ring system comprising a substituent selected from a halogen residue, an optionally fluorine-substituted branched or linear alkyl residue having 1-6 carbon atoms, an optionally fluorine-substituted branched or linear alkyloxy residue having 1-6 carbon atoms, a hydroxy residue, or a cyano residue.

7. The compound of claim 6, wherein said substituent is selected from chlorine, fluorine, methyl, tertiary butyl, and $OCH_3$.

8. The compound of claim 1, wherein $R_2$ is a nonaromatic cyclic system comprising 6 carbon atoms.

9. The compound of claim 1, wherein $R_3$ is a basic residue.

10. The compound of claim 1, wherein $R_3$ is a substituted ring system comprising a substituent selected from an alkylamino residue having 1-3 carbon atoms, an amidino residue, and guanidino residue.

11. The compound of claim 10, wherein said substituent is an alkylamino residue comprising 3 carbon atoms.

12. The compound of claim 1, wherein said compound is a salt selected from chloride, bromide, acetate, trifluoroacetate, and toluenesulfonate.

13. The compound of claim 1, wherein $R_2$ is selected from the following residues:

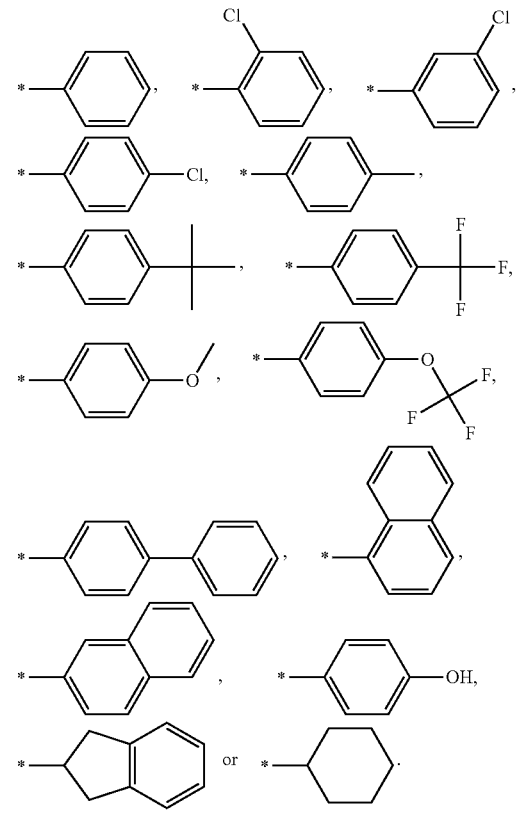

14. The compound of claim 13, wherein $R_2$ is

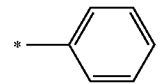

15. The compound of claim 1, wherein $R_3$ is selected from

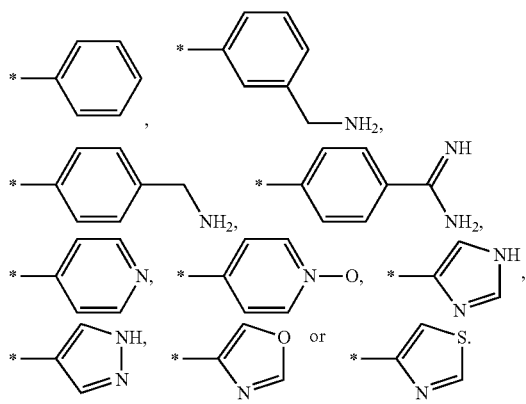
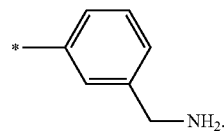
17. The compound of claim 1, or a salt thereof, wherein the compound is defined as follows:
16. The compound of claim 15, wherein $R_3$ is
| Compound No. | $R_1$ | $R_2$ | p | $R_3$ | o | i | $R_4$ |
|---|---|---|---|---|---|---|---|
| 1 | H | *-phenyl | 3 | *-C6H4-CH2-NH2 (3-) | 1 | 0 | — |
| 2 | 4-COOH | *-phenyl | 3 | *-C6H4-CH2-NH2 (3-) | 1 | 0 | — |
| 3 | 3-COOH | *-phenyl | 3 | *-C6H4-CH2-NH2 (3-) | 1 | 0 | — |
| 4 | 3-COOH | *-phenyl | 3 | *-C6H4-CH2-NH2 (3-) | 1 | 1 | — |
| 5 | 3-COOH | *-phenyl | 3 | *-C6H4-CH2-NH2 (3-) | 1 | 0 | 2-F |
| 6 | H | *-C6H4-Cl (3-) | 3 | *-C6H4-CH2-NH2 (3-) | 1 | 0 | — |
| 7 | H | *-C6H4-Cl (4-) | 3 | *-C6H4-CH2-NH2 (3-) | 1 | 0 | — |

-continued
| Compound No. | R₁ | R₂ | p | R₃ | o | i | R₄ |
|---|---|---|---|---|---|---|---|
| 8 | H | 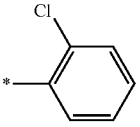 | 3 | 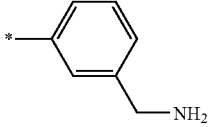 | 1 | 0 | — |
| 9 | H | 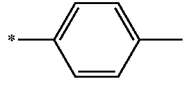 | 3 | 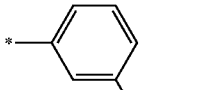 | 1 | 0 | — |
| 10 | H | 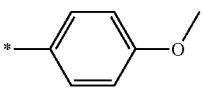 | 3 | 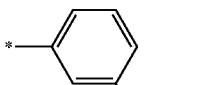 | 1 | 0 | — |
| 11 | H | 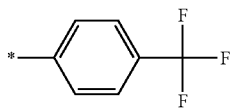 | 3 | 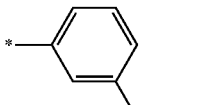 | 1 | 0 | — |
| 12 | H | 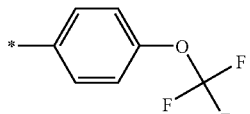 | 3 | 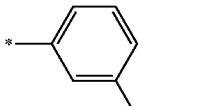 | 1 | 0 | — |
| 13 | H | 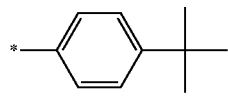 | 1 | 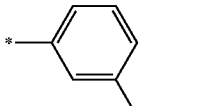 | 1 | 0 | — |
| 14 | H | 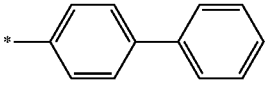 | 1 | 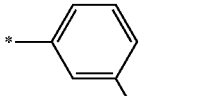 | 1 | 0 | — |
| 15 | H | 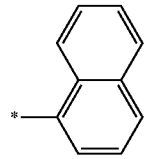 | 1 | 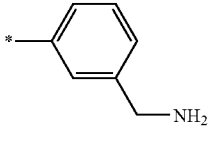 | 1 | 0 | — |
| 16 | 4-COOH | 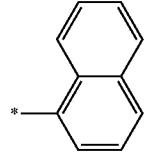 | 1 | 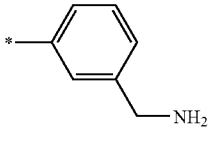 | 1 | 0 | — |
| 17 | H | 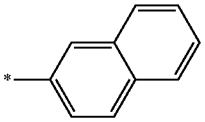 | 1 | 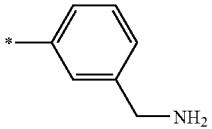 | 1 | 0 | — |

-continued
| Compound No. | R₁ | R₂ | p | R₃ | o | i | R₄ |
|---|---|---|---|---|---|---|---|
| 18 | 3-COOH | 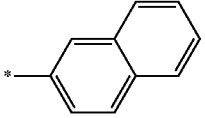 | 1 | 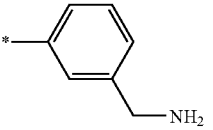 | 1 | 0 | — |
| 19 | 4-COOH | 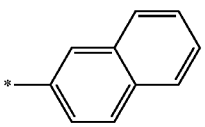 | 1 | 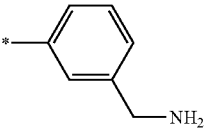 | 1 | 0 | — |
| 20 | H | 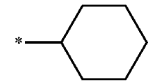 | 1 | 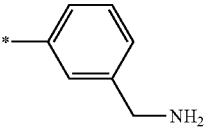 | 1 | 0 | — |
| 21 | H | 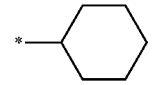 | 3 | 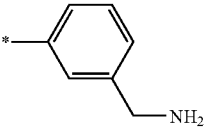 | 1 | 0 | — |
| 22 | H | 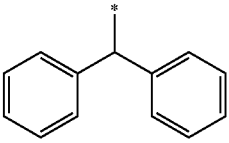 | 0 | 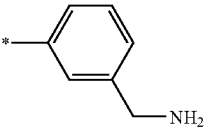 | 1 | 0 | — |
| 23 | 3-COOH | 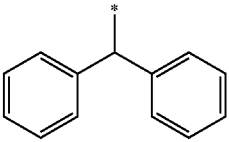 | 0 | 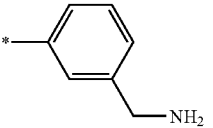 | 1 | 0 | — |
| 24 | H | 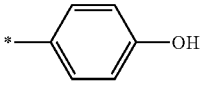 | 2 | 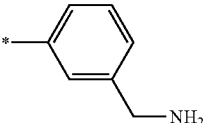 | 1 | 0 | — |
| 25 | 3-COOH | 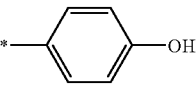 | 2 | 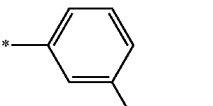 | 1 | 0 | — |
| 26 | H | 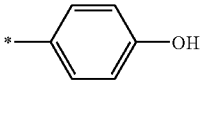 | 2 | 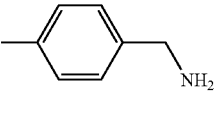 | 2 | 0 | — |
| 27 | H | 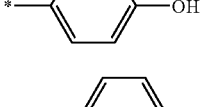 | 2 | 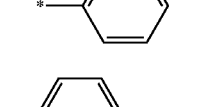 | 2 | 0 | — |
| 28 | H | 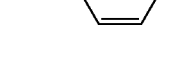 | 3 | 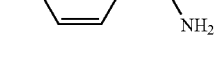 | 1 | 0 | — |

-continued
| Compound No. | R₁ | R₂ | p | R₃ | o | i | R₄ |
|---|---|---|---|---|---|---|---|
| 29 | 4-COOH | 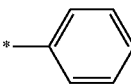 | 3 | 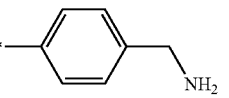 | 1 | 0 | — |
| 30 | 3-COOH | 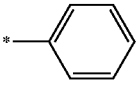 | 3 | 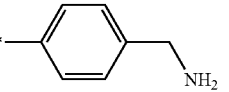 | 1 | 0 | — |
| 31 | H | 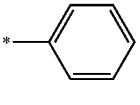 | 3 | 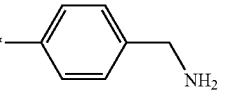 | 2 | 0 | — |
| 32 | H | 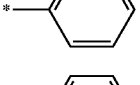 | 3 | 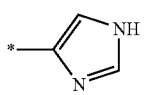 | 1 | 0 | — |
| 33 | 3-COOH | 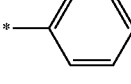 | 3 | 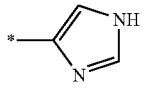 | 1 | 0 | — |
| 34 | H | 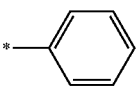 | 3 | 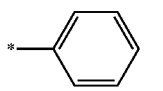 | 2 | 0 | — |
| 35 | 4-COOH | 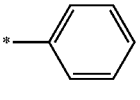 | 3 | 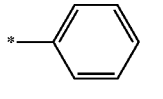 | 2 | 0 | — |
| 36 | 3-COOH | 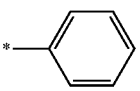 | 3 | 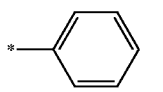 | 2 | 0 | — |
| 37 | H | 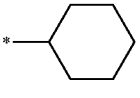 | 1 | 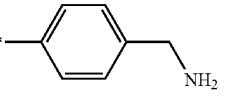 | 2 | 0 | — |
| 38 | H | 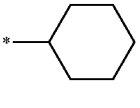 | 1 | 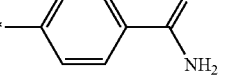 | 2 | 0 | — |
| 39 | H | 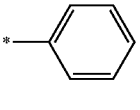 | 3 | 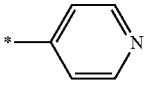 | 2 | 0 | — |
| 40 | 3-COOH | 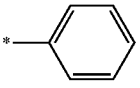 | 3 | 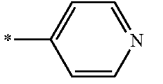 | 2 | 0 | — |
| 41 | H | 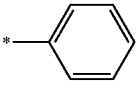 | 3 | 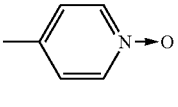 | 2 | 0 | — |
| 42 | 3-COOH | 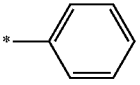 | 3 | 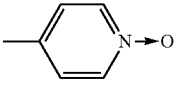 | 2 | 0 | — |
| 43 | H | 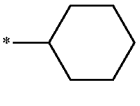 | 1 | 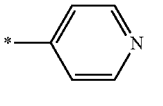 | 2 | 0 | — |

-continued

| Compound No. | R₁ | R₂ | p | R₃ | o | i | R₄ |
|---|---|---|---|---|---|---|---|
| 44 | H | *-phenyl | 2 | *-4-pyridyl | 2 | 0 | — |
| 45 | H | *-phenyl-CN (3-cyanophenyl) | 1 | *-4-pyridyl | 2 | 0 | — |
| 47 | H | *-phenyl-OH (4-hydroxyphenyl) | 2 | *-4-pyridyl | 2 | 0 | —. |

18. A compound having the following structure:

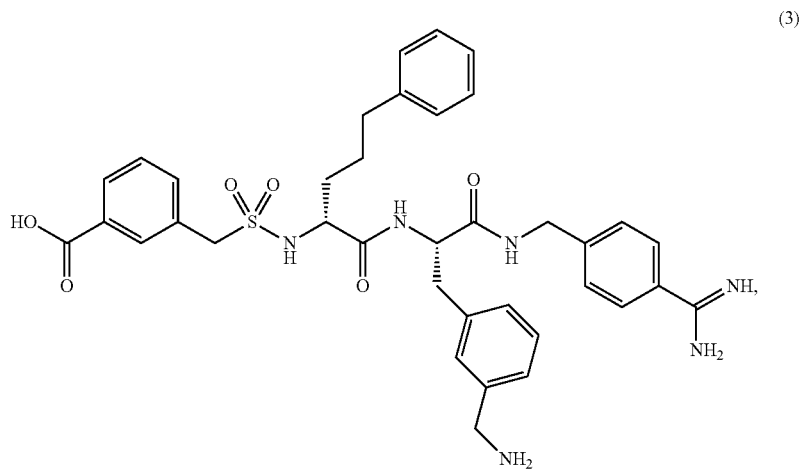

(3)

or a salt thereof.

19. A compound of the formula (IV)

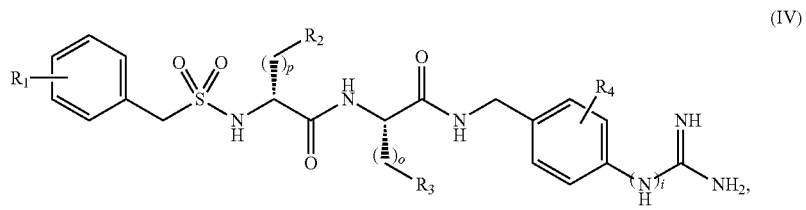

(IV)

wherein

R₁ is optionally present one or more times and each R₁ is, independently, hydrogen or COOR₅;

R₂ is a branched or linear alkyloxy residue comprising 1-6 carbon atoms, a branched or linear alkyloxycarbonylamido residue comprising 1-6 carbon atoms, or a polyethylene glycol residue of the formula (V) or (VI) with n as defined below;

R₃ selected from the following residues:

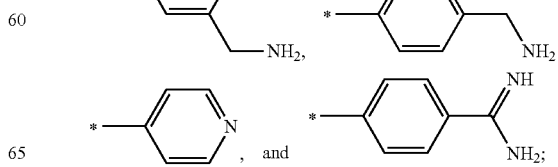

, and $R_4$ is optionally present one or more times and each $R_4$ is, independently, hydrogen or a halogen;

$R_5$ is hydrogen, a branched or linear lower alkyl group comprising 1-6 carbon atoms, a branched or linear aminoalkyl residue comprising 1-6 carbon atoms, a halogen or pseudohalogen residue, or a polyethylene glycol residue of the formula (V) or (VI)

$$CH_3\text{—}O\text{—}(CH_2\text{—}CH_2\text{—}O\text{—})_n\text{—}CH_2\text{—}CH_2\text{—}(C{=}O)\text{—}NH\text{—}CH_2\text{—} \quad (V)$$

$$CH_3\text{—}O\text{—}(CH_2\text{—}CH_2\text{—}O\text{—})_n\text{—}CH_2\text{—}CH_2\text{—}NH\text{—}(C{=}O)\text{—}CH_2\text{—}CH_2\text{—}(C{=}O)\text{—}NH\text{—}CH_2\text{—} \quad (VI)$$

wherein said polyethylene glycol residue has a molecular weight of from 750 Da to 10,000 Da and n is an integer from 25 to 250;

o=1 or 2;
p=1, 2, 3 or 4;
i=0 or 1, in particular 0;
and salts thereof.

20. The compound of claim 19, wherein
$R_5$ is methyl, ethyl, a branched or linear aminoalkyl residue comprising a methyl group, chlorine, a cyano group, or a polyethylene glycol residue of the formula (V) or (VI) in which n is 18, 25, 50, 85, 125, or 250;

$R_2$ is a branched or linear alkyloxy residue comprising a tertiary butyl group or a branched or linear alkyloxycarbonylamido residue having a tertiary butyl group;

$R_3$ is

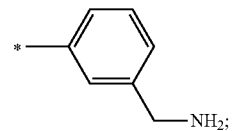

$R_4$ is fluorine;
p is 1 or 4; and
i is 0.

21. The compound of claim 19, wherein $R_1$ is $COOR_5$ present once and in meta or para position.

22. The compound of claim 21, wherein $R_5$ is hydrogen.

23. The compound of claim 19, wherein said compound is a salt selected from chloride, bromide, acetate, trifluoroacetate, and toluenesulfonate.

24. A compound, or a salt thereof, wherein the compound is defined as follows:

| Compound No. | $R_1$ | $R_2$ | p | $R_3$ | o |
|---|---|---|---|---|---|
| 57 | H | | 4 | | 1 |
| 58 | 4-COOH | | 4 | | 1 |
| 59 | H | *—NH$_2$ | 4 | | 1 |
| 60 | H | | 1 | | 1 |
| 61 | H | *—NH$_2$ | 1 | | 1 |
| 62 | H | | 4 | | 2 |

-continued

| Compound No. | R₁ | R₂ | p | R₃ | o |
|---|---|---|---|---|---|
| 63 | H | *—O—C(CH₃)₃ | 1 | *-C₆H₄-CH₂NH₂ (3-) | 1 |
| 64 | 4-COOMe | *—O—C(CH₃)₃ | 1 | *-C₆H₄-CH₂NH₂ (3-) | 1 |
| 65 | 4-COOH | *—O—C(CH₃)₃ | 1 | *-C₆H₄-CH₂NH₂ (3-) | 1 |
| 66 | 3-COOMe | *—O—C(CH₃)₃ | 1 | *-C₆H₄-CH₂NH₂ (3-) | 1 |
| 67 | 3-COOH | *—O—C(CH₃)₃ | 1 | *-C₆H₄-CH₂NH₂ (3-) | 1 |
| 68 | H | *—OH | 1 | *-C₆H₄-CH₂NH₂ (3-) | 1 |
| 69 | 4-COOMe | *—OH | 1 | *-C₆H₄-CH₂NH₂ (3-) | 1 |
| 70 | 4-COOH | *—OH | 1 | *-C₆H₄-CH₂NH₂ (3-) | 1 |
| 71 | H | *—O—C(CH₃)₃ | 1 | *-C₆H₄-CH₂NH₂ (3-) | 1 |
| 72 | H | *—OH | 1 | *-C₆H₄-CH₂NH₂ (3-) | 1 |
| 73 | H | *—O—C(CH₃)₃ | 1 | *-C₆H₄-CH₂NH₂ (3-) | 2 |

25. A medicament comprising the compound of claim 1, or a salt thereof.

26. The medicament of claim 25, wherein said medicament is for the treatment of blood loss.

27. The medicament of claim 26, wherein said blood loss occurs in hyperfibrinolytic conditions, in organ transplants, or cardiac surgical procedures.

28. A fibrin adhesive comprising the compound of claim 1, or a salt thereof.

29. The salt of the compound of claim 18.

30. A medicament comprising the compound of claim 18, or a salt thereof.

31. The medicament of claim 30, wherein said medicament is for the treatment of blood loss.

32. The medicament of claim 31, wherein said blood loss occurs in hyperfibrinolytic conditions, in organ transplants, or cardiac surgical procedures.

33. A fibrin adhesive comprising the compound of claim 18, or a salt thereof.

* * * * *